US012793823B2

(12) United States Patent
Kimura

(10) Patent No.: US 12,793,823 B2
(45) Date of Patent: Nov. 10, 2026

(54) INFORMATION PROCESSING APPARATUS, INFORMATION PROCESSING METHOD, ENDOSCOPE SYSTEM, AND REPORT CREATION SUPPORT DEVICE

(71) Applicant: FUJIFILM Corporation, Tokyo (JP)

(72) Inventor: Yuya Kimura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/618,565

(22) Filed: Mar. 27, 2024

(65) Prior Publication Data

US 2024/0266017 A1 Aug. 8, 2024

Related U.S. Application Data

(63) Continuation of application No. PCT/JP2022/033530, filed on Sep. 7, 2022.

(30) Foreign Application Priority Data

Oct. 4, 2021 (JP) ................................ 2021-163514

(51) Int. Cl.
*G16H 15/00* (2018.01)
*G06F 3/14* (2006.01)
(Continued)

(52) U.S. Cl.
CPC ............... *G16H 15/00* (2018.01); *G06F 3/14* (2013.01); *G06V 10/25* (2022.01); *G16H 30/20* (2018.01); *G06V 2201/07* (2022.01)

(58) Field of Classification Search
None
See application file for complete search history.

(56) References Cited

U.S. PATENT DOCUMENTS

2011/0246875 A1* 10/2011 Parker .................. G06F 3/0482 715/702
2018/0092509 A1* 4/2018 Yamaki ............... A61B 1/0661
(Continued)

FOREIGN PATENT DOCUMENTS

JP 2005-143782 A 6/2005
JP 2015-143782 A 8/2015
(Continued)

OTHER PUBLICATIONS

International Search Report issued in PCT/JP2022/033530; mailed Nov. 22, 2022.

(Continued)

*Primary Examiner* — Robert A Sorey
(74) *Attorney, Agent, or Firm* — Studebaker Brackett PLLC

(57) ABSTRACT

There are provided an information processing apparatus, an information processing method, an endoscope system, and a report creation support device which can efficiently input information necessary for generating a report. Images captured by an endoscope are acquired, and the acquired images are displayed on a display unit. In addition, the acquired images are input to a plurality of recognizers, and a recognizer that has output a specific recognition result is detected from among the plurality of recognizers. Options for an item corresponding to the detected recognizer is displayed on the display unit, and an input of selection for the displayed options is accepted.

27 Claims, 39 Drawing Sheets

(51) Int. Cl.
*G06V 10/25* (2022.01)
*G16H 30/20* (2018.01)

(56) References Cited

U.S. PATENT DOCUMENTS

| | | | | |
|---|---|---|---|---|
| 2018/0218499 | A1* | 8/2018 | Kamon | A61B 1/044 |
| 2020/0143538 | A1 | 5/2020 | Kamon | |
| 2020/0143936 | A1 | 5/2020 | Kamon et al. | |
| 2021/0195325 | A1* | 6/2021 | Edry | H04L 65/1093 |
| 2022/0092362 | A1 | 3/2022 | Oosake | |

FOREIGN PATENT DOCUMENTS

| | | | | |
|---|---|---|---|---|
| JP | 2016-021216 | A | 2/2016 | |
| JP | 2016-062488 | A | 4/2016 | |
| JP | 2020-081332 | A | 6/2020 | |
| WO | 2019/008941 | A1 | 1/2019 | |
| WO | 2019/008942 | A1 | 1/2019 | |
| WO | WO-2019054045 | A1 * | 3/2019 | G06V 10/80 |
| WO | 2019/065111 | A1 | 4/2019 | |
| WO | WO-2020239514 | A1 * | 12/2020 | A61B 34/20 |

OTHER PUBLICATIONS

International Preliminary Report on Patentability (Chapter I) and Written Opinion of the International Searching Authority issued in PCT/JP2022/033530; issued Apr. 9, 2024.

"Notice of Reasons for Refusal" Office Action issued in JP 2023-552759; mailed by the Japanese Patent Office on Jun. 24, 2026.

* cited by examiner

FIG. 16

72

| TUMOR |
|---|
| SERRATED LESION |
| FAMILIAL ADENOMATOUS POLYPOSIS |
| ULCERATIVE COLITIS |
| COLON POLYP |
| HYPERPLASTIC POLYP |
| JUVENILE POLYP |
| INFLAMMATORY POLYP |

FIG. 22

| TREATMENT TOOL | TREATMENT NAME TO BE DISPLAYED | DISPLAY RANK | DEFAULT OPTION |
|---|---|---|---|
| BIOPSY FORCEPS | CFP | 1 | CSP |
| | Biopsy | 2 | |
| SNARE | Polypectomy | 1 | Polypectomy |
| | EMR | 2 | |
| | Cold Polypectomy | 3 | |

FIG. 26

77

| | |
|---|---|
| DIAGNOSIS | COLON POLYP |
| FINDING 1 | Is |
| FINDING 2 | JNET Type2A |
| FINDING 3 | LESS THAN 5 mm |
| TREATMENT | EMR |
| HEMOSTASIS | 1 |

INFORMATION PROCESSING APPARATUS, INFORMATION PROCESSING METHOD, ENDOSCOPE SYSTEM, AND REPORT CREATION SUPPORT DEVICE

CROSS-REFERENCE TO RELATED APPLICATIONS

The present application is a Continuation of PCT International Application No. PCT/JP2022/033530 filed on Sep. 7, 2022 claiming priority under 35 U.S.C § 119(a) to Japanese Patent Application No. 2021-163514 filed on Oct. 4, 2021. Each of the above applications is hereby expressly incorporated by reference, in its entirety, into the present application.

BACKGROUND OF THE INVENTION

1. Field of the Invention

The present invention relates to an information processing apparatus, an information processing method, an endoscope system, and a report creation support device, and particularly relates to an information processing apparatus, an information processing method, an endoscope system, and a report creation support device which process information on an examination by an endoscope.

2. Description of the Related Art

In an examination using an endoscope, a report in which findings and the like are described after the examination has ended is created. JP2016-21216A discloses a technique of inputting information necessary for generating a report in real time during the examination. In JP2016-21216A, in a case where a site of a hollow organ is designated by a user during the examination, a disease name selection screen and a characteristic selection screen are displayed in order on a display unit, and information on the disease name and information on the characteristic selected on each selection screen are recorded in a storage unit in association with information on the designated site of the hollow organ.

SUMMARY OF THE INVENTION

However, in JP2016-21216A, since it is necessary to input the information on the site, disease name, characteristics, and the like collectively, it takes time to input, and there is a disadvantage that it is forced to interrupt the examination.

The present invention is made in view of such circumstances, and an object thereof is to provide an information processing apparatus, an information processing method, an endoscope system, and a report creation support device which can efficiently input information necessary for generating a report.

(1) An information processing apparatus comprising: a first processor, in which the first processor acquires an image captured by an endoscope, causes a first display unit to display the acquired image, inputs the acquired image to a plurality of recognizers, detects a recognizer that has output a specific recognition result, from among the plurality of recognizers, causes the first display unit to display options for an item corresponding to the detected recognizer, and accepts an input of selection for the displayed options.

(2) The information processing apparatus according to (1), in which the first processor accepts the input of the selection for the displayed options from a plurality of input devices.

(3) The information processing apparatus according to (1), in which the first processor is able to accept the input of the selection from a plurality of input devices for the displayed options, and sets at least one input device that accepts the input of the selection for the options from the plurality of input devices according to the detected recognizer.

(4) The information processing apparatus according to any one of (1) to (3), in which in a case where the first processor detects that a specific recognizer has output a specific recognition result, the first processor causes the first display unit to display the options for the item corresponding to the output recognition result.

(5) The information processing apparatus according to any one of (1) to (4), in which the first processor causes the first display unit to display the options while the detected recognizer is outputting a specific recognition result.

(6) The information processing apparatus according to any one of (1) to (5), in which in a case where the first processor detects that a specific recognizer has output a specific recognition result, the first processor causes the first display unit to display the recognition result output from the detected recognizer.

(7) The information processing apparatus according to (6), in which the first processor causes the first display unit to display the recognition result while the recognition result is being output from the detected recognizer.

(8) The information processing apparatus according to any one of (1) to (7), in which in a case where the first processor detects that a specific recognizer has output a specific recognition result, the first processor causes the first display unit to display the options for a plurality of items in order.

(9) The information processing apparatus according to any one of (1) to (7), in which in a case where the first processor detects that a specific recognizer has output a specific recognition result, the first processor causes the first display unit to display the options for an item designated from among a plurality of items.

(10) The information processing apparatus according to any one of (1) to (9), in which in a case where the first processor detects that a specific recognizer has output a specific recognition result, the first processor causes the first display unit to display the options in a state where one option is selected in advance.

(11) The information processing apparatus according to any one of (1) to (10), in which the first processor accepts the input of the selection for the options for a period set for each recognizer.

(12) The information processing apparatus according to (11), in which at least one recognizer accepts the input of the selection for the options while a specific recognition result is being output.

(13) The information processing apparatus according to (11) or (12), in which at least one recognizer continuously accepts the input of the selection for the options after the acceptance of the input of the selection for the options starts, except for a specific period.

(14) The information processing apparatus according to (13), in which the specific period is a period in which the input of the selection for the options for the item corresponding to a specific recognizer is being accepted.

(15) The information processing apparatus according to any one of (1) to (14), in which in a case where the first processor detects, while the input of the selection for the options for the item corresponding to a specific recognizer is being accepted, that another specific recognizer has output a specific recognition result, the first processor switches the options to be displayed on the first display unit to the options for the item corresponding to the newly detected recognizer.

(16) The information processing apparatus according to any one of (1) to (15), in which the first processor causes the first display unit to display a figure or a symbol corresponding to the detected recognizer.

(17) The information processing apparatus according to any one of (1) to (16), in which the first processor causes the first display unit to display the image in a first region set on a screen of the first display unit, and causes the first display unit to display the options for the item in a second region set in a different region from the first region.

(18) The information processing apparatus according to (17), in which the second region is set in a vicinity of a position where a treatment tool appears within the image displayed in the first region.

(19) The information processing apparatus according to any one of (1) to (18), in which the first processor causes the first display unit to display information on the option selected for each item.

(20) The information processing apparatus according to (19), in which the first processor causes the first display unit to display the information on the option selected for each item while the input of the selection of the options is being accepted.

(21) The information processing apparatus according to any one of (1) to (20), in which one of the plurality of recognizers is a first recognizer that detects a specific region of a hollow organ using image recognition, and the first processor causes the first display unit to display options for selecting a site of the hollow organ as the options for the item corresponding to the first recognizer.

(22) The information processing apparatus according to any one of (1) to (21), in which one of the plurality of recognizers is a second recognizer that discriminates a lesion part using image recognition, and the first processor causes the first display unit to display options for findings as the options for the item corresponding to the second recognizer.

(23) The information processing apparatus according to (22), in which the options for the findings include at least one of options for a macroscopic item, options for an item regarding a JNET classification, or options for an item regarding a size.

(24) The information processing apparatus according to any one of (1) to (23), in which one of the plurality of recognizers is a third recognizer that detects a treatment or a treatment tool using image recognition, and the first processor causes the first display unit to display options for a treatment name as the options for the item corresponding to the third recognizer.

(25) The information processing apparatus according to any one of (1) to (24), in which one of the plurality of recognizers is a fourth recognizer that detects a hemostasis treatment or a hemostasis treatment tool using image recognition, and the first processor causes the first display unit to display options for a hemostatic method or the number of hemostasis treatment tools as the options for the item corresponding to the fourth recognizer.

(26) The information processing apparatus according to (25), in which in a case where a specific hemostatic method is selected, the first processor causes the first display unit to further display the options for the number of hemostasis treatment tools.

(27) The information processing apparatus according to any one of (1) to (26), in which an input device by which selection of the options is input includes at least one of an audio input device, a switch, or a gaze input device.

(28) A report creation support device that supports creation of a report, the report creation support device comprising: a second processor, in which the second processor causes a second display unit to display a report creation screen with a plurality of input fields, acquires information on the options for each item input in the information processing apparatus according to any one of (1) to (27), automatically fills the corresponding input field with the acquired information on the options for the item, and accepts correction of the information of the automatically filled input field.

(29) The report creation support device according to (28), in which the second processor displays the automatically filled input field to be distinguishable from other input fields on the report creation screen.

(30) An endoscope system comprising: an endoscope; the information processing apparatus according to any one of (1) to (27); and an input device.

(31) An information processing method comprising: a step of acquiring an image captured by an endoscope; a step of causing a first display unit to display the acquired image; a step of inputting the acquired image to a plurality of recognizers; a step of detecting a recognizer that has output a specific recognition result, from among the plurality of recognizers; a step of causing the first display unit to display options for an item corresponding to the detected recognizer; and a step of accepting an input of selection for the displayed options.

According to the present invention, it is possible to efficiently input information necessary for generating a report.

BRIEF DESCRIPTION OF THE DRAWINGS

FIG. 16 is a diagram illustrating an example of a diagnosis name selection box.

FIG. 22 is a diagram illustrating an example of a table.

FIG. 26 is a diagram illustrating an example of an input information display box.

DESCRIPTION OF THE PREFERRED EMBODIMENTS

Hereinafter, preferred embodiments of the present invention will be described in detail with reference to the accompanying drawings.

[Endoscopic Image Diagnosis Support System]

Here, a case where the present invention is applied to an endoscopic image diagnosis support system will be described as an example. The endoscopic image diagnosis support system is a system that supports detection and discrimination of a lesion or the like in an endoscopy. In the following, an example of application to an endoscopic image diagnosis support system that supports detection and discrimination of a lesion and the like in a lower digestive tract endoscopy (large intestine examination) will be described.

Figure 1:
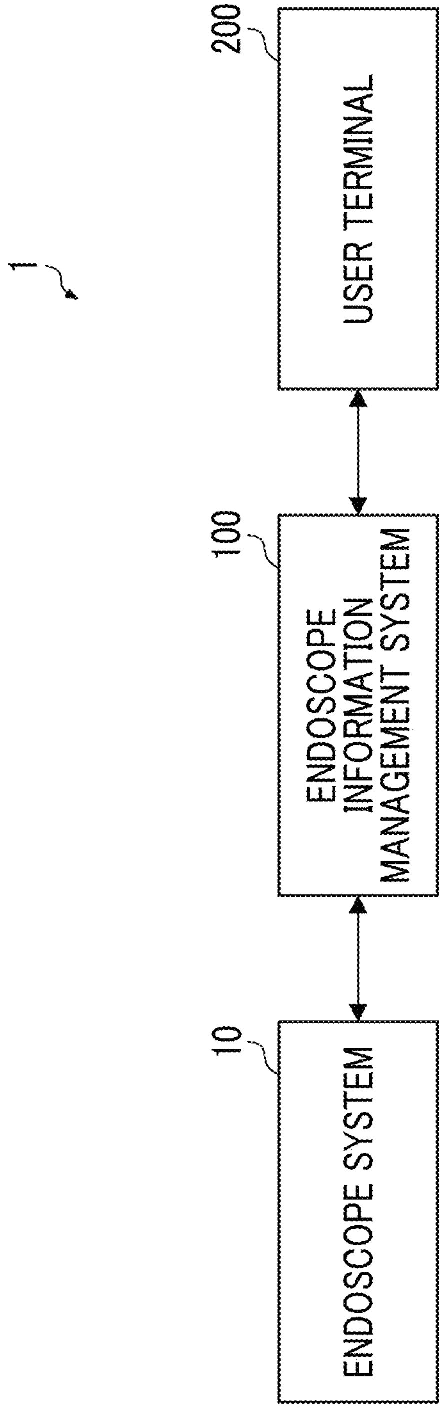
FIG. 1 is a block diagram illustrating an example of a system configuration of an endoscopic image diagnosis support system.

FIG. 1 is a block diagram illustrating an example of a system configuration of the endoscopic image diagnosis support system.

As illustrated in the figure, an endoscopic image diagnosis support system 1 of the present embodiment has an endoscope system 10, an endoscope information management system 100, and a user terminal 200.

[Endoscope System]

Figure 2:
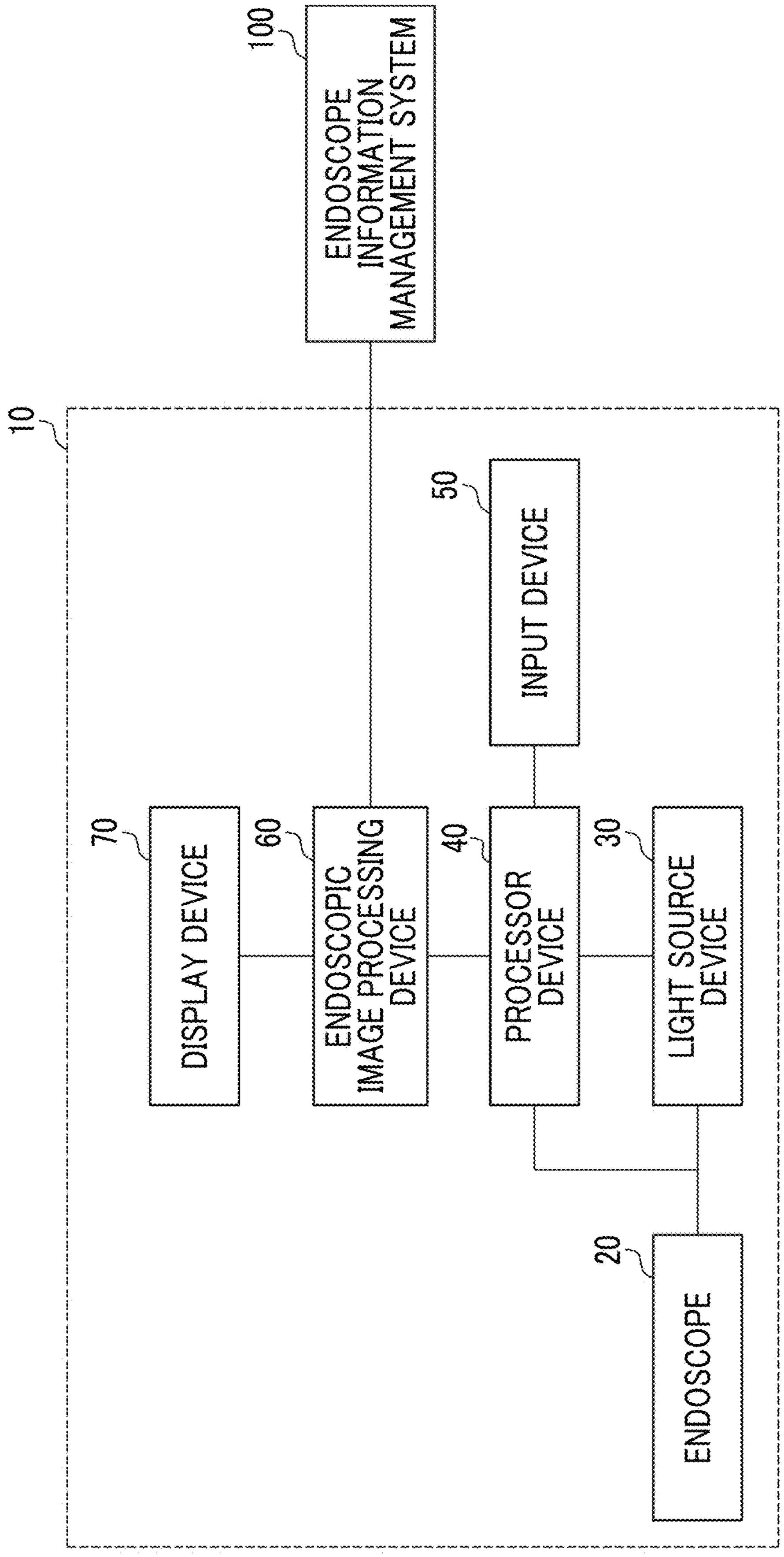
FIG. 2 is a block diagram illustrating an example of a system configuration of an endoscope system.

FIG. 2 is a block diagram illustrating an example of a system configuration of the endoscope system.

The endoscope system 10 of the present embodiment is configured as a system capable of an observation using special light (special light observation) in addition to an observation using white light (white light observation). In the special light observation, a narrow-band light observation is included. In the narrow-band light observation, a blue laser imaging observation (BLI observation), a narrow band imaging observation (NBI observation), a linked color imaging observation (LCI observation), and the like are included. Note that the special light observation itself is a well-known technique, so detailed description thereof will be omitted.

As illustrated in FIG. 2, the endoscope system 10 of the present embodiment has an endoscope 20, a light source device 30, a processor device 40, an input device 50, an endoscopic image processing device 60, a display device 70, and the like.

[Endoscope]

Figure 3:
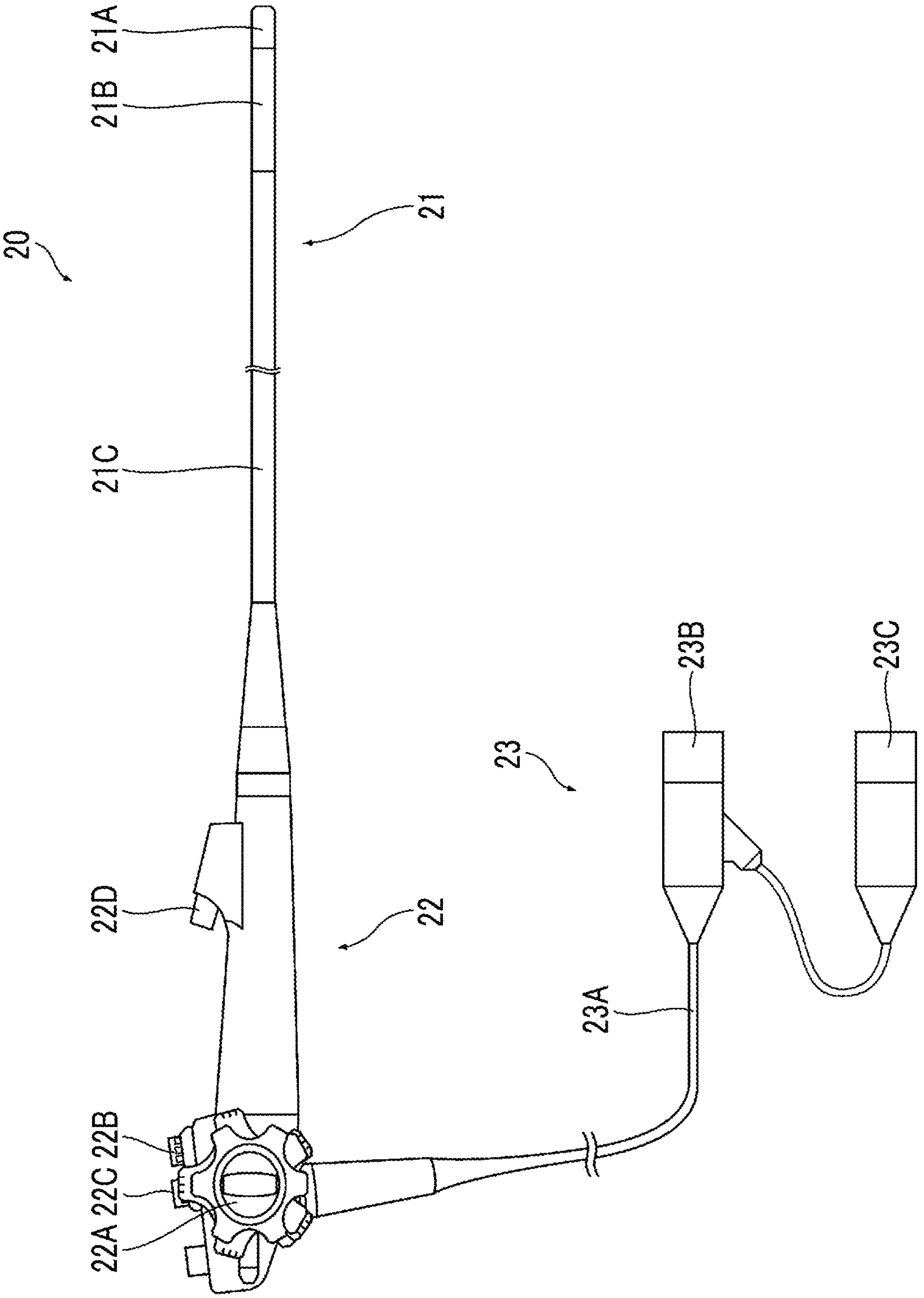
FIG. 3 is a diagram illustrating a schematic configuration of an endoscope.

FIG. 3 is a diagram illustrating a schematic configuration of the endoscope.

The endoscope 20 of the present embodiment is an endoscope for a lower digestive organ. As illustrated in FIG. 3, the endoscope 20 is a flexible endoscope (electronic endoscope), and has an insertion part 21, an operation part 22, and a connecting part 23.

The insertion part 21 is a part to be inserted into a hollow organ (large intestine in the present embodiment). The insertion part 21 has a distal end portion 21A, a bendable portion 21B, and a soft portion 21C in order from a distal end side.

Figure 4:
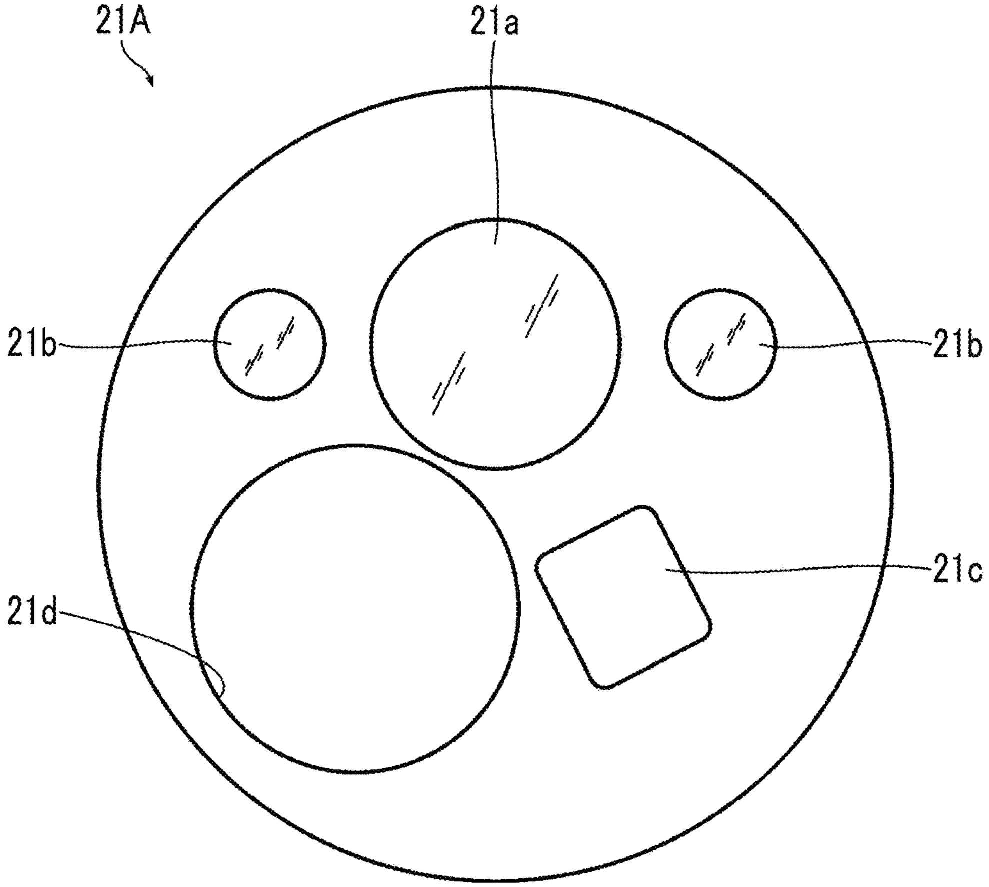
FIG. 4 is a diagram illustrating an example of a configuration of an edge surface of a distal end portion of an insertion part of the endoscope.

FIG. 4 is a diagram illustrating an example of a configuration of an edge surface of a distal end portion of the insertion part of the endoscope.

As illustrated in the figure, in the edge surface of the distal end portion 21A, an observation window 21*a*, illumination windows 21*b*, an air/water supply nozzle 21*c*, a forceps outlet 21*d*, and the like are provided. The observation window 21*a* is a window for an observation. The inside of the hollow organ is imaged through the observation window 21*a*.

Imaging is performed via an optical system and an image sensor (not illustrated) built in the distal end portion 21A. As the image sensor, for example, a complementary metal-oxide-semiconductor image sensor (CMOS image sensor), a charge-coupled device image sensor (CCD image sensor), or the like is used. The illumination windows 21*b* are windows for illumination. The inside of the hollow organ is irradiated with illumination light via the illumination windows 21*b*. The air/water supply nozzle 21*c* is a nozzle for cleaning.

A cleaning liquid and a drying gas are sprayed from the air/water supply nozzle 21*c* toward the observation window 21*a*. The forceps outlet 21*d* is an outlet for a treatment tool such as forceps. The forceps outlet 21*d* functions as a suction port for sucking body fluids and the like.

Figure 5:
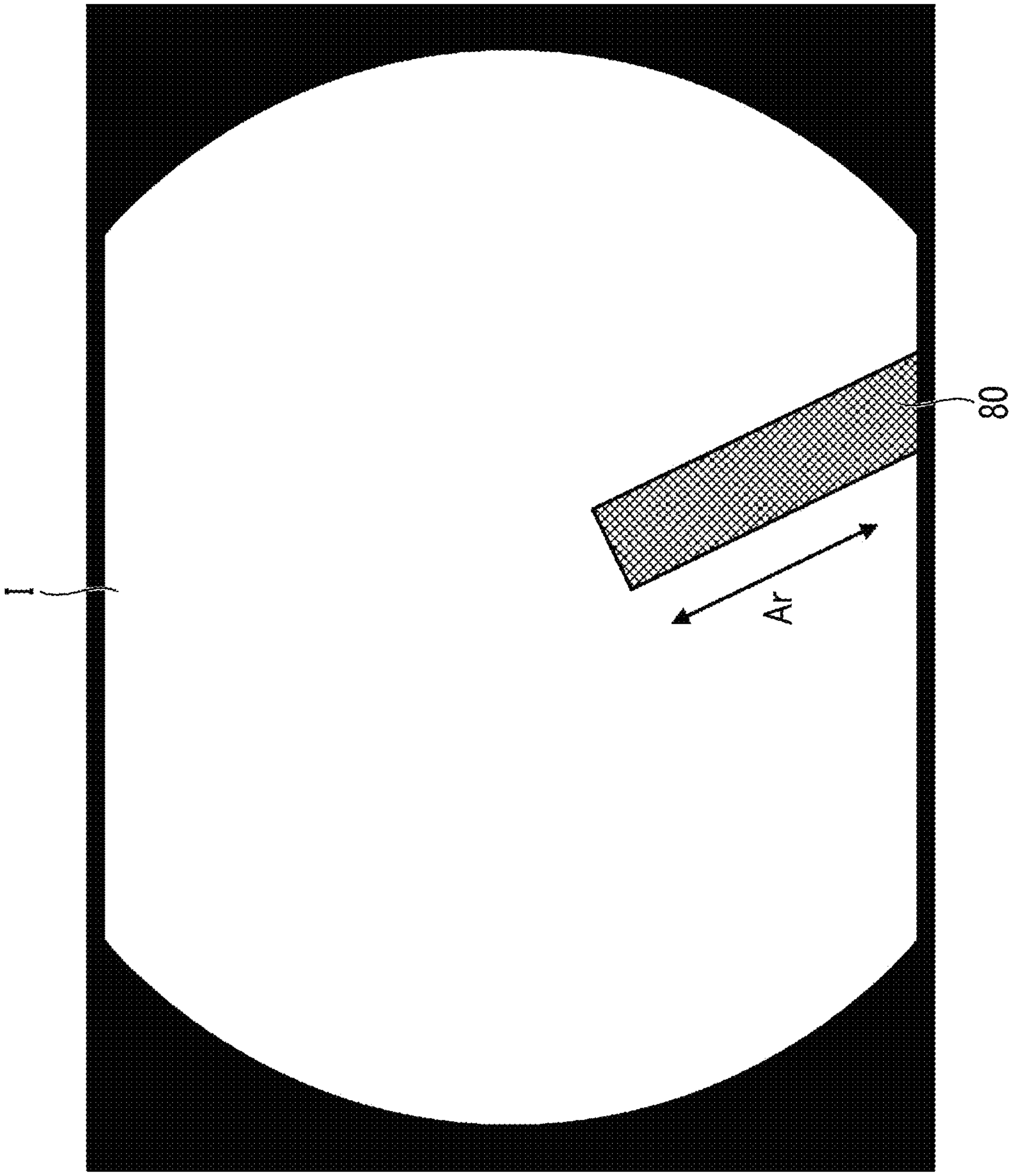
FIG. 5 is a diagram illustrating an example of an endoscopic image in a case where a treatment tool is used.

FIG. 5 is a diagram illustrating an example of an endoscopic image in a case where a treatment tool is used.

A position of the forceps outlet 21*d* is fixed with respect to a position of the observation window 21*a*. Therefore, in a case where a treatment tool is used, the treatment tool always appears from a certain position in the image, and is taken in and out along a certain direction.

FIG. 5 illustrates an example of a case in which a treatment tool 80 appears from a lower right position in an endoscopic image I, and is moved along a direction (forceps direction) indicated by an arrow Ar.

The bendable portion 21B is a portion that is bent according to an operation of an angle knob 22A of the operation part 22. The bendable portion 21B is bent in four directions of up, down, left, and right.

The soft portion 21C is an elongated portion provided between the bendable portion 21B and the operation part 22. The soft portion 21C has flexibility.

The operation part 22 is a part that is held by an operator to perform various operations. The operation part 22 includes various operation members. As an example, the operation part 22 includes the angle knob 22A for a bending operation of the bendable portion 21B, an air/water supply button 22B for performing an air/water supply operation, a suction button 22C for performing a suction operation, and the like. In addition, the operation part 22 includes an operation member (shutter button) for imaging a static image, an operation member for switching an observation mode, an operation member for switching ON and OFF of various support functions, and the like. In addition, the operation part 22 includes a forceps insertion port 22D for inserting a treatment tool such as forceps. The treatment tool inserted from the forceps insertion port 22D is drawn out from the forceps outlet 21*d* (refer to FIG. 4) on a distal end of the insertion part 21. As an example, the treatment tool includes biopsy forceps, snares, and the like.

The connecting part 23 is a part for connecting the endoscope 20 to the light source device 30, the processor device 40, and the like. The connecting part 23 has a cord 23A extending from the operation part 22, and a light guide connector 23B and a video connector 23C that are provided on a distal end of the cord 23A. The light guide connector 23B is a connector for connecting to the light source device 30. The video connector 23C is a connector for connecting to the processor device 40.

[Light Source Device]

The light source device 30 generates illumination light. As described above, the endoscope system 10 of the present embodiment has a function of the special light observation in addition to the normal white light observation. Therefore, the light source device 30 has a function of generating light (for example, narrow-band light) corresponding to the special light observation in addition to the normal white light. Note that, as described above, the special light observation itself is a well-known technique, so the description for the light generation will be omitted.

[Processor Device]

The processor device 40 integrally controls the operation of the entire endoscope system. The processor device 40 includes, as a hardware configuration, a processor, a main storage unit, an auxiliary storage unit, a communication unit, and the like. That is, the processor device 40 has a so-called computer configuration as the hardware configuration. For example, the processor is configured by a central processing unit (CPU) and the like. For example, the main storage unit is configured by a random-access memory (RAM) and the like. The auxiliary storage unit is configured by, for example, a flash memory, a hard disk drive (HDD), and the like.

Figure 6:
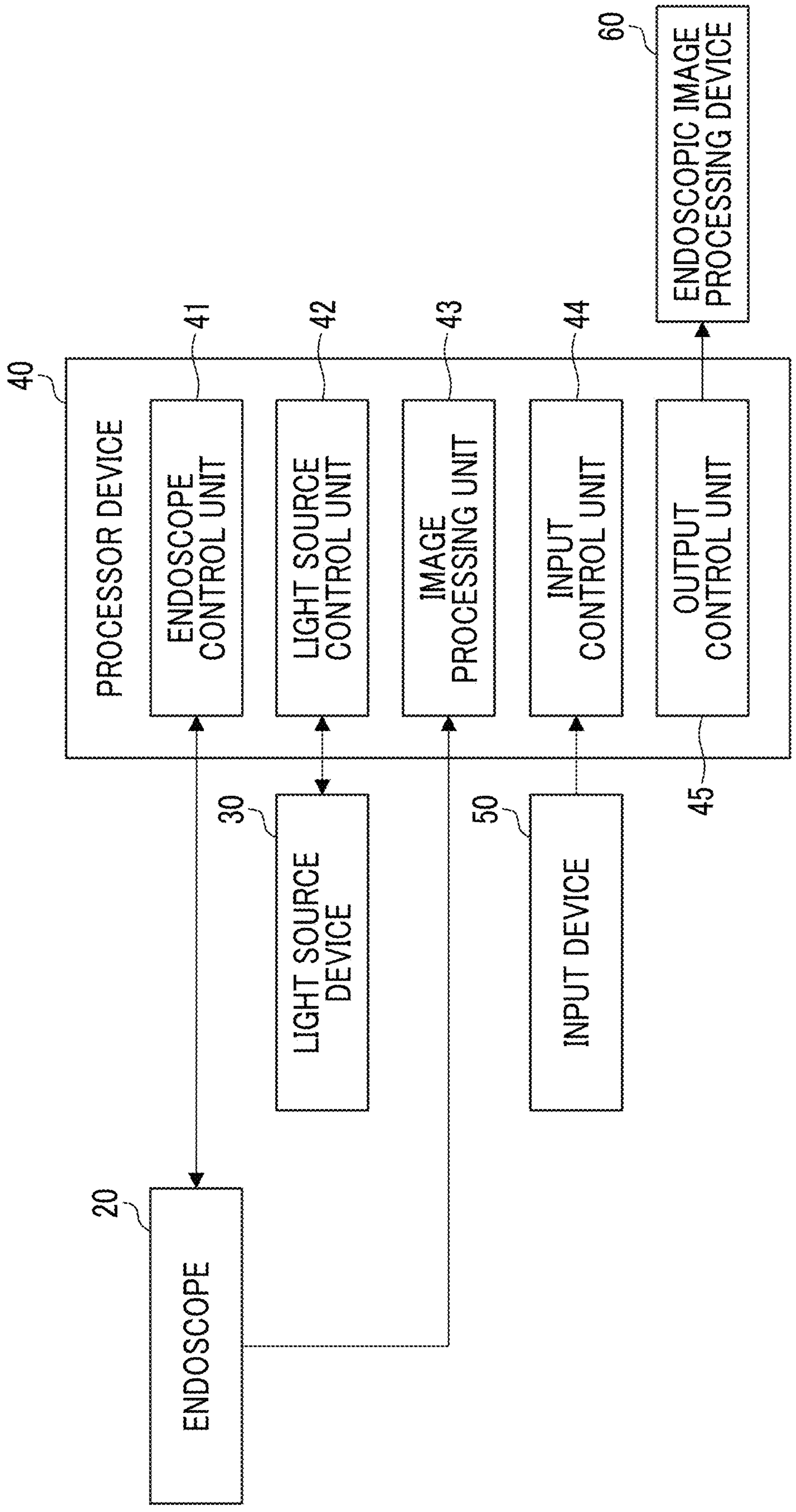
FIG. 6 is a block diagram of main functions of a processor device.

FIG. 6 is a block diagram of main functions of the processor device.

As illustrated in the figure, the processor device 40 has functions of an endoscope control unit 41, a light source control unit 42, an image processing unit 43, an input control unit 44, an output control unit 45, and the like. Each function is realized by the processor executing a predetermined program. The auxiliary storage unit stores various programs executed by the processor, various kinds of data necessary for control, and the like.

The endoscope control unit 41 controls the endoscope 20. The control for the endoscope 20 includes image sensor drive control, air/water supply control, suction control, and the like.

The light source control unit 42 controls the light source device 30. The control for the light source device 30 includes light emission control for a light source, and the like.

The image processing unit 43 performs various kinds of signal processing on signals output from the image sensor of the endoscope 20 to generate a captured image (endoscopic image).

The input control unit 44 accepts an input of an operation and an input of various kinds of information via the input device 50.

The output control unit 45 controls an output of information to the endoscopic image processing device 60. The information to be output to the endoscopic image processing device 60 includes various kinds of operation information input from the input device 50, and the like in addition to the endoscopic image obtained by imaging.

[Input Device]

Figure 7:
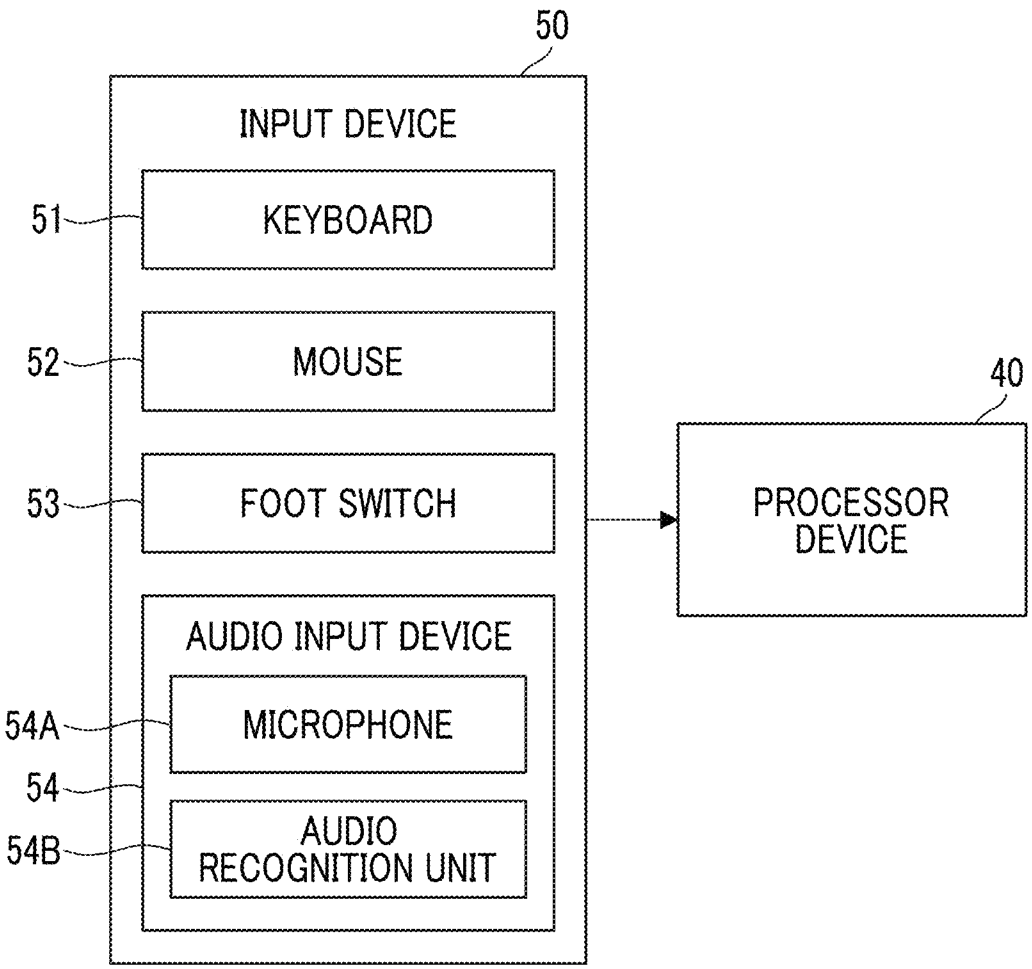
FIG. 7 is a diagram illustrating a schematic configuration of an input device.

FIG. 7 is a diagram illustrating a schematic configuration of the input device.

The input device 50 constitutes a user interface in the endoscope system 10 together with the display device 70. For example, the input device 50 is configured by a keyboard 51, a mouse 52, a foot switch 53, an audio input device 54, and the like. The foot switch 53 is an operation device that is placed at the feet of the operator and that is operated with the foot. The foot switch 53 outputs a predetermined operation signal in a case of stepping on a pedal. The foot switch 53 is an example of a switch. The audio input device 54 includes a microphone 54A, an audio recognition unit 54B, and the like. The audio input device 54 recognizes the audio that has been input from the microphone 54A, using the audio recognition unit 54B to output the audio. For example, the audio recognition unit 54B recognizes the input audio as a word on the basis of a registered dictionary. Since the audio recognition technology itself is a well-known, so detailed description thereof will be omitted. Note that the function of the audio recognition unit 54B may be provided in the processor device 40.

The input device 50 can include known input devices such as a touch panel and a gaze input device in addition to the above-described devices.

[Endoscopic Image Processing Device]

The endoscopic image processing device 60 performs processing of outputting the endoscopic image to the display device 70. In addition, the endoscopic image processing device 60 performs various kinds of recognition processing on the endoscopic image as necessary. In addition, the endoscopic image processing device 60 performs processing of outputting the result of the recognition processing to the display device 70. The recognition processing includes processing of detecting a lesion part or the like, discrimination processing for the detected lesion part or the like, processing of detecting a specific region in a hollow organ, processing of detecting a treatment tool, and the like. Moreover, the endoscopic image processing device 60 performs processing of supporting an input of information necessary for creating a report during the examination. In addition, the endoscopic image processing device 60 performs processing of communicating with the endoscope information management system 100, and outputting examination information or the like to the endoscope information management system 100. The endoscopic image processing device 60 is an example of an information processing apparatus.

The endoscopic image processing device 60 includes, as a hardware configuration, a processor, a main storage unit, an auxiliary storage unit, a communication unit, and the like. That is, the endoscopic image processing device 60 has a so-called computer configuration as the hardware configuration. For example, the processor is configured by a CPU and the like. The processor of the endoscopic image processing device 60 is an example of a first processor. For example, the main storage unit is configured by a RAM and the like. For example, the auxiliary storage unit is configured by a flash memory, a hard disk drive, or the like. For example, the communication unit is configured by a communication interface connectable to a network. The endoscopic image processing device 60 is communicably connected to the endoscope information management system 100 via the communication unit.

Figure 8:
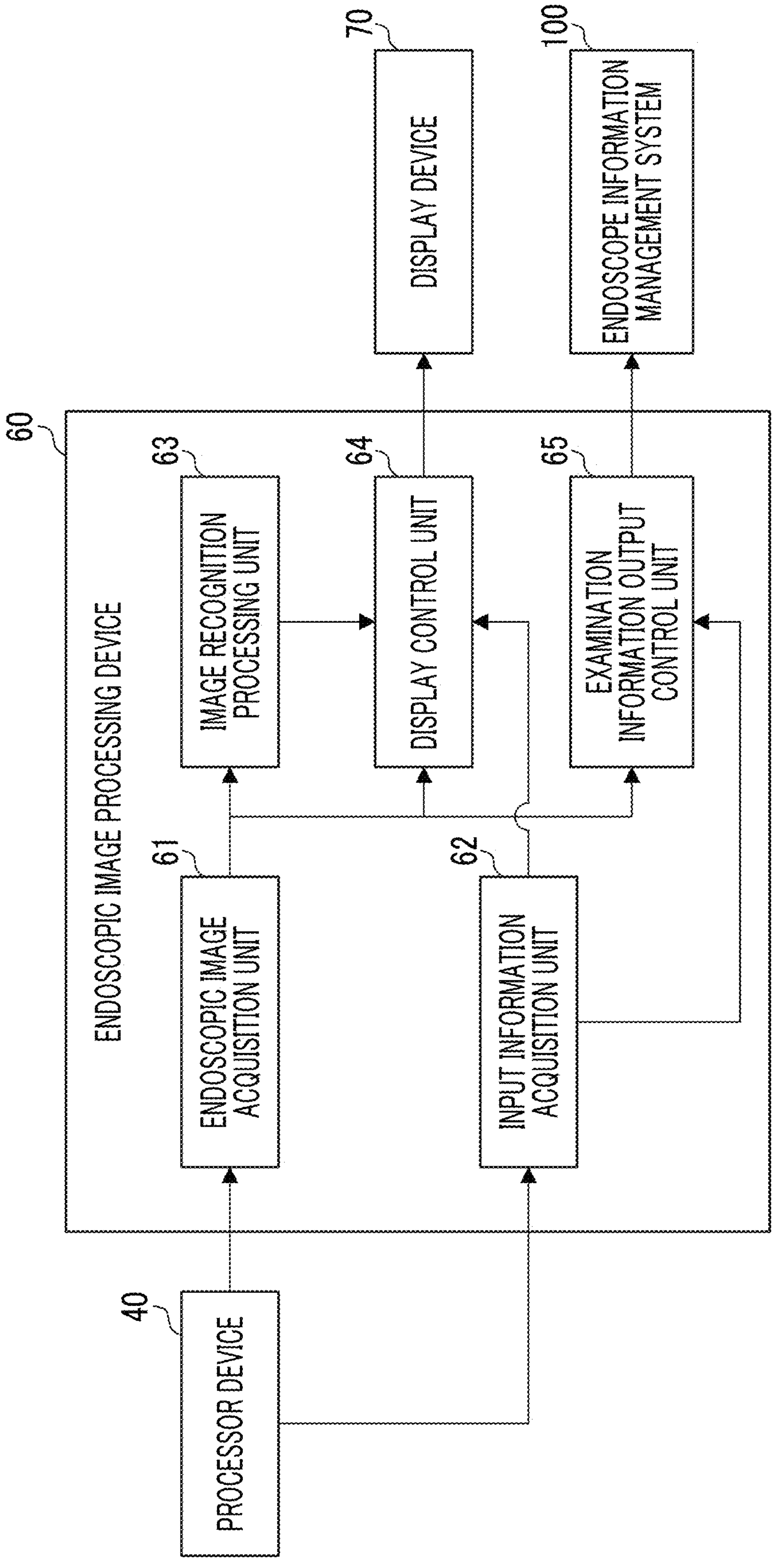
FIG. 8 is a block diagram of main functions of an endoscopic image processing device.

FIG. 8 is a block diagram of main functions of the endoscopic image processing device.

As illustrated in the figure, the endoscopic image processing device 60 mainly has functions of an endoscopic image acquisition unit 61, an input information acquisition unit 62, an image recognition processing unit 63, a display control unit 64, an examination information output control unit 65, and the like. Each function is realized by the processor executing a predetermined program. The auxiliary storage unit stores various programs executed by the processor, various kinds of data necessary for control, and the like.

[Endoscopic Image Acquisition Unit]

The endoscopic image acquisition unit 61 acquires an endoscopic image from the processor device 40. Acquisition of an image is performed in real time. That is, the captured image is acquired in real time.

[Input Information Acquisition Unit]

The input information acquisition unit 62 acquires information input via the input device 50 or the endoscope 20. The information input via the input device 50 includes information input via the keyboard 51, the mouse 52, the foot switch 53, the audio input device 54, or the like. In addition, the information input via the endoscope 20 includes information such as an imaging instruction for a static image. As described below, in the present embodiment, various selection operations are mainly performed via the foot switch 53 and the audio input device 54. The input information acquisition unit 62 acquires the operation information of the foot switch 53 via the processor device 40, and the information on the audio input from the audio input device 54.

[Image Recognition Processing Unit]

The image recognition processing unit 63 performs various kinds of recognition processing on the endoscopic image acquired by the endoscopic image acquisition unit 61. The recognition processing is performed in real time. That is, the recognition processing is performed in real time on the captured image.

Figure 9:
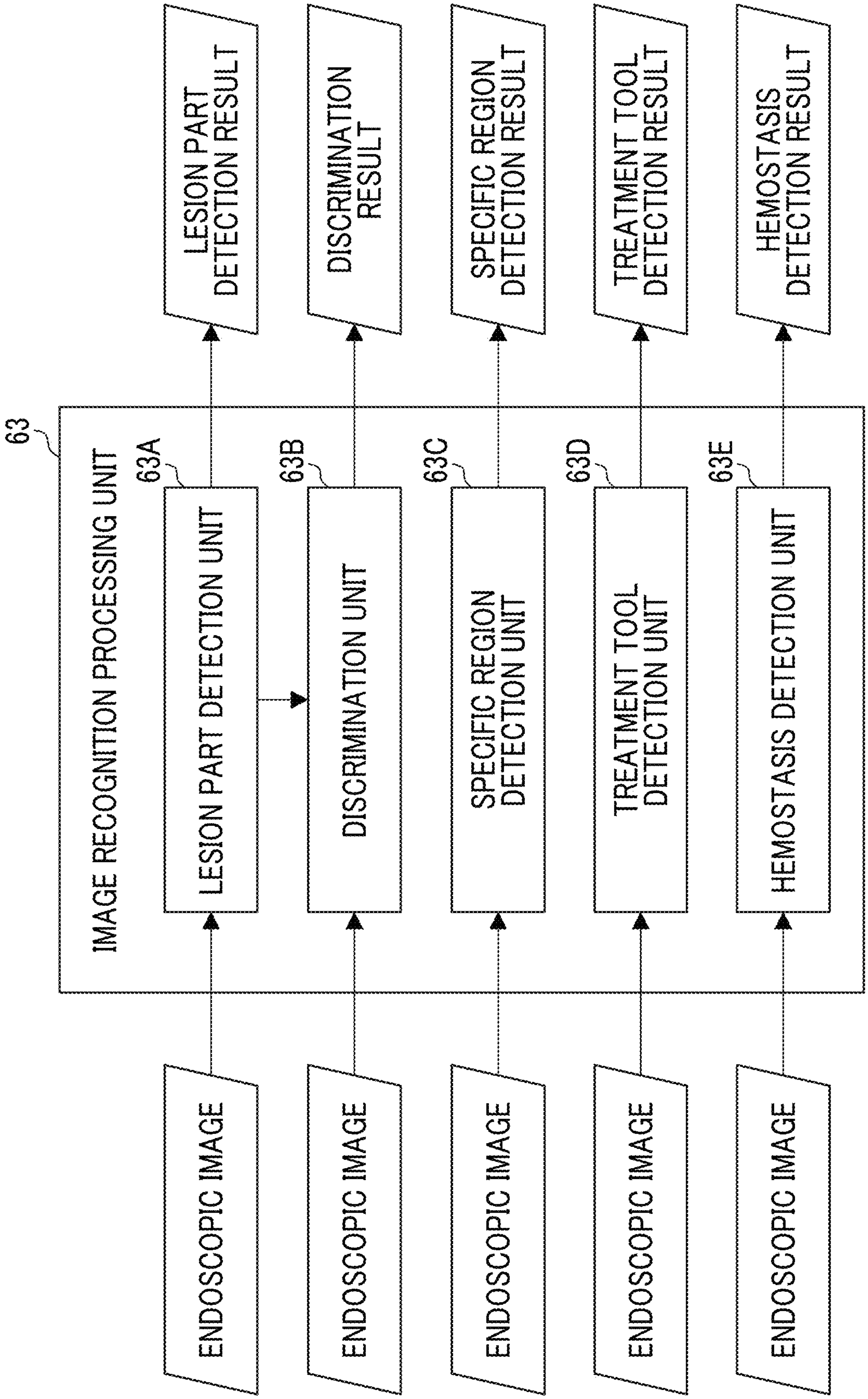
FIG. 9 is a block diagram of main functions of an image recognition processing unit.

FIG. 9 is a block diagram of main functions of the image recognition processing unit.

As illustrated in the figure, the image recognition processing unit 63 has functions of a lesion part detection unit 63A, a discrimination unit 63B, a specific region detection unit 63C, a treatment tool detection unit 63D, a hemostasis detection unit 63E, and the like.

The lesion part detection unit 63A detects a lesion part such as a polyp from the endoscopic image. The processing of detecting the lesion part includes processing of detecting a part with a possibility of a lesion (benign tumor, dysplasia, or the like), processing of recognizing a part with features that may be directly or indirectly associated with a lesion (erythema or the like), and the like in addition to processing of detecting a part that is definitely a lesion part.

The discrimination unit 63B performs the discrimination processing on the lesion part detected by the lesion part detection unit 63A. As an example, in the present embodiment, neoplastic or non-neoplastic (hyperplastic) discrimination processing is performed on the lesion part such as a polyp detected by the lesion part detection unit 63A.

The specific region detection unit 63C performs processing of detecting a specific region in the hollow organ from the endoscopic image. In the present embodiment, processing of detecting an ileocecum of the large intestine is performed. The large intestine is an example of the hollow organ. The ileocecum is an example of the specific region. The specific region detection unit 63C may detect, in addition to the ileocecum, a hepatic flexure (right colon), a splenic flexure (left colon), a rectosigmoid, and the like as the specific region. In addition, the specific region detection unit 63C may detect a plurality of specific regions.

The treatment tool detection unit 63D performs processing of detecting a treatment tool (refer to FIG. 23) appearing in the image from the endoscopic image, and discriminating the type of the treatment tool. For example, the treatment tool is biopsy forceps, a snare, or the like.

The hemostasis detection unit 63E performs processing of detecting a hemostasis treatment tool (refer to FIG. 25) appearing in the image from the endoscopic image and detecting a hemostasis treatment. For example, the hemostasis treatment tool is a hemostatic clip.

Each unit (the lesion part detection unit 63A, the discrimination unit 63B, the specific region detection unit 63C, the treatment tool detection unit 63D, the hemostasis detection unit 63E, and the like) constituting the image recognition processing unit 63 is configured by, for example, artificial intelligence (AI) having a learning function. Specifically, each unit is configured by AI or a trained model trained using deep learning or a machine learning algorithm such as a neural network (NN), a convolutional neural network (CNN), AdaBoost, and random forest.

Note that a part or all of the units constituting the image recognition processing unit 63 can be configured to calculate a feature amount from the image and to perform detection or the like using the calculated feature amount, instead of being configured by AI or the trained model.

Each unit (the lesion part detection unit 63A, the discrimination unit 63B, the specific region detection unit 63C, the treatment tool detection unit 63D, the hemostasis detection unit 63E, and the like) constituting the image recognition processing unit 63 is an example of a plurality of recognizers. The endoscopic image is input to each recognizer, and the recognition processing (detection processing) is performed.

[Display Control Unit]

The display control unit 64 controls display of the display device 70. In the following, main display control performed by the display control unit 64 will be described.

(1) Display of Endoscopic Image or The Like

Figure 10:
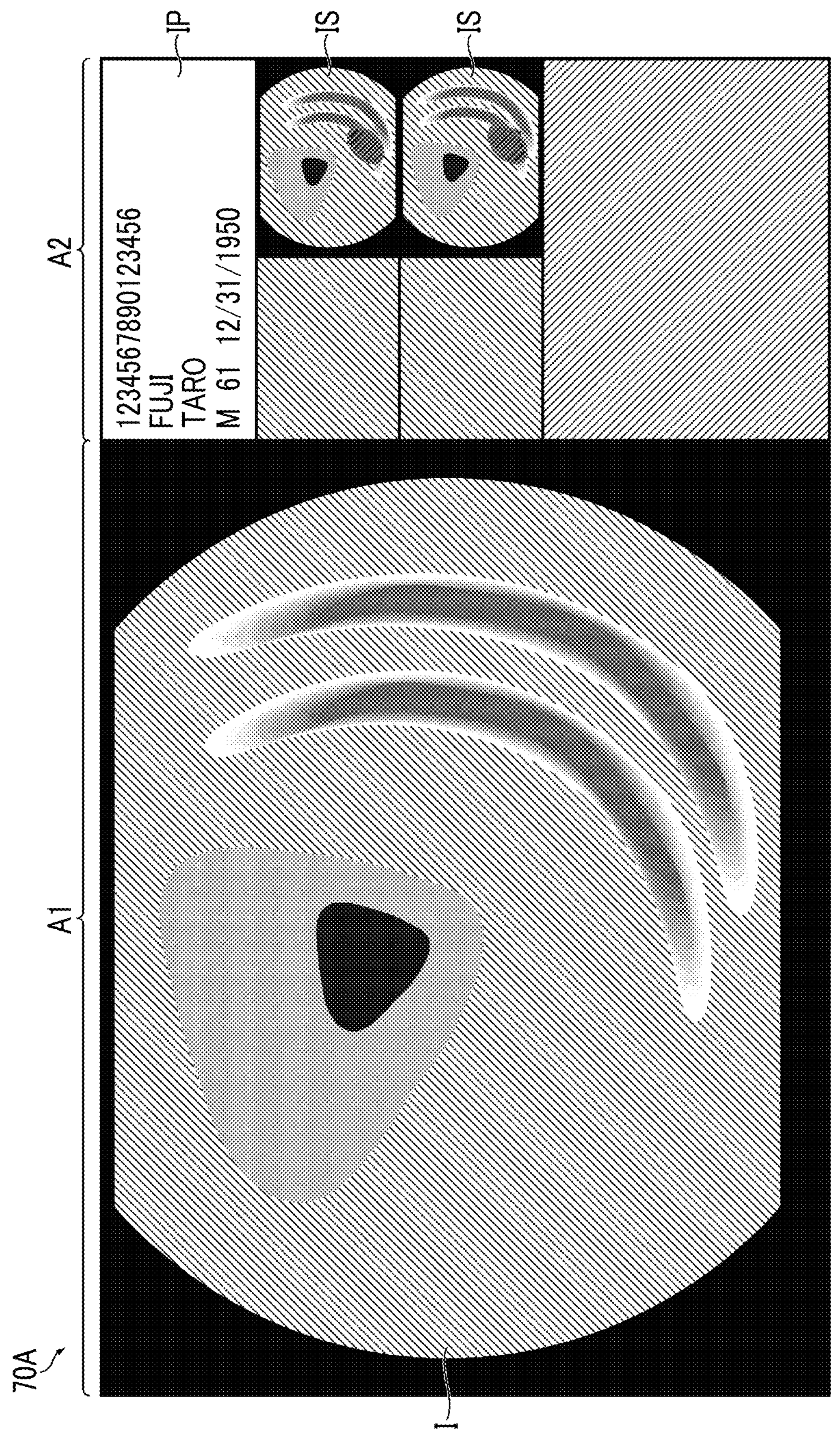
FIG. 10 is a diagram illustrating an example of display of a screen during an examination.

The display control unit 64 displays the image (endoscopic image) captured by the endoscope 20 on the display device 70 in real time during the examination. That is, the endoscopic image is displayed in live view. FIG. 10 is a diagram illustrating an example of display of a screen during the examination. As illustrated in the figure, the endoscopic image I is displayed in a main display region A1 set on a screen 70A. The main display region A1 is an example of a first region. A secondary display region A2 is further set on the screen 70A. Various kinds of information regarding the examination are displayed in the secondary display region A2. In the example illustrated in FIG. 10, a case where information IP regarding a patient and a static image IS of the endoscopic image captured during the examination are displayed in the secondary display region A2 is illustrated. For example, the static images IS are displayed in the captured order from top to bottom of the screen 70A.

Figure 11:
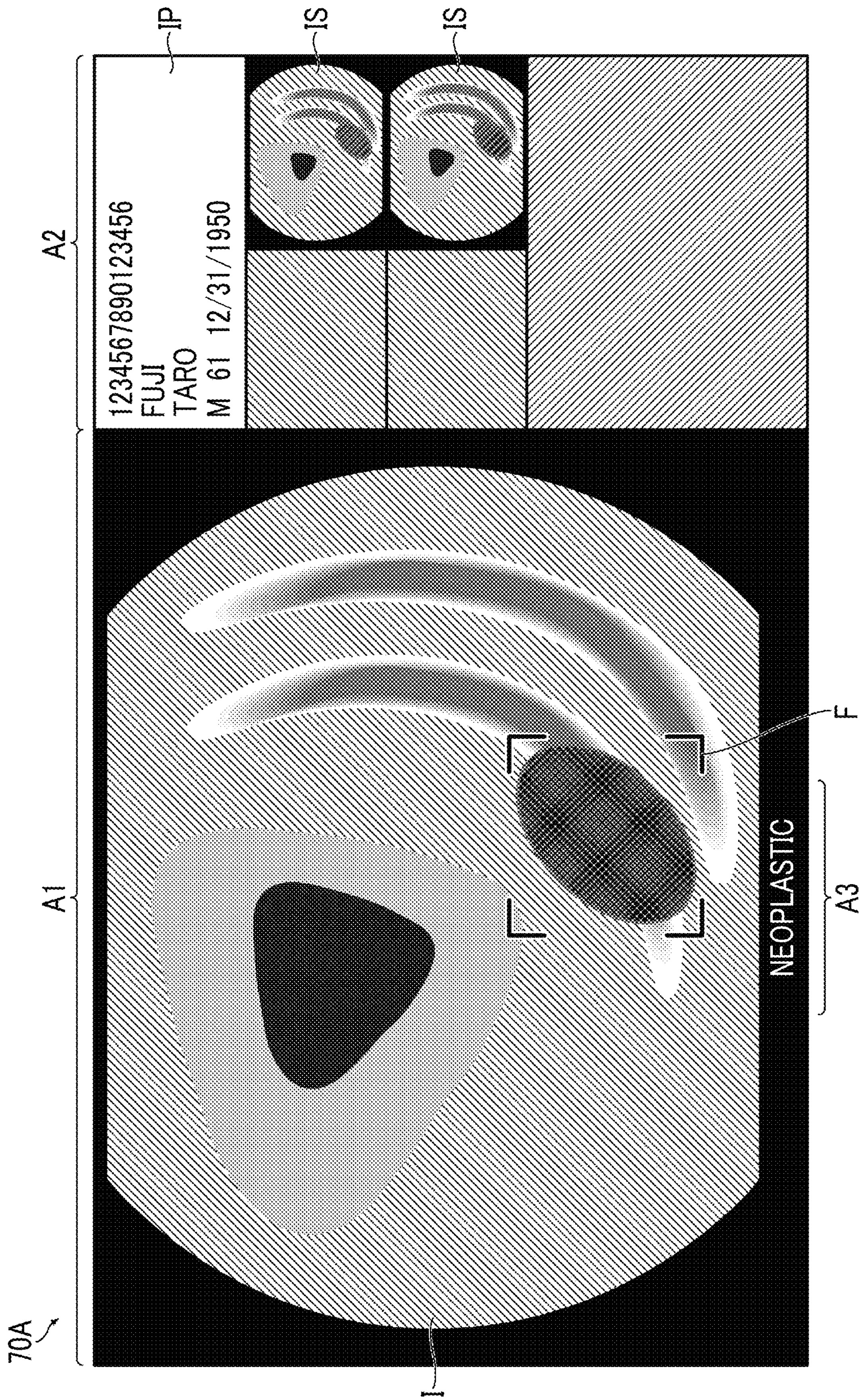
FIG. 11 is a diagram illustrating another example of display of a screen during an examination.

FIG. 11 is a diagram illustrating another example of display of the screen during the examination. The figure illustrates an example of display of a screen in a case where a detection support function for a lesion part is ON.

As illustrated in the figure, in a case where the detection support function for a lesion part is ON, in a case where a lesion part P is detected from the endoscopic image I being displayed, the display control unit 64 displays the endoscopic image I on the screen 70A by enclosing a target region (region of the lesion part P) with a frame F. Moreover, in a case where a discrimination support function is ON, the display control unit 64 displays a discrimination result in a discrimination result display region A3 set on the screen 70A in advance. In the example illustrated in FIG. 11, a case where the discrimination result is "NEOPLASTIC" is illustrated.

(2) Display of Site Selection Box

Figure 14:
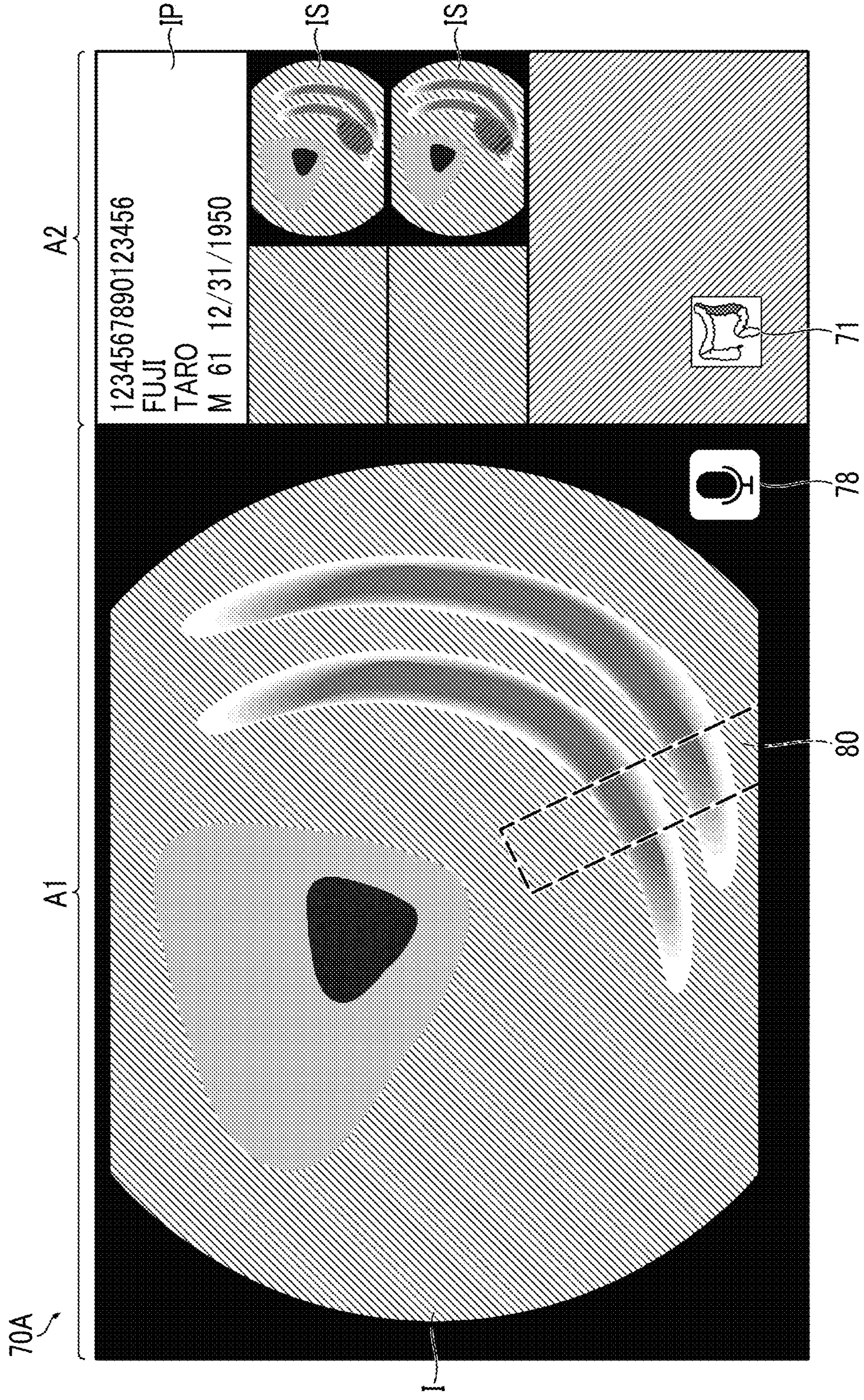
FIG. 14 is a diagram illustrating an example of a display position of a site selection box.

The display control unit 64 displays a site selection box 71 on the screen 70A with the fact that a specific condition is satisfied as a trigger (refer to FIG. 14). The site selection box 71 is a region for selecting a site under examination, on the screen. The site selection box 71 constitutes an interface for inputting a site on the screen. In the present embodiment, in a case where a specific region is detected by the specific region detection unit 63C, the site selection box 71 is displayed. That is, the site selection box 71 is displayed on the screen with the detection of the specific region by the specific region detection unit 63C as a trigger. The specific region detection unit 63C is an example of a first recognizer.

The display control unit 64 detects that the specific region detection unit 63C has detected the specific region to display the site selection box 71 at a predetermined position on the screen. As described above, the specific region is an ileocecum. Therefore, the display control unit 64 detects that the specific region detection unit 63C has detected the ileocecum to display the site selection box 71 at a predetermined position on the screen.

Figure 12:
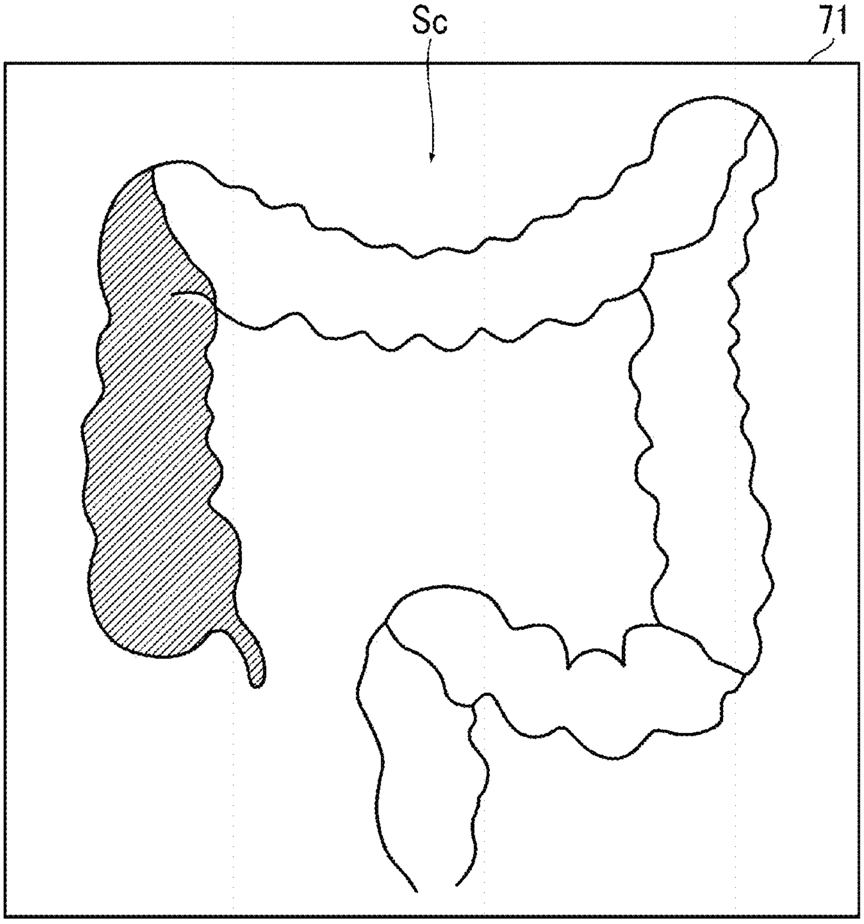
FIG. 12 is a diagram illustrating an example of a site selection box.

FIG. 12 is a diagram illustrating an example of the site selection box.

As illustrated in the figure, the site selection box 71 of the present embodiment is configured by an image in which a schema diagram Sc of the large intestine is displayed in a rectangular frame. The displayed schema diagram Sc is divided into a plurality of sites, and selection can be made for each divided site. In FIG. 12, an example of a case where the large intestine is selected from three sites is illustrated. Specifically, a case where the large intestine is selected from three sites of "ASCENDING COLON", "TRANSVERSE COLON", and "DESCENDING COLON" is illustrated.

Note that FIG. 12 is an example of division of sites, and it is also possible to divide the sites in more detail. In this case, the selection of the site in more detail becomes possible.

Each item of the "ascending colon", the "transverse colon", and the "descending colon" that are divided in the schema diagram Sc is an example of an option for the item corresponding to the specific region detection unit 63C that is a recognizer.

Figure 13C:
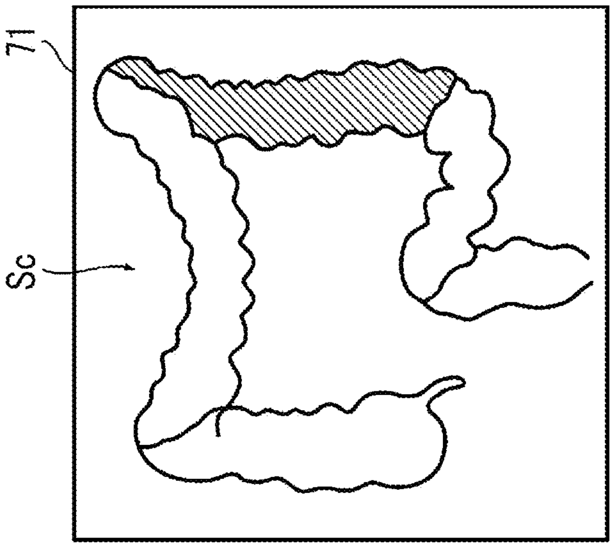
FIGS. 13A to 13C are diagrams illustrating examples of display of a site being selected.
Figure 13B:
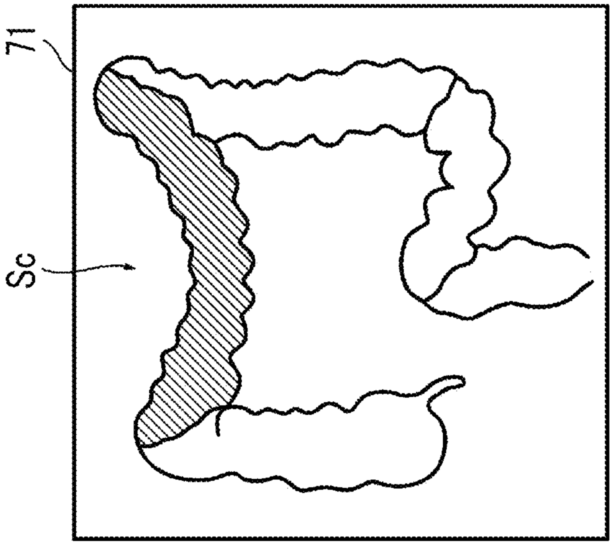
Figure 13A:
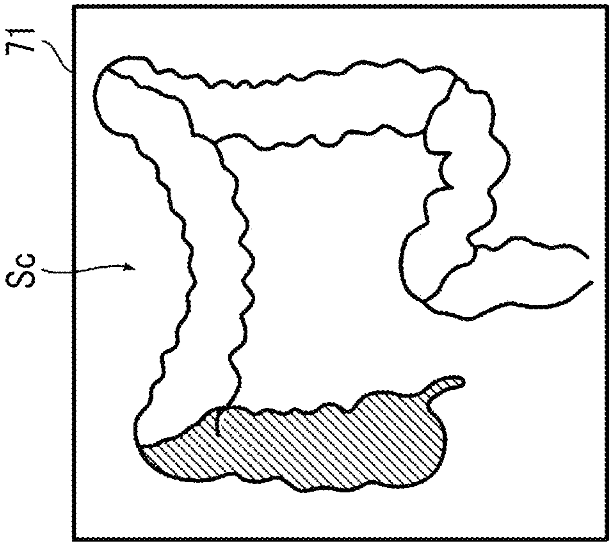

FIGS. 13A to 13C are diagrams illustrating examples of display of the site being selected. FIG. 13A illustrates an example of a case in which the "ascending colon" is selected. FIG. 13B illustrates an example of a case in which the "transverse colon" is selected. FIG. 13C illustrates an example of a case in which the "descending colon" is selected. As illustrated in each diagram of FIGS. 13A to 13C, the selected site is displayed to be distinguishable from the other sites. In the example illustrated in FIGS. 13A to 13C, the selected site is displayed to be distinguishable from the other sites by changing the color of the selected site. In addition, the selected site may be distinguished from the other sites by making the selected site blink or the like.

FIG. 14 is a diagram illustrating an example of a display position of the site selection box. The site selection box 71 is displayed at a fixed position on the screen 70A. The position where the site selection box 71 is displayed is set in the vicinity of the position where the treatment tool 80 appears in the endoscopic image displayed in the main display region A1. As an example, the display position of the site selection box 71 is set to a position that does not overlap the endoscopic image I displayed in the main display region A1 and that is adjacent to the position where the treatment tool 80 appears. The position is a position in substantially the same direction as the direction in which the treatment tool 80 appears, with respect to the center of the endoscopic image I displayed in the main display region A1. In the present embodiment, as illustrated in FIG. 14, the treatment tool 80 is displayed from the lower right position of the endoscopic image I displayed in the main display region A1. Thus, the position where the site selection box 71 is displayed is set to the lower right position with respect to the center of the endoscopic image I displayed in the main display region A1. The region where the site selection box 71 is displayed on the screen 70A is an example of a second region.

Figure 15:
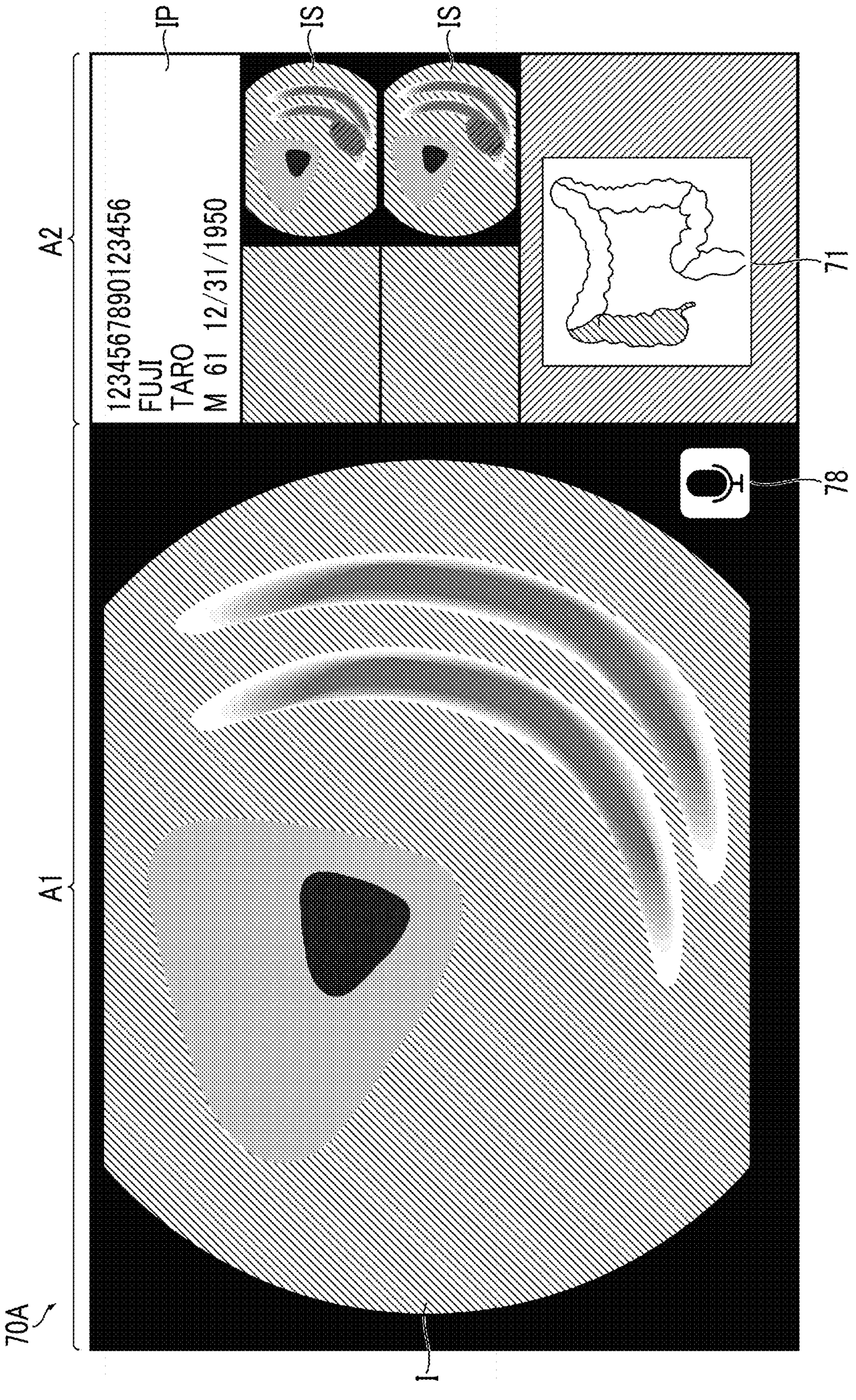
FIG. 15 is a diagram illustrating an example of emphasized display of a site selection box.

In a case where the site is selected, the display control unit 64 displays the site selection box 71 in an emphasized manner for a fixed time (time T1). Time T1 is determined in advance. Time T1 may be arbitrarily set by a user. FIG. 15 is a diagram illustrating an example of emphasized display of the site selection box. As illustrated in the figure, in the present embodiment, the site selection box 71 is displayed in an emphasized manner by being enlarged. In addition, as the emphasizing method, methods such as changing a color from a normal display form, enclosing with a frame, and blinking, and a method of a combination thereof can be adopted. The method of selecting the site will be described below.

In a case where the site selection box 71 is displayed on the screen 70A for the first time, the display control unit 64 displays the site selection box 71 on the screen 70A in a state where a specific site is selected in advance. The site selected in advance is a site to which the specific region belongs. In the present embodiment, the specific region is an ileocecum. The site to which the ileocecum belongs is the ascending colon. Therefore, the display control unit 64 displays the site selection box 71 on the screen in a state where the ascending colon is selected (refer to FIG. 13A).

In addition, for example, in a case where the hepatic flexure is the specific region, the site selection box 71 is displayed on the screen in a state where the transverse colon is selected. In addition, in a case where the splenic flexure is the specific region, the site selection box 71 is displayed on the screen in a state where the descending colon is selected.

In this manner, in the endoscope system 10 of the present embodiment, the site selection box 71 is displayed on the screen in a state where a specific site is selected in advance. In general, the operator ascertains the position of the distal end portion 21A of the endoscope 20 from an insertion length of the endoscope, the image during the examination, the feel during operation in the endoscope operation, and the like. In a case where the site selected in advance is correct, the site selection operation by the user is not necessary. Accordingly, it is possible to save the time and effort for the site selection, and it is possible to efficiently input the information on the site.

Note that after the display starts in a state where a specific site is selected in advance, in the present embodiment, the site selection box 71 is displayed in an emphasized manner for a fixed time from the display start (refer to FIG. 15). Accordingly, it is possible to easily recognize that a site is selected, and to easily check the selected site.

(3) Display of Diagnosis Name Selection Box

The display control unit 64 displays a diagnosis name selection box 72 on the screen 70A with the fact that a specific condition is satisfied as a trigger. The diagnosis name selection box 72 is a region for selecting a diagnosis name on the screen. The diagnosis name selection box 72 constitutes an interface for inputting the diagnosis name on the screen. In the present embodiment, in a case where a discrimination result for the detected lesion part is output, the diagnosis name selection box 72 is displayed. That is, the diagnosis name selection box 72 is displayed with the output of the discrimination result as a trigger. The display control unit 64 detects that the discrimination unit 63B has output the discrimination result, and displays the diagnosis name selection box 72 at a predetermined position on the screen. Note that, as described above, the discrimination processing is executed in a case where the discrimination support function is ON. Therefore, the display control unit 64 displays the diagnosis name selection box 72 only in a case where the discrimination support function is ON.

FIG. 16 is a diagram illustrating an example of the diagnosis name selection box.

As illustrated in the figures, the diagnosis name selection box 72 is configured by a so-called list box, and selectable diagnosis names are displayed in a list. In the example illustrated in FIG. 16, an example of a case in which selectable diagnosis names are displayed in a list in a vertical line is illustrated. The diagnosis names corresponding to the hollow organ as the examination target are displayed. In the present embodiment, since the examination targets the large intestine, the diagnosis names corresponding to the examination of the large intestine are displayed in a list in the diagnosis name selection box 72.

Note that the diagnosis names displayed in a list in the diagnosis name selection box 72 do not have to be all the diagnosis names that can be diagnosed. It is preferable to limit the number of diagnosis names to a smaller number. That is, it is preferable to limit the number to a specified number or less. In this case, the diagnosis names that are frequently diagnosed are chosen and displayed. Alternatively, the diagnosis names chosen by the user are displayed.

In the example illustrated in FIG. 16, "tumor", "serrated lesion", "familial adenomatous polyposis", "ulcerative colitis", "colon polyp", "hyperplastic polyp", "juvenile polyp", and "inflammatory polyp" are displayed in a list. In FIG. 16, a treatment name displayed in white characters on a black background indicates the diagnosis name being selected. In the example illustrated in FIG. 16, a case where "tumor" is selected is illustrated.

In a case where the diagnosis name selection box 72 is displayed on the screen, the display control unit 64 arranges the diagnosis names in a predetermined order and displays the diagnosis name selection box 72 on the screen. In this case, it is preferable to display the diagnosis names in order of frequency of selection.

Each diagnosis name displayed in a list in the diagnosis name selection box 72 is an example of an option for the item corresponding to the discrimination unit 63B that is a recognizer.

Figure 17:
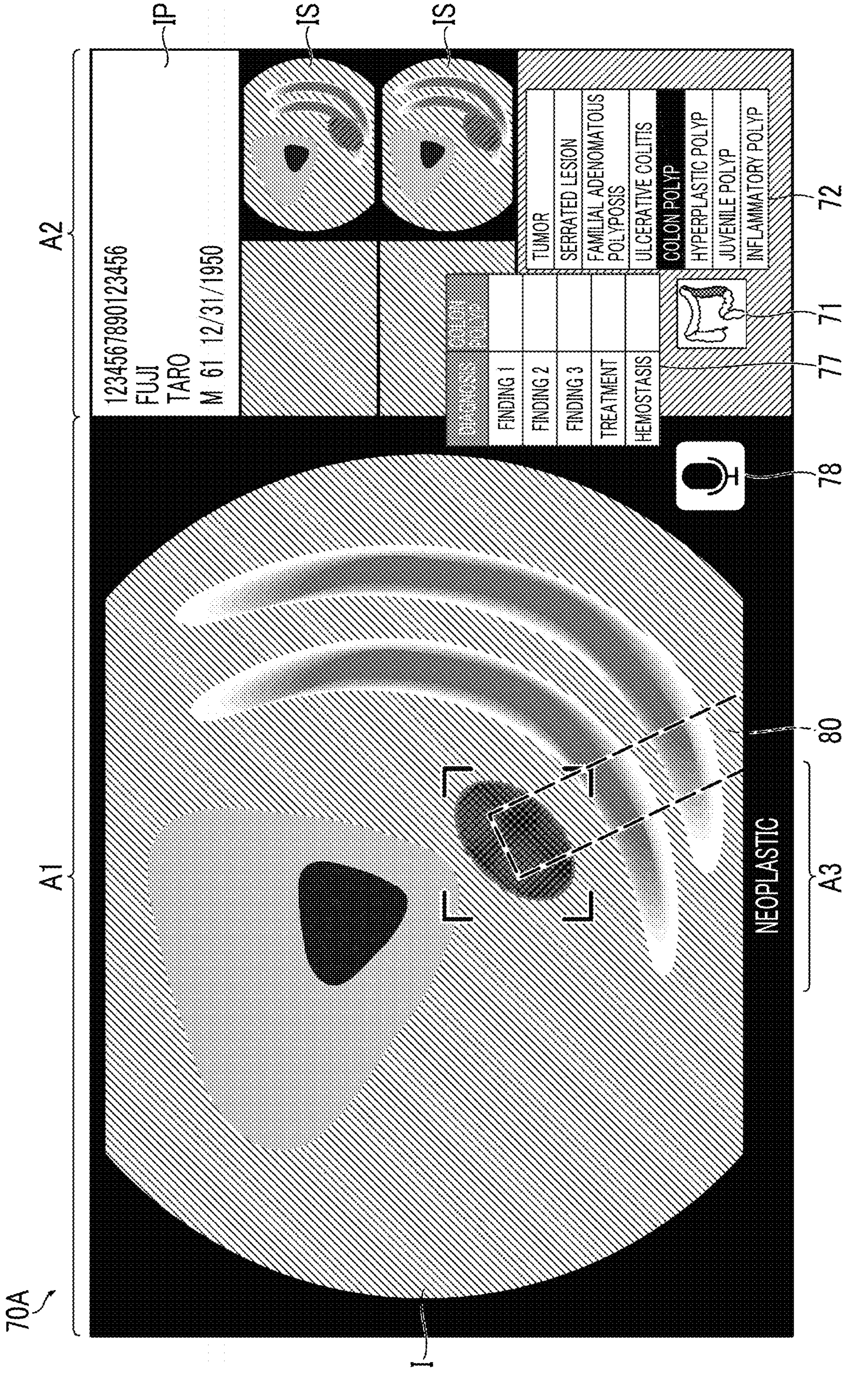
FIG. 17 is a diagram illustrating an example of a display position of a diagnosis name selection box.

FIG. 17 is a diagram illustrating an example of the display position of the diagnosis name selection box. The diagnosis name selection box 72 is displayed at a fixed position on the screen 70A. More specifically, the diagnosis name selection box 72 is displayed as a pop-up at a fixed position. In the present embodiment, as illustrated in FIG. 17, the diagnosis name selection box 72 is displayed in the vicinity of the site selection box 71. Therefore, the diagnosis name selection box 72 is displayed in the vicinity of the position where the treatment tool appears in the endoscopic image I. In this manner, by displaying the diagnosis name selection box 72 in the vicinity of the position where the treatment tool 80 appears in the endoscopic image I, it is easier for the user to recognize the presence of the diagnosis name selection box 72. That is, it is possible to improve visibility. The region where the diagnosis name selection box 72 is displayed on the screen is another example of the second region.

The user selects a diagnosis name while the diagnosis name selection box 72 is being displayed on the screen to input the diagnosis name. The selection method will be described later.

(4) Display of Findings Selection Box

In a case where a diagnosis name is selected in the diagnosis name selection box 72 so that a diagnosis name is input, the display control unit 64 displays a findings selection box on the screen 70A instead of the diagnosis name selection box 72. The findings selection box is a region for selecting an item for the findings on the screen. The findings selection box constitutes an interface for inputting the findings on the screen. In the present embodiment, after a fixed time has elapsed after the diagnosis name is input, the findings selection box is displayed. That is, even in a case where the diagnosis name is input, the display is not switched immediately, but the display is switched after a fixed time has elapsed. Since the display is switched after a fixed time has elapsed, it is possible to secure time to check the item of the selected findings.

Note that, as described above, the diagnosis name selection box 72 is displayed on the screen in a case where a predetermined discrimination result is output from the discrimination unit 63B. Then, instead of the diagnosis name selection box 72, findings selection boxes 73A to 73C are displayed on the screen in a case where the selection processing of the diagnosis name is performed in the diagnosis name selection box 72. Therefore, the selection boxes displayed on the screen in a case where a predetermined discrimination result is output from the discrimination unit 63B are the diagnosis name selection box 72 and the findings selection boxes 73A to 73C. The discrimination unit 63B is an example of a second recognizer.

Figure 18A:
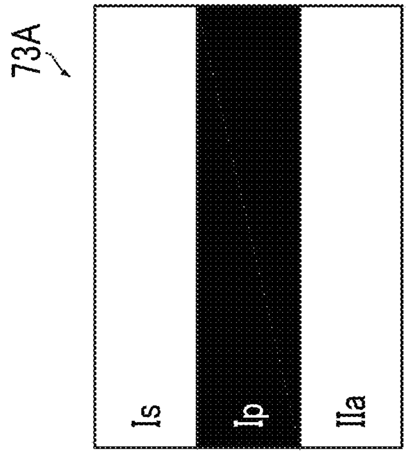
FIGS. 18A to 18C are diagrams illustrating examples of a findings selection box.
Figure 18B:
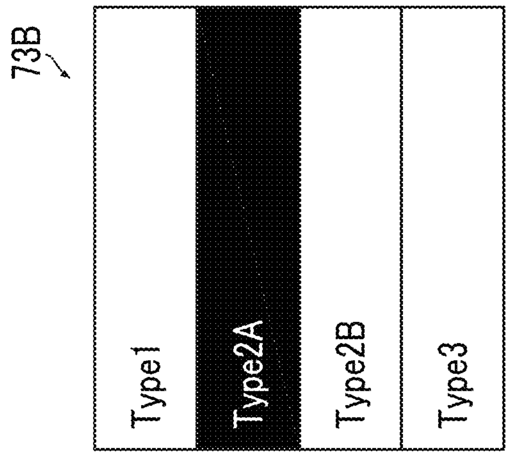
Figure 18C:
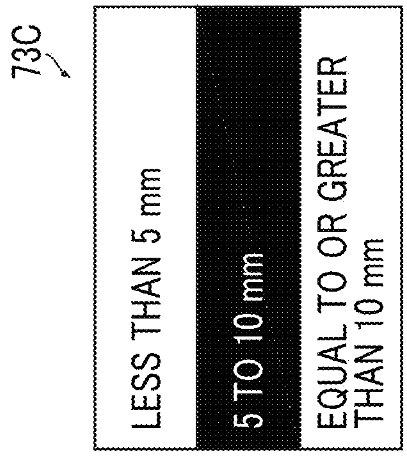

FIGS. 18A to 18C are diagrams illustrating examples of the findings selection box.

FIGS. 18A to 18C illustrate examples of a case of inputting the findings regarding a plurality of items. In this case, the selection box is prepared for each item. In the examples illustrated in FIGS. 18A to 18C, a case of inputting the findings for the classification of a lesion part is illustrated. Specifically, FIG. 18A illustrates an example of the findings selection box 73A for inputting the findings for a macroscopic classification. FIG. 18B illustrates an example of the findings selection box 73B for inputting the findings for a Japan NBI Expert Team (JNET) classification. FIG. 18C illustrates an example of the findings selection box 73C for inputting the findings for a size classification. The findings selection boxes 73A to 73C are configured by a so-called list box, and selectable classifications are displayed in a list.

The macroscopic classification illustrated in FIG. 18A illustrates an example of a case where the options are "Is", "Ip", and "IIa". As illustrated in the figure, the options for the macroscopic classification are displayed in a list. Note that "Is" indicates a sessile type, "Ip" indicates a pedunculated type, and "IIa" indicates a superficial type. In FIG. 18A, the classification displayed in white characters on a black background indicates the classification being selected. In the example illustrated in FIG. 18A, a case where "Ip" is selected is illustrated.

The JNET classification illustrated in FIG. 18A illustrates an example of a case where the options are "Type 1", "Type 2A", Type 2B", and "Type 3". As illustrated in the figure, the options for the JNET classification are displayed in a list. Note that "Type 1" indicates a hyperplastic polyp or a sessile serrated lesion (SSL), "Type 2A" indicates an adenoma or a low-grade cancer (pTis cancer), "Type 2B" indicates a high-grade cancer (pTis cancer or pT1a cancer), and "Type 3" indicates a high-grade cancer (pT1b cancer) or an advanced cancer. In FIG. 18B, the classification displayed in white characters on a black background indicates the classification being selected. In the example illustrated in FIG. 18B, a case where "Type 2A" is selected is illustrated.

The size classification illustrated in FIG. 18C illustrates an example of a case where the options are "less than 5 mm", "5 to 10 mm", and "equal to or greater than 10 mm". As illustrated in the figure, the options for the size classification are displayed in a list. Note that, in FIG. 18C, the classification displayed in white characters on a black background indicates the classification being selected. In the example illustrated in FIG. 18C, a case where "5 to 10 mm" is selected is illustrated.

In each item, the classifications to be displayed in a list do not necessarily have to be all classifications. It is possible to select and display only the classifications that are input frequently.

In a case where the findings selection boxes 73A to 73C are displayed on the screen, the display control unit 64 arranges the options in a predetermined order and displays the findings selection boxes 73A to 73C on the screen. In this case, it is preferable to display the options in order of frequency of selection.

The options displayed in a list in the findings selection boxes 73A to 73C are other examples of options for the item corresponding to the discrimination unit 63B that is a recognizer.

Figure 19:
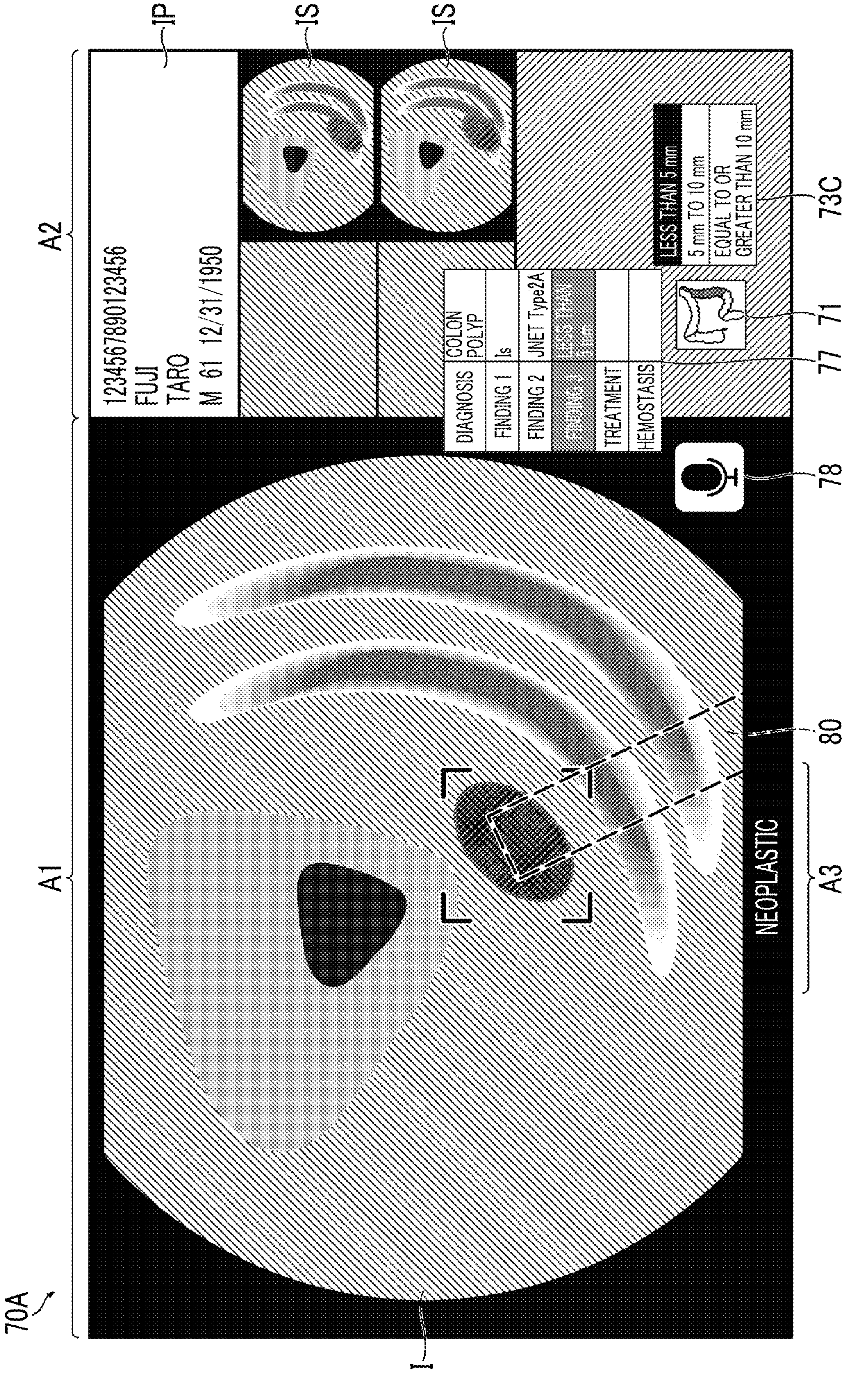
FIG. 19 is a diagram illustrating an example of a display position of a findings selection box.

FIG. 19 is a diagram illustrating an example of a display position of the findings selection box. FIG. 19 illustrates an example of a case of displaying the findings selection box 73C for the size classification.

As described above, the findings selection box is displayed on the screen by being switched from the diagnosis name selection box 72. Therefore, the findings selection box is displayed at the same position as the diagnosis name selection box 72.

In a case where a plurality of findings selection boxes are prepared as in the present embodiment, the findings selection boxes are displayed in order. That is, each time the user performs the selection operation, the display is switched in a predetermined order. As an example, in the present embodiment, the findings selection boxes 73A to 73C are displayed in the order of the macroscopic classification, the JNET classification, and the size classification. The order of the display may be arbitrarily set by the user.

The display is switched after a fixed time has elapsed after the user's selection operation. Accordingly, it is possible to check the selected classification on the screen.

The method of selecting the classification in the findings selection boxes 73A to 73C displayed on the screen will be described later.

(5) Display of Treatment Tool Detection Mark

Figure 20A:
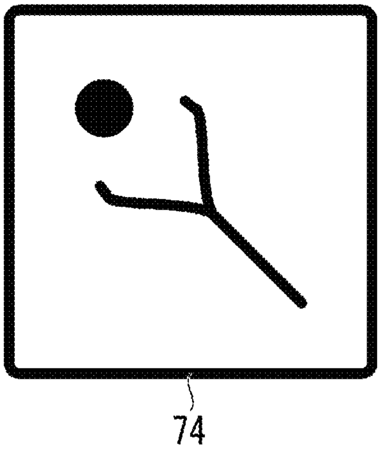
FIGS. 20A and 20B are diagrams illustrating examples of a treatment tool detection mark.
Figure 20B:
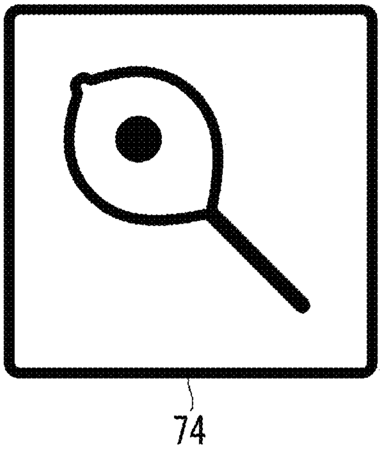

In a case where the treatment tool is detected, the display control unit 64 displays a mark indicating detection of the treatment tool (treatment tool detection mark) on the screen 70A. FIGS. 20A and 20B are diagrams illustrating examples of the treatment tool detection mark. As illustrated in the figures, different marks are used for the detected treatment tools, respectively. FIG. 20A is a diagram illustrating an example of a treatment tool detection mark 74 displayed in a case where biopsy forceps are detected. FIG. 20B is a diagram illustrating an example of the treatment tool detection mark 74 displayed in a case where a snare is detected. A symbol depicting the corresponding treatment tool is used as the treatment tool detection mark in each figure. In addition, the treatment tool detection mark can be represented by characters, figures, and the like.

Figure 23:
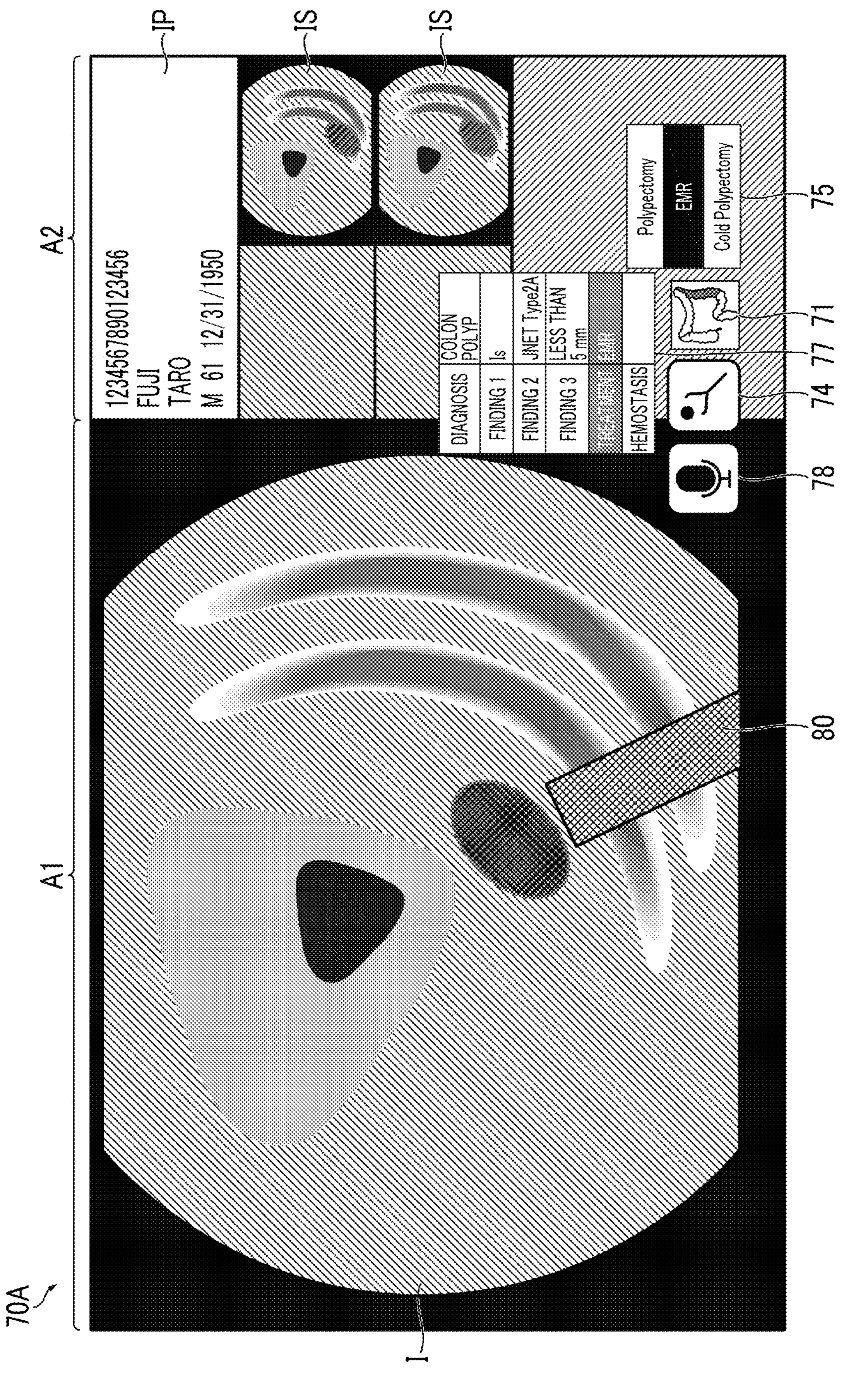
FIG. 23 is a diagram illustrating an example of a display position of a treatment name selection box.

The treatment tool detection mark 74 is displayed at a fixed position on the screen 70A. The position where the treatment tool detection mark 74 is displayed is set in the vicinity of the position where the treatment tool 80 appears in the endoscopic image I displayed in the main display region A1. As an example, the position is set to a position that does not overlap the endoscopic image I displayed in the main display region A1 and that is adjacent to the position where the treatment tool 80 appears. The position is a position in substantially the same direction as the direction in which the treatment tool 80 appears, with respect to the center of the endoscopic image I displayed in the main display region A1. In the present embodiment, as illustrated in FIG. 23, the treatment tool 80 is displayed from the lower right position of the endoscopic image I displayed in the main display region A1. Thus, the position where the treatment tool detection mark 74 is displayed is set to the lower right position with respect to the center of the endoscopic image I displayed in the main display region A1. In a case where the site selection box 71 is simultaneously displayed, the treatment tool detection mark 74 is displayed side by side with the site selection box 71. In this case, the treatment tool detection mark 74 is displayed at a position closer to the treatment tool 80 than the site selection box 71. In the example illustrated in FIG. 23, the treatment tool detection mark 74 is displayed on the left side of the site selection box 71.

In this manner, by displaying the treatment tool detection mark 74 in the vicinity of the position where the treatment tool 80 appears in the endoscopic image I, the user can easily recognize that the treatment tool 80 has been detected (recognized) from the endoscopic image I. That is, it is possible to improve visibility.

(6) Display of Treatment Name Selection Box

In a case where a specific condition is satisfied, the display control unit 64 displays a treatment name selection box 75 on the screen 70A. The treatment name selection box 75 is a region for selecting a treatment name (a specimen collection method in a case of specimen collection) on the screen. The treatment name selection box 75 constitutes an interface for inputting the treatment name on the screen. In the present embodiment, the treatment name selection box 75 is displayed in a case where the treatment tool is detected from the endoscopic image by the treatment tool detection unit 63D. That is, the treatment name selection box 75 is displayed on the screen with the detection of the treatment tool by the treatment tool detection unit 63D as a trigger. The treatment tool detection unit 63D is an example of a third recognizer.

The display control unit 64 detects that the treatment tool detection unit 63D has detected the treatment tool to display the treatment name selection box 75 at a predetermined position on the screen. The treatment name selection box 75 is displayed on the screen at least while the treatment tool is being detected.

Figure 21A:
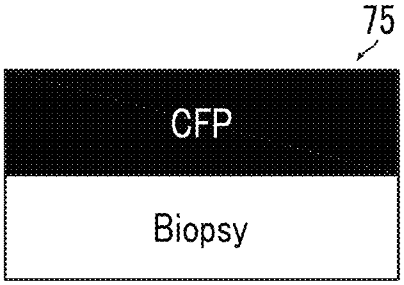
FIGS. 21A and 21B are diagrams illustrating examples of a treatment name selection box.
Figure 21B:
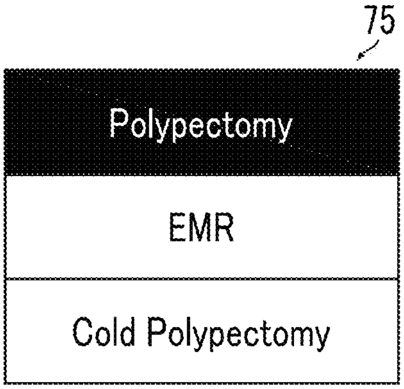

FIGS. 21A and 21B are diagrams illustrating examples of the treatment name selection box.

As illustrated in the figures, the treatment name selection box 75 is configured by a so-called list box, and selectable treatment names are displayed in a list. In the example illustrated in FIGS. 21A and 21B, an example of a case in which selectable treatment names are displayed in a list in a vertical line is illustrated.

In the treatment name selection box 75, the name corresponding to the treatment tool 80 detected from the endoscopic image I is displayed. FIG. 21A illustrates an example of the treatment name selection box 75 displayed on the screen in a case where the treatment tool 80 detected from the endoscopic image I is the "biopsy forceps". As illustrated in the figure, in a case where the detected treatment tool is the "biopsy forceps", "cold forceps polypectomy (CFP)" and "Biopsy" are displayed as the selectable treatment names. FIG. 21B illustrates an example of the treatment name selection box 75 displayed on the screen in a case where the treatment tool 80 detected from the endoscopic image I is the "snare". As illustrated in the figure, in a case where the detected treatment tool is the "snare", "Polypectomy", "endoscopic mucosal resection (EMR)", and "Cold Polypectomy" are displayed as the selectable treatment names.

In FIGS. 21A and 21B, a treatment name displayed in white characters on a black background indicates the treatment name being selected. In the example illustrated in FIG. 21A, a case where "CFP" is selected is illustrated. Further, in the example illustrated in FIG. 21B, a case where "Polypectomy" is selected is illustrated.

In a case where the treatment name selection box 75 is displayed on the screen, the display control unit 64 displays the treatment name selection box 75 on the screen in a state where a specific treatment name is selected in advance. In addition, in a case where the treatment name selection box 75 is displayed on the screen, the display control unit 64 displays the treatment names in a predetermined arrangement in the treatment name selection box 75. Therefore, the display control unit 64 controls the display of the treatment name selection box 75 by referring to the table.

FIG. 22 is a diagram illustrating an example of the table.

As illustrated in the figure, in the table, pieces of information on "treatment tool", "treatment name to be displayed", "display rank", and "default option" are registered in association with each other. Here, the "treatment tool" in the same table is the type of the treatment tool to be detected from the endoscopic image I. The "treatment name to be displayed" is the treatment name to be displayed corresponding to the treatment tool. The "display rank" is a display order of each treatment name to be displayed. In a case where the treatment names are displayed in a vertical line, the treatment names are ranked 1, 2, 3, and the like from the top. The "default option" is the treatment name that is first selected.

The "treatment name to be displayed" may not necessarily be the treatment names of all the treatments executable by the corresponding treatment tool. It is preferable to limit the number of diagnosis names to a smaller number. That is, it is preferable to limit the number to a specified number or less. In this case, in a case where the number of types of treatments executable by a certain treatment tool exceeds a specified number, the number of treatment names to be registered in the table (treatment names displayed in the treatment name selection box) is limited to a specified number or less.

In a case where the number of treatment names to be displayed is limited, a treatment name with a high execution frequency is chosen from among the treatment names of the executable treatments. For example, in a case where the "treatment tool" is the "snare", (1) "Polypectomy", (2) "EMR", (3) "Cold Polypectomy", (4) "EMR [en bloc]", (5) "EMR [piecemeal: <5 pieces]", (6) "EMR [piecemeal: ≥5 pieces]", (7) "endoscopic submucosal resection with a ligation device (ESMR-L)", (8) "endoscopic mucosal resection using a cap-fitted endoscope (EMR-C)", and the like are exemplified as the treatment names of executable treatments. It is assumed that (1) "Polypectomy", (2) "EMR", (3) "Cold Polypectomy", (4) "EMR [en bloc]", (5) "EMR [piecemeal: <5 pieces]", (6) "EMR [piecemeal: ≥5 pieces]", (7) "ESMR-L", and (8) "EMR-C" are arranged in the descending order of the execution frequency, and the specified number is three. In this case, three of (1) Polypectomy, (2) EMR, and (3) Cold Polypectomy are registered in the table as the "treatment name to be displayed". Note that each of (4) "EMR [en bloc]", (5) "EMR [piecemeal: <5 pieces]", and (6) "EMR [piecemeal: ≥5 pieces]" is a treatment name in a case of inputting a detailed treatment name by EMR. (4) EMR [en bloc] is a treatment name in a case of the en bloc resection by EMR. (5) EMR [piecemeal: <5 pieces] is a treatment name in a case of the piecemeal resection by EMR with less than 5 pieces. (6) EMR [piecemeal: ≥5 pieces] is a treatment name in a case of the piecemeal resection by EMR with 5 pieces or more.

The specified number can be determined for each treatment tool. For example, the number (specified number) of treatment names to be displayed for each treatment tool can be determined such that the specified number is two for the "biopsy forceps" and the specified number is three for the "snare". For the "biopsy forceps", for example, "Hot Biopsy" is exemplified as the executable treatment in addition to the "CFP" and the "Biopsy".

In this manner, by narrowing down the treatment names with a high execution frequency (treatment names having a high probability of being selected) and displaying the options (selectable treatment names) in the treatment name selection box 75, the user can efficiently select the treatment name. In a case where a plurality of treatments can be executed by the same treatment tool, the detection of the treatment (treatment name) executed by the treatment tool may be more difficult than the detection of the type of the treatment tool (image recognition). By associating the treatment name that may be executed with the treatment tool in advance and allowing the operator to select the treatment name, it is possible to select an appropriate treatment name with a small number of operations.

The "display rank" is ranked 1, 2, 3, and the like in the descending order of the execution frequency. Normally, the higher the execution frequency is, the higher the selection frequency is, so the descending order of the execution frequency is synonymous with the descending order of the selection frequency.

In the "default option", the treatment name with the highest execution frequency among the treatment names to be displayed is selected. The highest execution frequency is synonymous with the highest selection frequency.

In the example illustrated in FIG. 22, in a case where the "treatment tool" is the "biopsy forceps", the "treatment name to be displayed" is "CFP" and "Biopsy". Then, the "display rank" is in the order of "CFP" and "Biopsy" from the top, and the "default option" is "CFP" (refer to FIG. 21A).

In addition, in a case where the "treatment tool" is the "snare", the "treatment name to be displayed" is "Polypectomy", "EMR", and "Cold Polypectomy". Then, the "display rank" is in the order of "Polypectomy", "EMR", and "Cold Polypectomy" from the top, and the "default option" is "Polypectomy" (refer to FIG. 21B).

The display control unit 64 chooses treatment names to be displayed in the treatment name selection box 75 by referring to the table on the basis of the information on the treatment tool detected by the treatment tool detection unit 63D. Then, the treatment name selection box 75 is displayed on the screen in a manner that the chosen treatment names are arranged according to the information on the display rank registered in the table. The treatment name selection box 75 is displayed on the screen in a state where one treatment name is selected according to the information on the default option registered in the table. In this manner, by displaying the treatment name selection box 75 in a state where a specific treatment name is selected in advance, in a case where there is no need to change, it is possible to save time and effort for the selection. Accordingly, it is possible to efficiently input information on the treatment name. In addition, by setting the treatment name selected in advance as the treatment name of the treatment with a high execution frequency (=treatment with a high selection frequency), it is possible to save time and effort for the change. In addition, by arranging the treatment names to be displayed in the treatment name selection box 75 in the descending order of the execution frequency (=descending order of selection frequency), the user can efficiently select the treatment name. Moreover, by narrowing down and displaying the options, the user can efficiently select the treatment name. The display content and the display order of the treatment name can be set for each hospital (including examination facility) and for each device. In addition, the default option may be set to the treatment name of the treatment previously executed during the examination. Since the same treatment may be repeated during the examination, it is possible to save time and effort for the change by selecting the previous treatment name as the default.

FIG. 23 is a diagram illustrating an example of the display position of the treatment name selection box. The treatment name selection box 75 is displayed at a fixed position on the screen 70A. More specifically, the treatment name selection box 75 is displayed as a pop-up at a fixed position. In the present embodiment, the treatment name selection box 75 is displayed in the vicinity of the treatment tool detection mark 74. More specifically, the treatment name selection box 75 is displayed adjacent to the treatment tool detection mark 74. In the example illustrated in FIG. 23, an example of a case of displaying the treatment name selection box 75 adjacent to an upper right portion of the treatment tool detection mark 74 is illustrated. Since the treatment name selection box 75 is displayed adjacent to the treatment tool detection mark 74, the treatment name selection box 75 is displayed in the vicinity of the position where the treatment tool appears in the endoscopic image I. In this manner, by displaying the treatment name selection box 75 in the vicinity of the position where the treatment tool 80 appears in the endoscopic image I, it is easier for the user to recognize the presence of the treatment name selection box 75. That is, it is possible to improve visibility. The region where the treatment name selection box 75 is displayed on the screen is another example of the second region.

Note that FIG. 23 illustrates a display example in a case where the "biopsy forceps" are detected as the treatment tool. In this case, the treatment name selection box 75 corresponding to the "biopsy forceps" is displayed (refer to FIG. 21A).

As described above, the treatment name selection box 75 is continuously displayed at least while the treatment tool is being detected from the endoscopic image. The selection of the treatment name is continuously accepted while the treatment name selection box 75 is being displayed. Therefore, during the display of the treatment name selection box 75, the treatment name once selected can be corrected. In a case where the treatment name selection box 75 disappears from the screen, the selection is confirmed. That is, the treatment name that is selected immediately before disappearing from the screen is confirmed as the selected treatment name. The display control unit 64 causes the treatment name selection box 75 to disappear from the screen after a fixed time has elapsed from the disappearance of the treatment tool from the endoscopic image.

(7) Display of Hemostasis Selection Box

In a case where a specific condition is satisfied, the display control unit 64 displays a hemostasis selection box 76 on the screen 70A. In the present embodiment, the hemostasis selection box 76 is a region for selecting the number of hemostasis treatment tools (for example, hemostatic clip) on the screen. The hemostasis selection box 76 constitutes an interface for inputting the number of hemostasis treatment tools on the screen. In the present embodiment, in a case where a hemostasis treatment tool 81 is detected from the endoscopic image, the hemostasis selection box 76 is displayed (refer to FIG. 25). That is, the hemostasis selection box 76 is displayed with the detection of the hemostasis treatment tool 81 by the hemostasis detection unit 63E as a trigger. The display control unit 64 detects that the hemostasis detection unit 63E has detected the hemostasis treatment tool 81 to display the hemostasis selection box 76 at a predetermined position on the screen. The hemostasis detection unit 63E is an example of a fourth recognizer. The hemostasis selection box 76 is displayed on the screen while the hemostasis treatment tool 81 is being detected.

Figure 24:
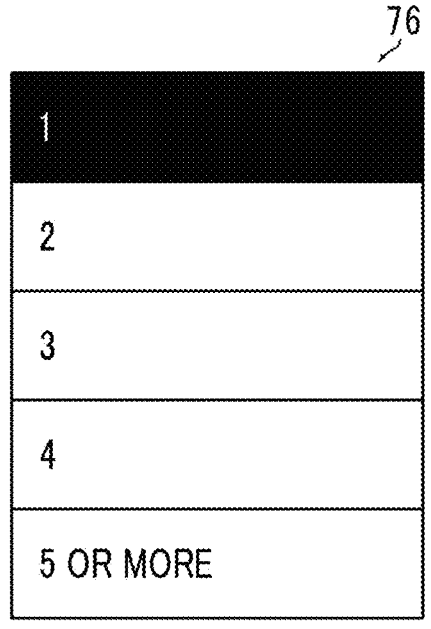
FIG. 24 is a diagram illustrating an example of a hemostasis selection box.

FIG. 24 is a diagram illustrating an example of the hemostasis selection box.

As illustrated in the figures, the hemostasis selection box 76 is configured by a so-called list box, and the numbers of selectable hemostasis treatment tools are displayed in a list. In the example illustrated in FIG. 24, an example of a case in which the numbers of selectable hemostasis treatment tools are displayed in a list in a vertical line is illustrated. In particular, FIG. 24 illustrates an example of a case of selecting from among “1”, “2”, “3”, “4”, and “5 or more”. In the example illustrated in FIG. 24, the numbers are displayed in an ascending order of number, but the numbers may be arranged in a descending order of number. In addition, the numbers may be displayed in the descending order of selection frequency. In FIG. 24, the item displayed in white characters on a black background indicates the selected item. In the example illustrated in FIG. 24, a case where “1” is selected is illustrated.

In a case where the hemostasis selection box 76 is displayed on the screen, the display control unit 64 displays the hemostasis selection box 76 in a state where a specific option is selected in advance. The option selected in advance is, for example, the option positioned at the top of the list.

The number of hemostasis treatment tools displayed in the hemostasis selection box 76 is an example of an option for the item corresponding to the hemostasis detection unit 63E that is a recognizer.

Figure 25:
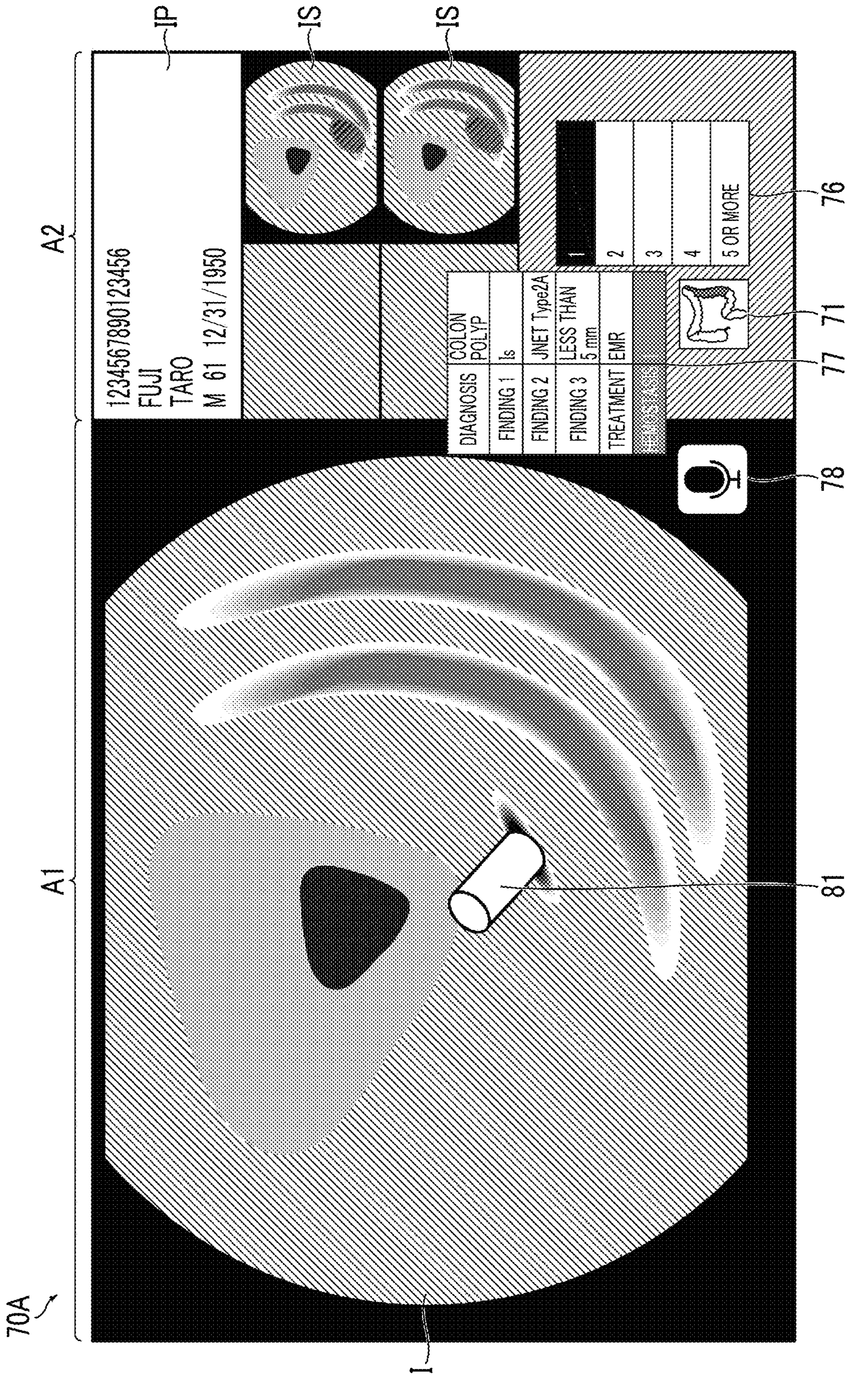
FIG. 25 is a diagram illustrating an example of a display position of a hemostasis selection box.

FIG. 25 is a diagram illustrating an example of a display position of the hemostasis selection box. The hemostasis selection box 76 is displayed at a fixed position on the screen 70A. More specifically, the hemostasis selection box 76 is displayed as a pop-up at a fixed position. In the present embodiment, as illustrated in FIG. 25, the hemostasis selection box 76 is displayed in the vicinity of the site selection box 71. Therefore, the hemostasis selection box 76 is displayed in the vicinity of the position where the treatment tool appears in the endoscopic image I. In this manner, by displaying the hemostasis selection box 76 in the vicinity of the position where the treatment tool 80 appears in the endoscopic image I, it is easier for the user to recognize the presence of the hemostasis selection box 76. That is, it is possible to improve visibility. The region where the hemostasis selection box 76 is displayed on the screen is another example of the second region.

The user selects an option while the hemostasis selection box 76 is being displayed on the screen to input the number of hemostasis treatment tools. The selection method will be described later.

(8) Display of Input Information Display Box

In a case where the user inputs predetermined information using each selection box of the diagnosis name selection box 72, the findings selection boxes 73A to 73C, the treatment name selection box 75, and the hemostasis selection box 76, the display control unit 64 displays an input information display box 77 on the screen 70A. The input information display box 77 is a region for displaying the information input by the user.

FIG. 26 is a diagram illustrating an example of the input information display box.

As illustrated in the figure, in the input information display box 77, pieces of the information on the options selected in the selection boxes are displayed in a list within a rectangular frame. In FIG. 26, in the first row in the frame, information on the option selected in the diagnosis name selection box 72 is displayed. In the second row in the frame, information on the option selected in the findings selection box 73A for the macroscopic classification is displayed. In the third row in the frame, information on the option selected in the findings selection box 73B for the JNET classification is displayed. In the fourth row in the frame, information on the option selected in the findings selection box 73C for the size classification is displayed. In the fifth row in the frame, information on the option selected in the treatment name selection box 75 is displayed. In the sixth row in the frame, information on the option selected in the hemostasis selection box 76 is displayed. FIG. 26 illustrates an example of a case where “colon polyp” is selected in the diagnosis name selection box 72, “Is” is selected in the findings selection box 73A for the macroscopic classification, “Type 2A” is selected in the findings selection box 73B for the JNET classification, “less than 5 mm” is selected in the findings selection box 73C for the size classification, “EMR” is selected in the treatment name selection box 75, and “1” is selected in the hemostasis selection box 76.

As illustrated in FIGS. 17, 19, 23, and 25, the input information display box 77 is displayed at a fixed position on the screen. The position is set to a position that does not inhibit the display of the endoscopic image I displayed in the main display region A1. In the present embodiment, the input information display box 77 is displayed at a slightly lower position on the right side of the endoscopic image I displayed in the main display region A1.

The input information display box 77 is displayed on the screen 70A in conjunction with the display of each selection box. In addition, the display content of the input information display box is updated each time the user performs the selection processing using each selection box. That is, the information on the corresponding field is displayed each time the user inputs the information.

Figure 27:
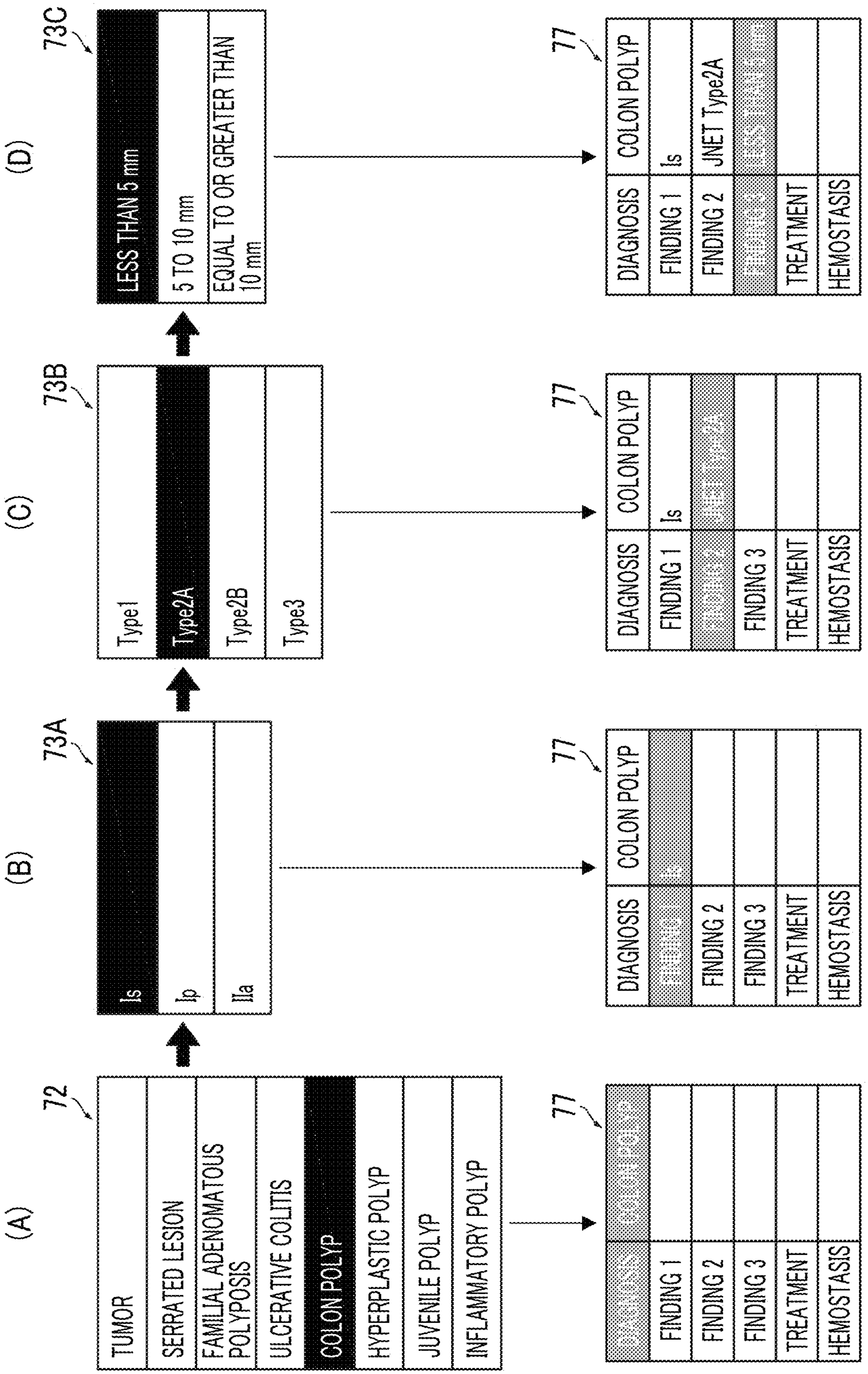
FIG. 27 is a diagram illustrating an example of display transition of an input information display box.

FIG. 27 is a diagram illustrating an example of display transition of the input information display box.

FIG. 27 illustrates the display transition of the input information display box 77 from the selection of the diagnosis name to the selection of the size classification. (A) of FIG. 27 illustrates the display of the input information display box 77 in a case where the diagnosis name is selected. (B) of FIG. 27 illustrates the display of the input information display box 77 in a case where the macroscopic classification is selected. (C) of FIG. 27 illustrates the display of the input information display box 77 in a case where the JNET classification is selected. (D) of FIG. 27 illustrates the display of the input information display box 77 in a case where the size classification is selected.

As illustrated in the figure, each time the selection operation is performed using each selection box, the display of the input information display box 77 is updated. That is, the selected information is displayed in the corresponding field of the input information display box 77.

The user can check the series of selected information by checking the display of the input information display box 77.

Note that, as illustrated in FIG. 27, in the input information display box 77, the item being selected is displayed to be distinguishable from the other items. In the example illustrated in FIG. 27, the item being selected is distinguished from the other items by being displayed in a reversed manner. In this manner, by displaying the item being selected to be distinguishable from the other items, the item being selected can be easily recognized visually.

(9) Display of Audio Input Mark

As described above, the endoscope system 10 of the present embodiment includes the audio input device 54 as the input device 50, and the option can be selected by audio.

The display control unit 64 displays a predetermined audio input mark 78 on the screen 70A in a case where an audio input is possible (refer to FIG. 25). In the present embodiment, the audio input becomes possible while each selection box of the diagnosis name selection box 72, the findings selection boxes 73A to 73C, the treatment name selection box 75, and the hemostasis selection box 76 is being displayed. In addition, the audio input is also possible during a period in which a site can be selected in the site selection box 71.

As illustrated in FIG. 25, a symbol depicting a microphone is used as the audio input mark 78. The audio input mark 78 is displayed at a fixed position on the screen. In the present embodiment, the audio input mark 78 is displayed on the left side of the treatment tool detection mark 74. The user recognizes that the audio input is possible by checking that the audio input mark 78 is being displayed.

[Selection Operation]

Here, a method of selecting the option in each selection box will be described.

As described above, in the present embodiment, the selection of an option is performed using the foot switch 53 and the audio input device 54.

(1) Selection Operation of Site

The selection of the site can be performed using either the foot switch 53 or the audio input device 54.

(A) Selection Operation using Foot Switch

The selection operation of the site using the foot switch 53 is performed as follows.

In a case where the foot switch is operated in a state where the selection of the site is being accepted, the site being selected is switched in order. In the present embodiment, (1) ascending colon, (2) transverse colon, and (3) descending colon are looped and switched in this order. Therefore, for example, in a case where the foot switch 53 is operated once in a state where the "ascending colon" is being selected, the selected site is switched from the "ascending colon" to the "transverse colon". Similarly, in a case where the foot switch 53 is operated once in a state where the "transverse colon" is being selected, the selected site is switched from the "transverse colon" to the "descending colon". Moreover, in a case where the foot switch 53 is operated once in a state where the "descending colon" is being selected, the selected site is switched from the "descending colon" to the "ascending colon". In this manner, the selected site is switched in order each time the foot switch 53 is operated once.

(B) Selection Operation using Audio Input Device

The selection operation using the audio input device 54 is performed by the user reading out the option of the site toward the microphone 54A in a state where the selection of the site is being accepted. For example, in a case of selecting the "ascending colon", the selection is performed by reading out the "ascending colon". Similarly, in a case of selecting the "transverse colon", the selection is performed by reading out the "transverse colon". In addition, in a case of selecting the "descending colon", the selection is performed by reading out the "descending colon".

The information on the selected site is stored in the main storage unit or the auxiliary storage unit. The information on the selected site can be used to specify which site is imaged in the endoscopic image during the examination. For example, by storing the information on the site selected at a timing of capturing each endoscopic image during the examination in association with each endoscopic image, the site imaged in the endoscopic image can be specified after the examination. The information on the selected site may be stored in association with time information during the examination, and can be stored in association with the information on the lesion or the like detected by the image recognition processing unit 63, the endoscopic image, and the like.

Note that, as described above, since the site selection box 71 is displayed in a state where a specific site is selected in advance, the selection operation is performed in a case of switching the selected site.

(2) Selection Operation of Diagnosis Name and Findings

In the present embodiment, the selection of the diagnosis name and the findings can be performed only by the audio input device 54. In a state where the selection of the diagnosis name is being accepted, the user reads out the option of the diagnosis name displayed in the diagnosis name selection box 72 toward the microphone 54A to select the diagnosis name. In addition, in a state where the selection of the findings is being accepted, the user reads out the option of the findings displayed in the findings selection boxes 73A to 73C toward the microphone 54A to select the option (classification) of the findings.

The information on the selected diagnosis name and findings is stored in the main storage unit or the auxiliary storage unit in association with the information on the site being selected.

(3) Selection Operation of Treatment Name

The selection of the treatment name can be performed by either the foot switch 53 or the audio input device 54.

(A) Selection Operation Using Foot Switch

As in the case of the selection of the site, in a case where the foot switch is operated in a state where the selection of the treatment name is being accepted, the treatment name being selected is switched in order. The switching is performed according to the display rank. Therefore, the treatment names are switched in order from the top. Further, the treatment names are looped and switched. For example, in a case of the treatment name selection box 75 illustrated in FIG. 21A, a selection target is alternately switched between "CFP" and "Biopsy" each time the foot switch 53 is operated once. That is, in a case where the foot switch 53 is operated once in a state where "CFP" is being selected, the selection target is switched to "Biopsy", and in a case where the foot switch 53 is operated once in a state where "Biopsy" is being selected, the selection target is switched to "CFP". In addition, for example, in a case of the treatment name selection box 75 illustrated in FIG. 21B, the selection target is looped and switched in the order of (1) "Polypectomy", (2) "EMR", and (3) "Cold Polypectomy" each time the foot switch 53 is operated once. Specifically, in a case where the foot switch 53 is operated once in a state where the "Polypectomy" is being selected, the selection target is switched to "EMR". In addition, in a case where the foot switch 53 is operated once in a state where "EMR" is being selected, the selection target is switched to "Cold Polypectomy". In addition, in a case where the foot switch 53 is operated once in a state where the "Cold Polypectomy" is being selected, the selection target is switched to "Polypectomy".

The selection target can also have a hierarchical structure. That is, the structure can include a plurality of hierarchies, and a plurality of options can be included in each hierarchy. In a case where the selection target has a hierarchical structure, for example, in a case where the foot switch 53 is operated once in a state where the final row of the options in the displayed hierarchy is being selected, the selection target in the next hierarchy is displayed. In addition, in a case where the foot switch 53 is operated once in a state where the final option in the final hierarchy is reached, the first option in the first hierarchy is selected. In addition, in a case where there is no operation using the foot switch for a fixed time, the hierarchy of the displayed option may be automatically changed.

(B) Selection Operation Using Audio Input Device

The selection operation using the audio input device 54 is performed by the user reading out the option of the treatment name toward the microphone 54A in a state where the selection of the treatment name is being accepted.

The information on the selected treatment name is stored together with the information on the detected treatment tool in the main storage unit or the auxiliary storage unit in association with the information on the site being selected, the information on the selected diagnosis name, and the information on the selected findings.

(4) Selection Operation of Number of Hemostasis Treatment Tools

The selection of the number of hemostasis treatment tools can be performed by either the foot switch 53 or the audio input device 54.

(A) Selection Operation Using Foot Switch

As in the case of the selection of the site, in a case where the foot switch is operated, the option being selected is switched in order. The switching is performed according to the display rank. Therefore, the treatment names are switched in order from the top. Further, the treatment names are looped and switched.

(B) Selection Operation Using Audio Input Device

The selection operation using the audio input device 54 is performed by the user reading out the number exemplified in the option toward the microphone 54A in a state where the selection of the site is being accepted.

The information on the selected number of hemostasis treatment tools is stored in the main storage unit or the auxiliary storage unit in association with the information on the site being selected, the information on the selected diagnosis name, the information on the selected findings, and the information on the selected treatment name.

[Display of Each Selection Box and Acceptance of Selection]

Figure 28:
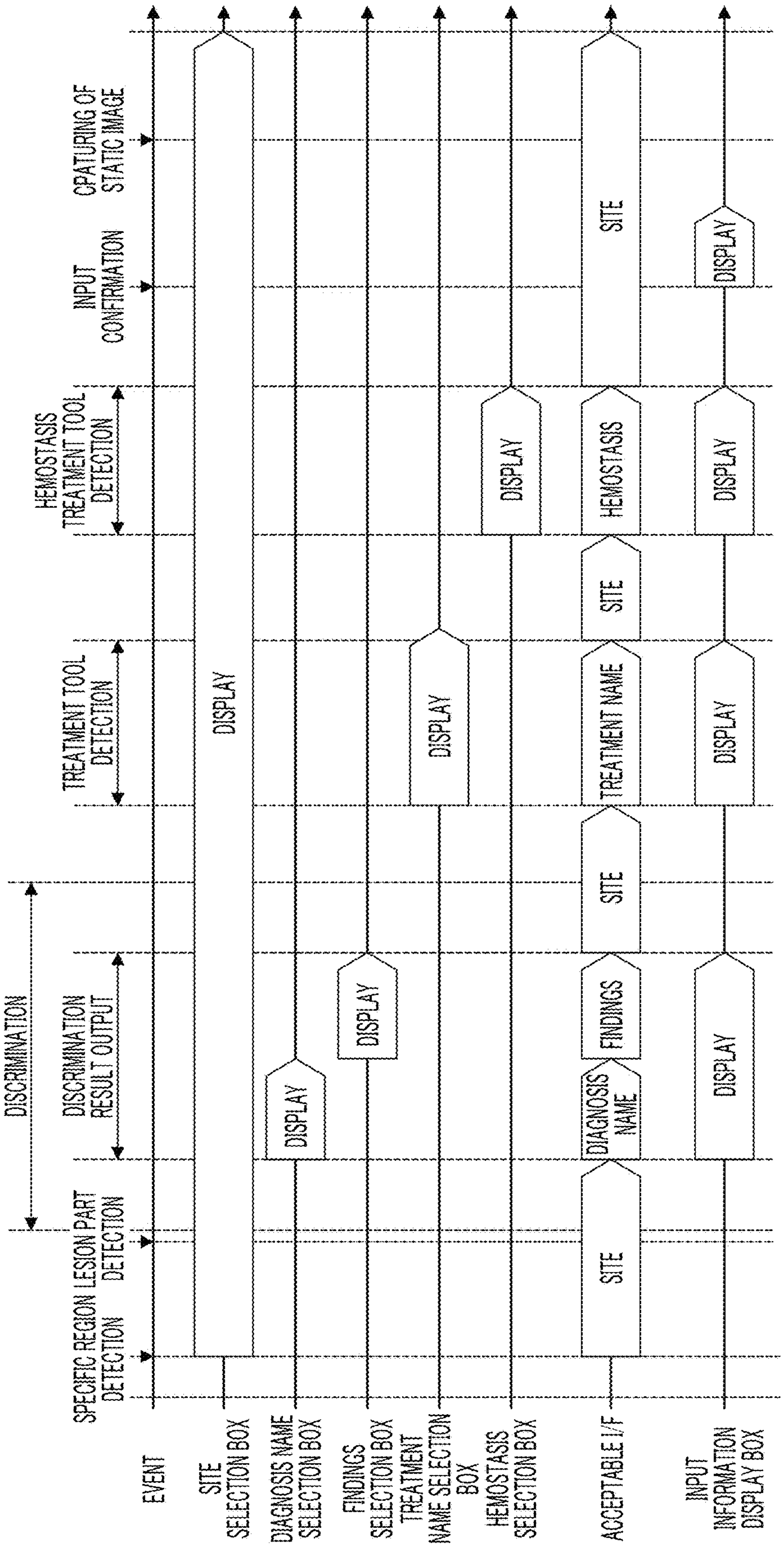
FIG. 28 is a time chart illustrating a relationship between display of each selection box and acceptance of selection.

FIG. 28 is a time chart illustrating a relationship between the display of each selection box and the acceptance of the selection. The figure illustrates an example of a case where a detection support function for a lesion part is ON and a discrimination support function is ON.

First, in a case where a specific region is detected by the specific region detection unit 63C, the site selection box 71 is displayed on the screen with the detection of the specific region as a trigger. In the present embodiment, the specific region is an ileocecum. Thus, in a case where the ileocecum is detected, the site selection box 71 is displayed on the screen. The site selection box 71 is displayed in an emphasized manner for a fixed time from the display start. The site selection box 71 is continuously displayed until the examination ends. In a case where the site selection box 71 is displayed on the screen, the acceptance of the selection of the site starts.

In a case where the lesion part is detected by the lesion part detection unit 63A after the specific region is detected, the discrimination processing is performed on the detected lesion part by the discrimination unit 63B. Here, in a case where a discrimination result is output from the discrimination unit 63B, the diagnosis name selection box 72 is displayed on the screen with the output of the discrimination result as a trigger. By displaying the diagnosis name selection box 72 on the screen, the acceptance of the selection of the site is stopped. Instead, the acceptance of the selection of the diagnosis name starts.

In a case where the selection of the diagnosis name is performed, the findings selection boxes 73A to 73C are displayed on the screen. By displaying the findings selection boxes 73A to 73C on the screen, the acceptance of the selection of the diagnosis name is ended. Instead, the selection for the findings is accepted. Note that, in the present embodiment, since a plurality of items regarding the findings are input, a plurality of findings selection boxes 73A to 73C are switched and displayed in order (refer to FIG. 27). Each of the findings selection boxes 73A to 73C is switched each time the user performs the selection operation. In a case where the selection of the findings is completed, the selection of the site becomes possible again. That is, the acceptance of the selection of the site is resumed.

In a case where the treatment tool is detected by the treatment tool detection unit 63D after the acceptance of the selection of the site is resumed, the treatment name selection box 75 is displayed on the screen with the detection of the treatment tool as a trigger. By displaying the treatment name selection box 75 on the screen, the acceptance of the selection of the site is stopped again. Instead, the acceptance of the selection of the treatment name starts. In a case where the selection of the treatment name is completed, the selection of the site becomes possible again. That is, the acceptance of the selection of the site is resumed.

In a case where the hemostasis treatment tool 81 is detected by the hemostasis detection unit 63E after the acceptance of the selection of the site is resumed, the hemostasis selection box 76 is displayed on the screen with the detection of the hemostasis treatment tool 81 as a trigger. By displaying the hemostasis selection box 76 on the screen, the acceptance of the selection of the site is stopped again. Instead, the acceptance of the selection of the number of hemostasis treatment tools starts. In a case where the selection of the number of hemostasis treatment tools is completed, the selection of the site becomes possible again. That is, the acceptance of the selection of the site is resumed.

As described above, in the present embodiment, each selection box is displayed on the screen with the recognition result by each recognition unit of the image recognition processing unit 63 as a trigger. In this case, the site selection box 71 is continuously displayed on the screen until the examination ends. On the other hand, the selection of the site is limited to a fixed period. That is, the selection of the site is disabled for a period in which the selection is being accepted in other selection boxes. In other words, the selection of the site is possible except the period in which the selection is being accepted in other selection boxes.

[Display of Input Information Display Box]

FIG. 28 also illustrates a display timing of the input information display box 77. As illustrated in the figure, the input information display box 77 is displayed on the screen in conjunction with the display of the diagnosis name selection box 72, the findings selection boxes 73A to 73C, the treatment name selection box 75, and the hemostasis selection box 76. That is, the input information display box 77 is displayed while these selection boxes are being displayed on the screen.

In addition, as illustrated in FIG. 28, the input information display box 77 is displayed on the screen for a fixed period with an input confirmation operation as a trigger. In the present embodiment, the in confirmation operation is performed by, for example, the audio input of a predetermined keyword via the audio input device 54. For example, the keyword is “confirm”. In a case where the user performs the audio input of “confirm”, the input information display box 77 is displayed on the screen. The input information display box 77 displayed here includes the information on all the options selected in the selection boxes. Accordingly, the user can check the series of input information by checking the display of the input information display box 77.

[Examination Information Output Control Unit]

The examination information output control unit 65 outputs the examination information to the endoscope information management system 100. In the examination information, the endoscopic image captured during the examination, the information on the site input during the examination, the information on the treatment name input during the examination, the information on the treatment tool detected during the examination, and the like are included. For example, the examination information is output for each lesion or each time a specimen is collected. In this case, respective pieces of information are output in association with each other. For example, the endoscopic image in which the lesion part or the like is imaged is output in association with the information on the site being selected. Further, in a case where the treatment is performed, the information on the selected treatment name and the information on the detected treatment tool are output in association with the endoscopic image and the information on the site. Further, the endoscopic image captured separately from the lesion part or the like is output to the endoscope information management system 100 in a timely manner. The endoscopic image is output with the information of imaging date and time added.

[Display Device]

The display device 70 is an example of a display unit. For example, the display device 70 includes a liquid-crystal display (LCD), an organic electroluminescence (EL) display (OLED), or the like. In addition, the display device 70 includes a projector, a head-mounted display, and the like. The display device 70 is an example of a first display unit.

[Endoscope Information Management System]

Figure 29:
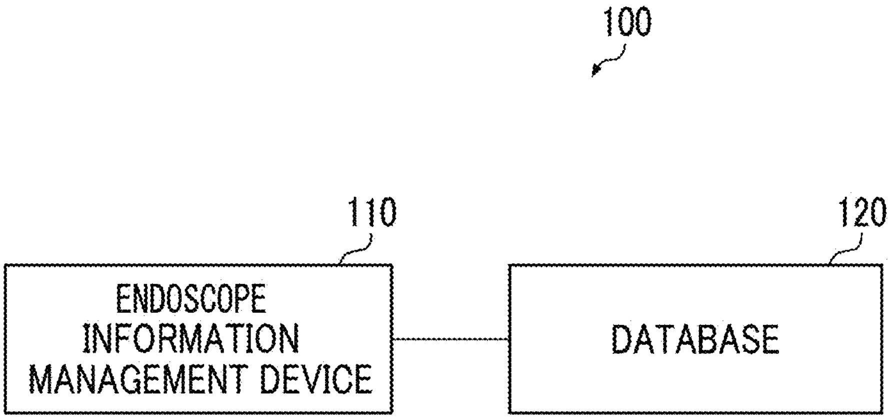
FIG. 29 is a block diagram illustrating an example of a system configuration of an endoscope information management system.

FIG. 29 is a block diagram illustrating an example of a system configuration of the endoscope information management system.

As illustrated in the figure, the endoscope information management system 100 mainly includes an endoscope information management device 110 and a database 120.

The endoscope information management device 110 collects the series of information (examination information) related to the endoscopy, and integrally manages the series of information. In addition, the creation of an examination report is supported via the user terminal 200.

The endoscope information management device 110 includes, as a hardware configuration, a processor, a main storage unit, an auxiliary storage unit, a display unit, an operation unit, a communication unit, and the like. That is, the endoscope information management device 110 has a so-called computer configuration as the hardware configuration. For example, the processor is configured by a CPU. The processor of the endoscope information management device 110 is an example of a second processor. For example, the main storage unit is configured by a RAM. For example, the auxiliary storage unit is configured by a hard disk drive, a solid-state drive (SSD), a flash memory, or the like. The display unit is configured by a liquid-crystal display, an organic EL display, or the like. The operation unit is configured by a keyboard, a mouse, a touch panel, or the like. For example, the communication unit is configured by a communication interface connectable to a network. The endoscope information management device 110 is communicably connected to the endoscope system 10 via the communication unit. More specifically, the endoscope information management device 110 is communicably connected to the endoscopic image processing device 60.

Figure 30:
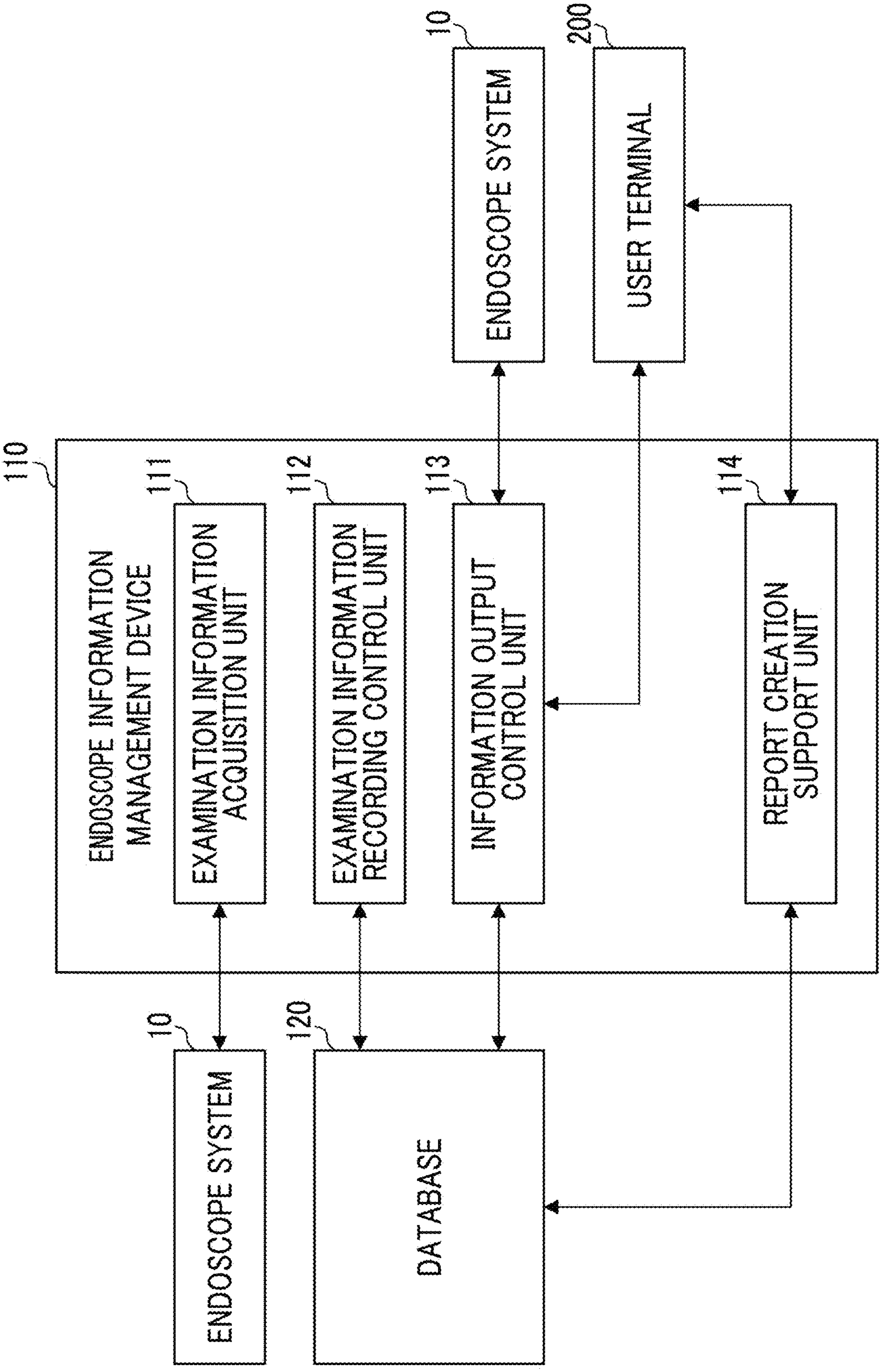
FIG. 30 is a block diagram of main functions of an endoscope information management device.

FIG. 30 is a block diagram of main functions of the endoscope information management device.

As illustrated in the figure, the endoscope information management device 110 has functions of an examination information acquisition unit 111, an examination information recording control unit 112, an information output control unit 113, a report creation support unit 114, and the like. Each function is realized by the processor executing a predetermined program. The auxiliary storage unit stores various programs executed by the processor, various kinds of data necessary for processing, and the like.

The examination information acquisition unit 111 acquires the series of information (examination information) related to the endoscopy from the endoscope system 10. In the information to be acquired, the endoscopic image captured during the examination, the information on the site input during the examination, the information on the diagnosis name, the information on the findings, the information on the treatment name, the information on the treatment tool, the information on the hemostasis treatment tool, and the like are included. In the endoscopic image, a video and a static image are included.

The examination information recording control unit 112 records the examination information acquired from the endoscope system 10 in the database 120.

The information output control unit 113 controls the output of the information recorded in the database 120. For example, the information recorded in the database 120 is output to a request source in response to a request from the user terminal 200, the endoscope system 10, and the like.

The report creation support unit 114 supports the creation of the report on the endoscopy via the user terminal 200. Specifically, a report creation screen is provided to the user terminal 200 to support the input on the screen.

Figure 31:
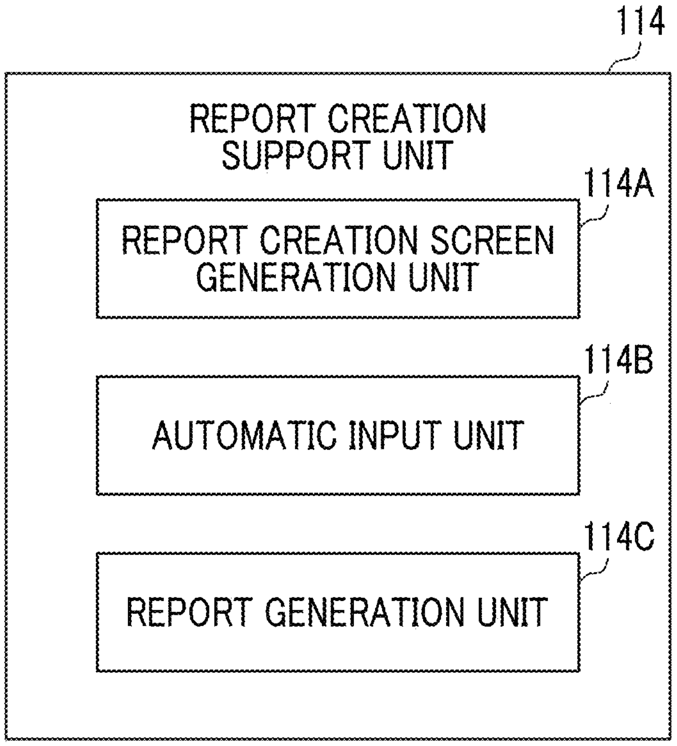
FIG. 31 is a block diagram of main functions of a report creation support unit.

FIG. 31 is a block diagram of main functions of the report creation support unit.

As illustrated in the figure, the report creation support unit 114 has functions of a report creation screen generation unit 114A, an automatic input unit 114B, a report generation unit 114C, and the like.

In response to the request from the user terminal 200, the report creation screen generation unit 114A generates a screen necessary for creating a report, and provides the screen to the user terminal 200.

Figure 32:
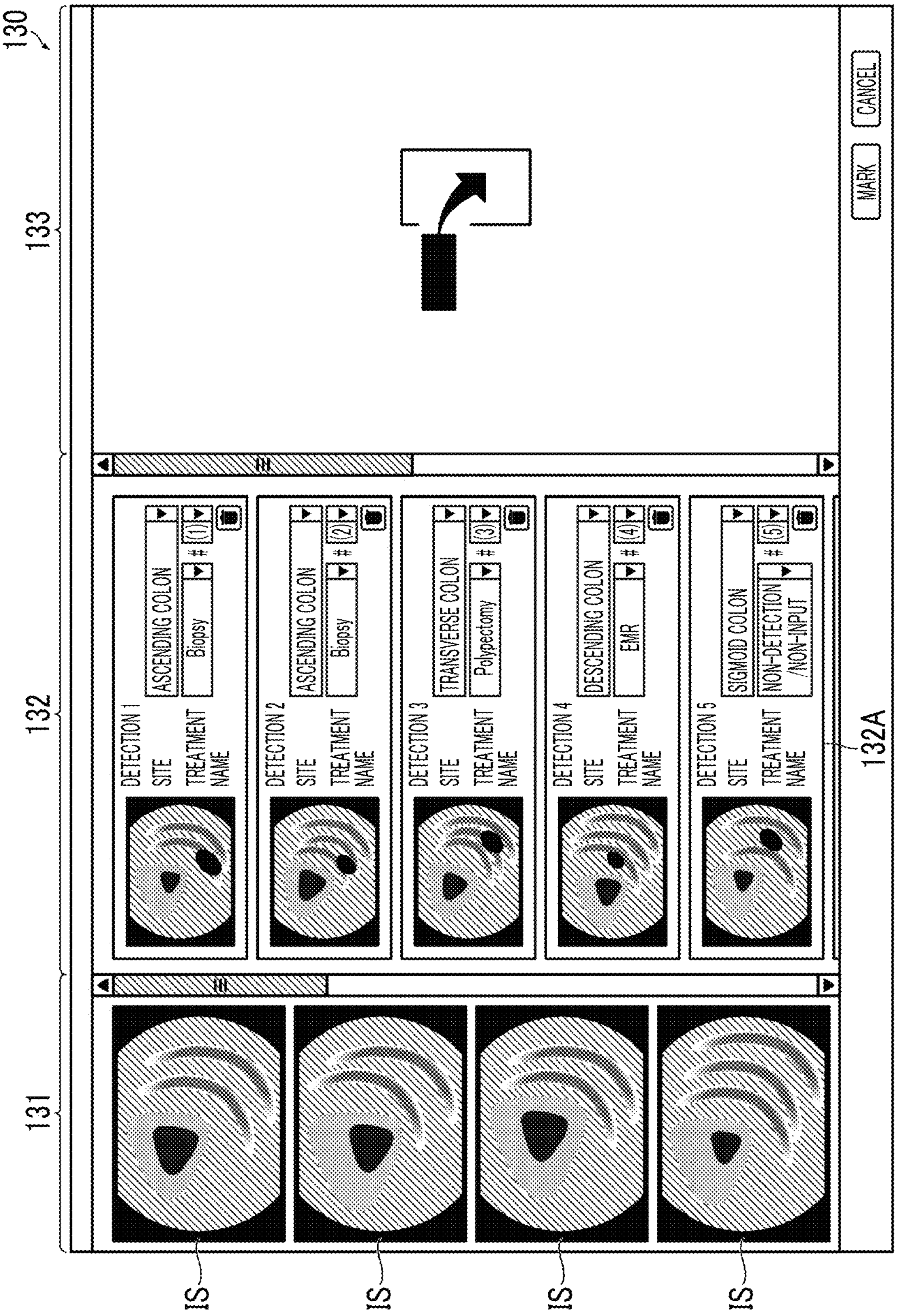
FIG. 32 is a diagram illustrating an example of a selection screen.

FIG. 32 is a diagram illustrating an example of a selection screen.

A selection screen 130 is a screen for selecting a report creation target or the like. As illustrated in the figure, the selection screen 130 has a captured image display region 131, a detection list display region 132, a merge processing region 133, and the like.

The captured image display region 131 is a region in which the static images IS captured during the examination in one endoscopy are displayed. The captured static images IS are displayed in chronological order.

The detection list display region 132 is a region in which the detected lesion or the like is displayed in a list. The detected lesion or the like is displayed by a card 132A in a list in the detection list display region 132. On the card 132A, in addition to the endoscopic image in which the lesion or the like is imaged, the information on the site, the information on the treatment name (information on a specimen collection method in a case of specimen collection), and the like are displayed. The information on the site, the information on the treatment name, and the like can be corrected on the card. In the example illustrated in FIG. 32, by pressing a drop-down button provided in a display column of each piece of information, a drop-down list is displayed, and the information can be corrected. The card 132A is displayed in a detection order from top to bottom in the detection list display region 132.

The merge processing region 133 is a region in which merge processing is performed on the card 132A. The merge processing is performed by dragging the card 132A to be merged to the merge processing region 133.

On the selection screen 130, the user designates the card 132A displayed in the detection list display region 132, and selects the lesion or the like as the report creation target.

Figure 33:
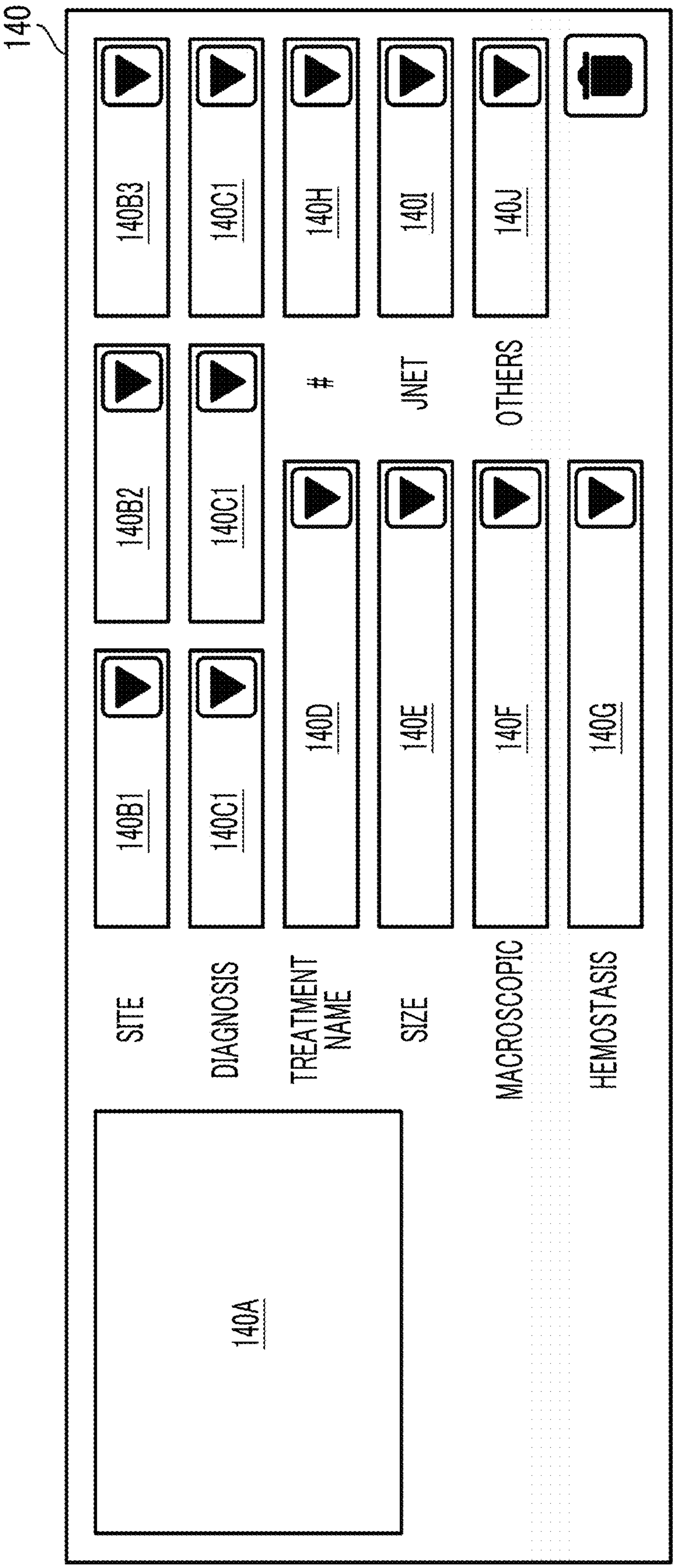
FIG. 33 is a diagram illustrating an example of a detailed input screen.

FIG. 33 is a diagram illustrating an example of a detailed input screen.

A detailed input screen 140 is a screen for inputting various kinds of information necessary for generating a report. As illustrated in the figure, the detailed input screen 140 has a plurality of input fields 140A to 140J for inputting various kinds of information necessary for generating a report.

The input field 140A is an input field for an endoscopic image (static image). The endoscopic image (static image) to be attached to the report is input to the input field 140A.

The input fields 140B1 to 140B3 are input fields for information on a site. A plurality of input fields are prepared for the site so that the information thereof can be input hierarchically. In the example illustrated in FIG. 33, three input fields are prepared such that information on the site can be input in three hierarchies. The input is performed by selecting one option from the drop-down list. The drop-down list is displayed by pressing (clicking or touching) the drop-down button provided in each of the input fields 140B1 to 140B3.

Figure 34:
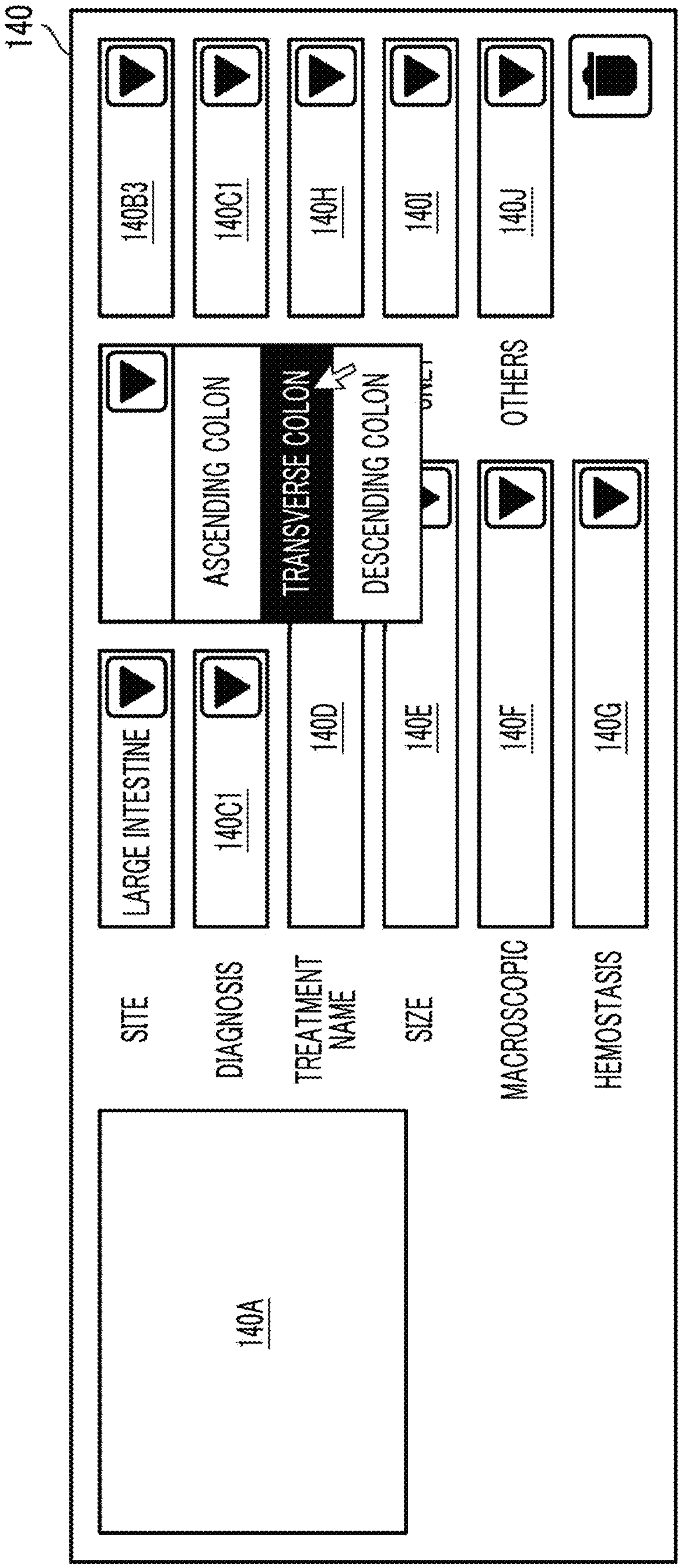
FIG. 34 is a diagram illustrating an example of display of a drop-down list.

FIG. 34 is a diagram illustrating an example of the display of the drop-down list. FIG. 34 illustrates an example of the drop-down list displayed in the input field 140B2 of the second hierarchy for a site.

As illustrated in the figure, in the drop-down list, options are displayed in a list for the designated input field. The user selects one option from the options displayed in a list, and inputs the one option in a target input field. In the example illustrated in the figure, a case where there are three options of "ascending colon", "transverse colon", and "descending colon" is illustrated.

The input fields 140C1 to 140C3 are input fields for information on the diagnosis result. Similarly, a plurality of input fields are prepared for the diagnosis result so that the information thereof can be input hierarchically. In the example illustrated in FIG. 34, three input fields are prepared such that information on the diagnosis result can be input in three hierarchies. The input is performed by selecting one option from the drop-down list. The drop-down list is displayed by pressing the drop-down button provided in each of the input fields 140C1 to 140C3. Selectable diagnosis names are displayed in a list in the drop-down list.

The input field 140D is an input field for information on the treatment name. The input is performed by selecting one option from the drop-down list. The drop-down list is displayed by pressing the drop-down button provided in the input field 140D. Selectable treatment names are displayed in a list in the drop-down list.

The input field 140E is an input field for information on the size of the lesion part. The input is performed by selecting one option from the drop-down list. The drop-down list is displayed by pressing the drop-down button provided in the input field 140E. Selectable values for the size are displayed in a list in the drop-down list.

The input field 140F is an input field for information on the macroscopic classification. The input is performed by selecting one option from the drop-down list. The drop-down list is displayed by pressing the drop-down button provided in the input field 140F. Selectable classifications are displayed in a list in the drop-down list.

The input field 140G is an input field for information on hemostatic methods. The input is performed by selecting one option from the drop-down list. The drop-down list is displayed by pressing the drop-down button provided in the input field 140G. Selectable hemostatic methods are displayed in a list in the drop-down list.

The input field 140H is an input field for information on specimen number. The input is performed by selecting one option from the drop-down list. The drop-down list is displayed by pressing the drop-down button provided in the input field 140H. Selectable numerical values are displayed in a list in the drop-down list.

The input field 140I is an input field for information on the JNET classification. The input is performed by selecting one option from the drop-down list. The drop-down list is displayed by pressing the drop-down button provided in the input field 140I. Selectable JNET classifications are displayed in a list in the drop-down list.

The input field 140J is an input field for other information. The input is performed by selecting one option from the drop-down list. The drop-down list is displayed by pressing the drop-down button provided in the input field 140J. Pieces of information that can be input are displayed in a list in the drop-down list.

The automatic input unit 114B automatically inputs the information of the predetermined input fields of the detailed input screen 140 on the basis of the information recorded in the database 120. As described above, in the endoscope system 10 of the present embodiment, the information on the site input during the examination, the information on the diagnosis name, the information on the findings (information on the macroscopic classification, information on the JNET classification, and information on the size classification), the information on the treatment name, the information on the number of hemostasis treatment tools, and the like are input. The input information is recorded in the database 120. Thus, regarding the site, the diagnosis name, the findings (macroscopic classification, JNET classification, and size classification), the treatment name, and the number of hemostasis treatment tools, the information can be automatically input. The automatic input unit 114B acquires, regarding the lesion or the like as the report creation target, the information on the site, the information on the diagnosis name, the information on the findings (information on the macroscopic classification, information on the JNET classification, and information on the size classification), the information on the treatment name, the information on the number of hemostasis treatment tools, and the like from the database 120, and automatically fills the input fields corresponding to the detailed input screen 140. That is, the input fields 140B 1 to 140B3 for the information on the site, the input fields 140C1 to 140C3 for the information on the diagnosis result, the input field 140D for the information on the treatment name, the input field 140E for the information on the size of the lesion part, the input field 140F for the information on the macroscopic classification, the input field 140G for the information on the hemostatic method, and the input field 140I for the information on the JNET classification are automatically filled. In addition, the automatic input unit 114B acquires the endoscopic image (static image) captured for the lesion or the like as the report creation target from the database 120, and automatically fills the input field 140A for the image.

Figure 35:
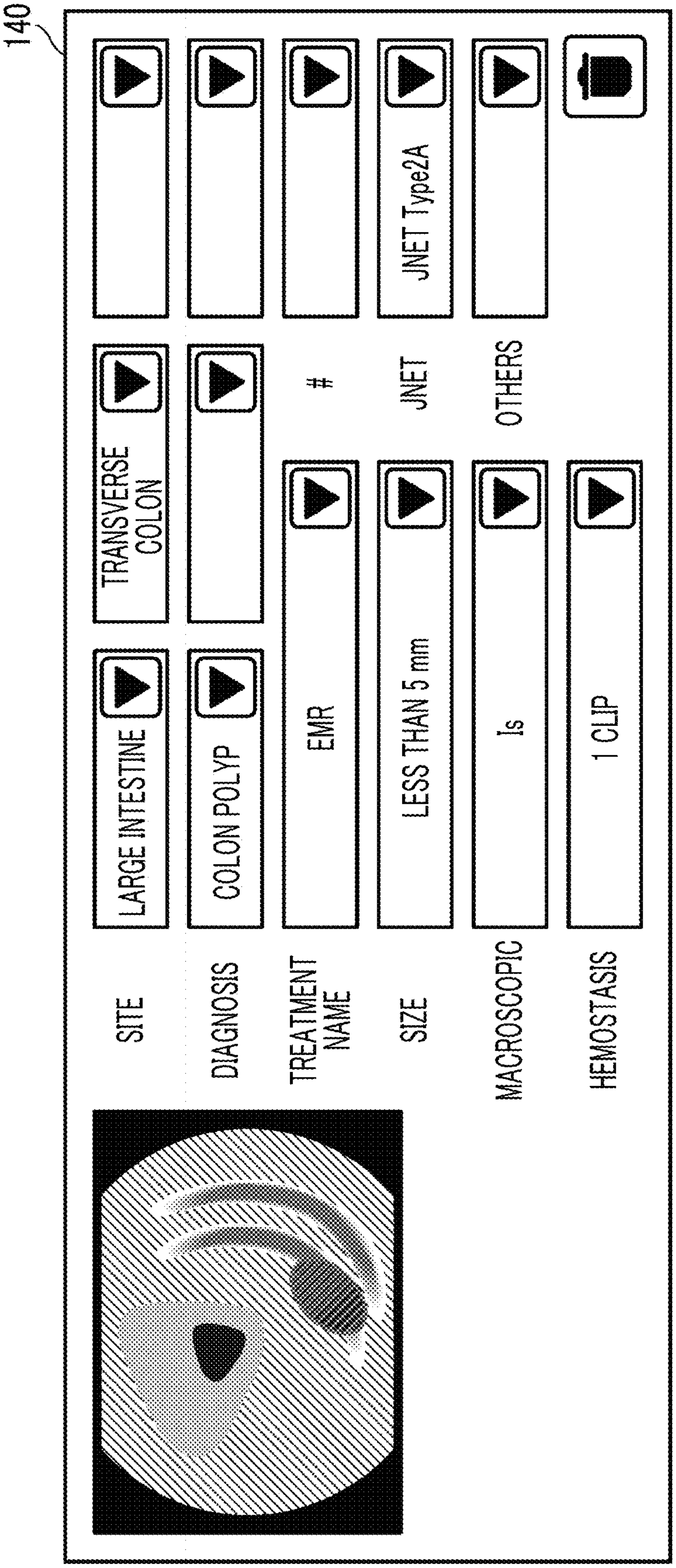
FIG. 35 is a diagram illustrating an example of a detailed input screen which is automatically filled.

FIG. 35 is a diagram illustrating an example of the detailed input screen which is automatically filled.

As illustrated in the figure, the input field for the endoscopic image, the input field for the information on the site, and the input field for the information on the treatment name are automatically filled. As an initial screen of the detailed input screen 140, a screen in which the input field for the endoscopic image, the input field for the information on the site, and the input field for the information on the treatment name are automatically filled is provided to the user terminal 200. The user corrects the input field that is automatically filled, as necessary. For other input fields, in a case where the information to be input can be acquired, it is preferable to automatically fill the input field.

For example, correcting the input field for the endoscopic image is performed by dragging a target thumbnail image to the input field 140A from a thumbnail list of endoscopic images opened in a separate window.

Correcting the input field for the information on the site and the input field for the information on the treatment name is performed by selecting one option from the drop-down list.

Figure 36:
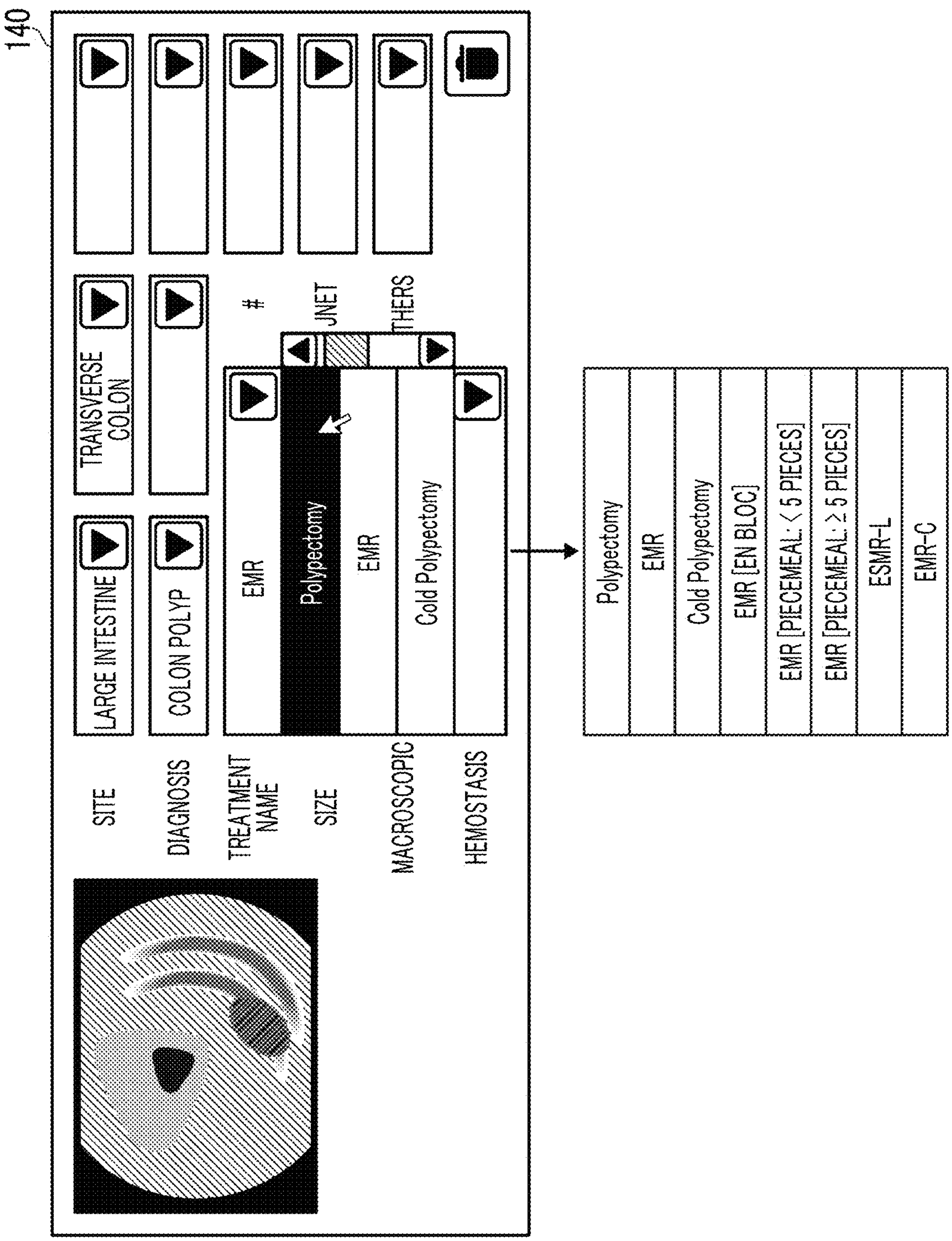
FIG. 36 is a diagram illustrating an example of a detailed input screen during correction.

FIG. 36 is a diagram illustrating an example of the detailed input screen during correction. FIG. 36 illustrates an example of a case where the information in the input field for the treatment name is corrected.

As illustrated in the figure, the correction of the information is performed by selecting one option from the options displayed in the drop-down list.

Here, it is preferable that the number of options displayed in the drop-down list is set to be larger than the number of options displayed during the examination. For example, in a case where the treatment tool is the snare, the options of the treatment name displayed during the examination are three of “Polypectomy”, “EMR”, and “Cold Polypectomy”, as illustrated in FIG. 21B. On the other hand, the treatment names selectable in the detailed input screen 140 are eight of “Polypectomy”, “EMR”, “Cold Polypectomy”, “EMR [en bloc]”, “EMR [piecemeal: <5 pieces]”, “EMR [piecemeal: ≥5 pieces]”, “ESMR-L”, and “EMR-C”, as illustrated in FIG. 36. In this manner, in a case of creating a report, it is possible to easily correct target information by presenting more options. Meanwhile, during the examination, by narrowing down the options, it is possible for the user to efficiently select the treatment name.

Figure 37:
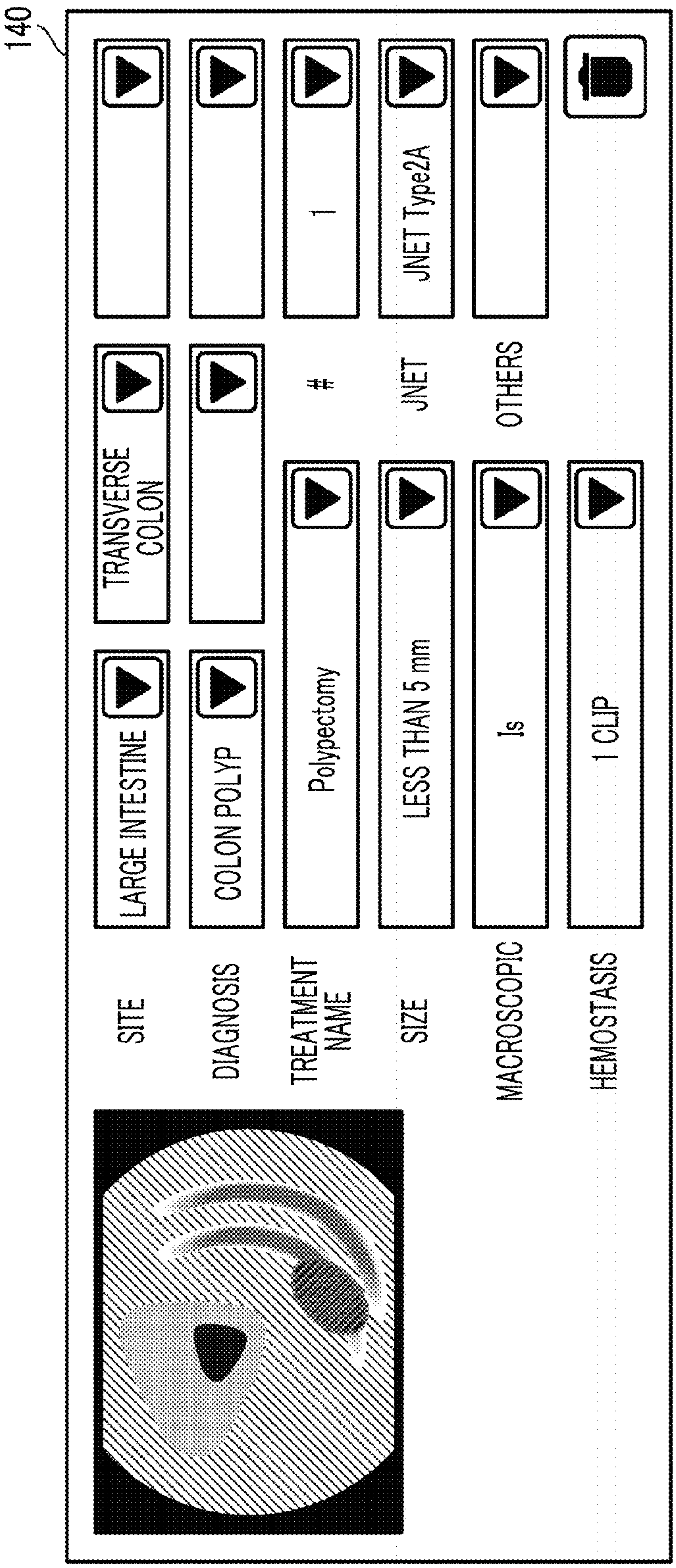
FIG. 37 is a diagram illustrating an example of a detailed input screen after an input is completed.

FIG. 37 is a diagram illustrating an example of the detailed input screen after the input is completed. As illustrated in the figure, the information to be entered in the report is input to each input field.

The report generation unit 114C automatically generates the report in a predetermined format, for the lesion or the like selected as the report creation target, on the basis of the information input on the detailed input screen 140. The generated report is presented on the user terminal 200.

[User Terminal]

The user terminal 200 is used for viewing various kinds of information related to the endoscopy, creating a report, and the like. The user terminal 200 includes, as a hardware configuration, a processor, a main storage unit, an auxiliary storage unit, a display unit, an operation unit, a communication unit, and the like. That is, the user terminal 200 has a so-called computer (for example, personal computer, tablet computer, or the like) configuration as the hardware configuration. For example, the processor is configured by a CPU. For example, the main storage unit is configured by a RAM. For example, the auxiliary storage unit is configured by a hard disk drive, a solid-state drive, a flash memory, or the like. The display unit is configured by a liquid-crystal display, an organic EL display, or the like. The operation unit is configured by a keyboard, a mouse, a touch panel, or the like. For example, the communication unit is configured by a communication interface connectable to a network. The user terminal 200 is communicably connected to the endoscope information management system 100 via the communication unit. More specifically, the user terminal 200 is communicably connected to the endoscope information management device 110.

In the endoscopic image diagnosis support system 1 of the present embodiment, the user terminal 200 constitutes the report creation support device together with the endoscope information management system 100. The display unit of the user terminal 200 is an example of a second display unit.

[Operation of Endoscopic Image Diagnosis Support System]

[Operation of Endoscope System During Examination]

Hereinafter, the operation of the endoscope system 10 during the examination, particularly the screen display and the acceptance of the input of the information necessary for creating a report will be described on the basis of FIG. 28.

In a case where the examination starts, the image (endoscopic image) captured by the endoscope 20 is displayed on the display device 70 (refer to FIG. 10). Usually, in the large intestine examination, the examination is performed from the ileocecum.

In a case where the ileocecum is detected from the endoscopic image by the specific region detection unit 63C, the site selection box 71 is displayed at a predetermined position on the screen (refer to FIG. 15). The site selection box 71 is displayed on the screen in a state where the ascending colon is selected in advance. The ascending colon is a site to which the ileocecum belongs. In addition, the site selection box 71 is displayed in an emphasized manner for a fixed time from the display start.

In a case of changing the site being selected, the user changes the site using the audio input device 54 or the foot switch 53. Except in specific cases, the selection of the site can be performed at any time during the display of the site selection box 71.

In a case where the detection support function for the lesion part is ON, processing of detecting the lesion part from the endoscopic image is performed. The processing of detecting the lesion part is performed by the lesion part detection unit 63A. In a case where the lesion part is detected by the lesion part detection unit 63A, the detected lesion part P is displayed by being enclosed with the frame F, on the endoscopic image I that is being displayed on the screen (refer to FIG. 11). Further, in a case where the discrimination support function is ON, the discrimination processing is performed on the detected lesion part. The discrimination processing is performed by the discrimination unit 63B. The discrimination result of the discrimination unit 63B is displayed in the discrimination result display region A3 (refer to FIG. 11).

In a case where the discrimination result is output, the diagnosis name selection box 72 is displayed at a predetermined position on the screen (refer to FIG. 17). At the same time, the input information display box 77 is displayed at a predetermined position on the screen (refer to FIG. 17).

By displaying the diagnosis name selection box 72 on the screen, the input (selection) of the diagnosis name becomes possible. On the other hand, the acceptance of the input of the site is stopped.

The user selects the option using the audio input device 54 to input the diagnosis name. That is, the user reads out and inputs the diagnosis name to be described in the report from among the diagnosis names displayed in a list in the diagnosis name selection box 72. The selected diagnosis name is displayed to be distinguishable from other diagnosis names in the diagnosis name selection box 72 (refer to FIG. 17). In a case where the user inputs the diagnosis name, the display of the input information display box 77 is updated. That is, the information on the input diagnosis name is displayed in the field of "diagnosis" (refer to FIG. 17 and (A) of FIG. 27).

In a case where a fixed time has elapsed after the diagnosis name is selected, the findings selection boxes 73A to 73C are displayed at predetermined positions on the screen (refer to FIG. 19). The findings selection boxes 73A to 73C are displayed in order. First, the findings selection box 73A for the macroscopic classification is displayed on the screen.

The user selects the option using the audio input device 54 to input the macroscopic classification. The selected classification is displayed to be distinguishable from other classifications in the findings selection box 73A for the macroscopic classification (refer to FIG. 18A). In a case where the user inputs the macroscopic classification, the display of the input information display box 77 is updated. That is, the information on the input macroscopic classification is displayed in the field of "findings 1" (refer to (B) of FIG. 27).

In a case where a fixed time has elapsed after the macroscopic classification is selected, the findings selection box 73B for the JNET classification is displayed on the screen.

The user selects the option using the audio input device 54 to input the JNET classification. The selected classification is displayed to be distinguishable from other classifications in the findings selection box 73B for the JNET classification (refer to FIG. 18B).

In a case where the user inputs the JNET classification, the display of the input information display box 77 is updated. That is, the information on the input JNET classification is displayed in the field of "findings 2" (refer to (B) of FIG. 27).

In a case where a fixed time has elapsed after the JNET classification is selected, the findings selection box 73C for the size classification is displayed on the screen.

The user selects the option using the audio input device 54 to input the size classification. The selected classification is displayed to be distinguishable from other classifications in the findings selection box 73C for the size classification (refer to FIG. 18C).

In a case where the user inputs the size classification, the display of the input information display box 77 is updated. That is, the information on the input size classification is displayed in the field of "findings 3" (refer to (C) of FIG. 27).

In a case where the size classification is selected, the input of the information on the diagnosis name and on the findings is completed. In a case where a fixed time has elapsed after the size classification is selected, the findings selection box 73C for the size classification disappears from the screen. At the same time, the display of the input information display box 77 disappears from the screen.

In a case where the findings selection box 73C for the size classification disappears from the screen, the selection of the site becomes possible again.

Thereafter, in a case where the treatment tool is detected from the endoscopic image by the treatment tool detection unit 63D, the treatment tool detection mark 74 is displayed on the screen (refer to FIG. 23). As the treatment tool detection mark 74, a mark corresponding to the detected treatment tool is displayed.

At the same time as the display of the treatment tool detection mark 74, the treatment name selection box 75 and the input information display box 77 are displayed on the screen (refer to FIG. 23).

In the treatment name selection box 75, the names corresponding to the detected treatment tool are displayed. For example, in a case where the detected treatment tool is the biopsy forceps, the treatment name selection box 75 for biopsy forceps is displayed (refer to FIG. 21A). In addition, for example, in a case where the detected treatment tool is the snare, the treatment name selection box 75 for snare is displayed (refer to FIG. 21B). The treatment names displayed in the treatment name selection box 75 are displayed in a predetermined arrangement. In addition, the treatment name selection box 75 is displayed in a state where a specific treatment name is selected in advance. In a case of changing the treatment name selected in advance, the selection operation is performed. The user performs the selection operation of the treatment name using the foot switch 53 or the audio input device 54. The selected treatment name is displayed to be distinguishable from the other options (refer to FIGS. 21A and 21B).

In a case where the user inputs the treatment name, the display of the input information display box 77 is updated. That is, the information on the input treatment name is displayed in the field of "treatment" (refer to FIG. 23). More specifically, the information is rewritten and displayed with information on the newly input treatment name.

The selection operation can be performed while the treatment name selection box 75 is being displayed on the screen. Meanwhile, during this time, the acceptance of the input of the site is stopped.

In a case where the treatment tool disappears from the endoscopic image, the treatment tool detection mark 74 disappears from the screen. Further, after a fixed time has elapsed after the disappearance of the treatment tool from the endoscopic image, the treatment name selection box 75 disappears from the screen. At the same time, the input information display box 77 disappears from the screen. In a case where the treatment name selection box 75 disappears from the screen, the selection of the treatment name is confirmed.

In a case where the treatment name selection box 75 disappears from the screen, the selection of the site becomes possible again.

Thereafter, in a case where the hemostasis treatment tool is detected from the endoscopic image by the hemostasis detection unit 63E, the hemostasis selection box 76 and the input information display box 77 are displayed on the screen (refer to FIG. 25).

In the hemostasis selection box 76, the options of the number of hemostasis treatment tools are displayed in a predetermined arrangement. In addition, the hemostasis selection box 76 is displayed in a state where a specific option is selected in advance. In a case of changing the option selected in advance, the selection operation is performed. The user performs the selection operation using the foot switch 53 or the audio input device 54. The selected option is displayed to be distinguishable from the other options (refer to FIG. 24).

In a case where the user selects the option, the display of the input information display box 77 is updated. That is, the information on the input option is displayed in the field of "hemostasis" (refer to FIG. 25). More specifically, the information is rewritten and displayed with information on the newly selected option.

The selection operation can be performed while the hemostasis selection box 76 is being displayed on the screen. Meanwhile, during this time, the acceptance of the input of the site is stopped.

In a case where the hemostasis treatment tool disappears from the endoscopic image, the hemostasis selection box 76 disappears from the screen. At the same time, the input information display box 77 disappears from the screen. In a case where the hemostasis selection box 76 disappears from the screen, the selection of the number of hemostasis treatment tools is confirmed.

By the series of input operations described above, the input of the information necessary for creating a report is completed. The user performs an input confirmation operation to confirm the input. The input confirmation operation is performed by performing the audio input of a predetermined keyword. Specifically, the input is confirmed by inputting "confirm" by audio.

In a case where the input confirmation operation is performed, the input information display box 77 is displayed on the screen for a fixed time. The user can check the series of input information by checking the display of the input information display box 77.

Note that, in a case where the hemostasis selection box 76 disappears from the screen, the selection of the site becomes possible again. Thereafter, in a case where a static image is captured by the user, the display prompting the selection of the site is performed. Specifically, the site selection box 71 is displayed in an emphasized manner (refer to FIG. 15). In a case of changing the site, the user selects the site using the foot switch 53 or the audio input device 54.

As described above, with the endoscope system 10 of the present embodiment, an interface for inputting the information necessary for creating a report is displayed on the screen in the form of the selection box. Accordingly, it is possible to input the information necessary for creating a report in a simple and easy-to-understand manner. In addition, since the selection box is displayed according to the recognition result of the image recognition processing unit 63, it is possible to prompt the input at an appropriate timing. Accordingly, it is possible to efficiently input the information necessary for creating a report. In addition, predetermined selection boxes are displayed in a state where a specific option is selected in advance. Accordingly, it is possible to more efficiently input the information necessary for creating a report.

[Report Creation Support]

Creating a report is performed using the user terminal 200. In a case where the report creation support is requested from the user terminal 200 to the endoscope information management system 100, processing of supporting the report creation starts.

First, the examination as the report creation target is selected. The examination as the report creation target is selected on the basis of patient information or the like.

In a case where the examination as the report creation target is selected, the lesion or the like as the report creation target is selected. In this case, the selection screen 130 is provided to the user terminal 200 (refer to FIG. 32). On the selection screen 130, the user designates the card 132A displayed in the detection list display region 132, and selects the lesion or the like as the report creation target.

In a case where the lesion or the like as the report creation target is selected, the detailed input screen 140 is provided to the user terminal 200 (refer to FIG. 33). In this case, the detailed input screen 140 is provided to the user terminal 200 in a state where information is automatically input to the predetermined input fields in advance. Specifically, the detailed input screen 140 is provided in a state where information acquired during the examination is input to the input field for the endoscopic image, the input field for the site, the input field for the diagnosis, the input field for the treatment name, the input field for the size classification, the input field for the macroscopic classification, the input field for the JNET classification, and the input field for the hemostasis in advance (refer to FIG. 35). These pieces of information are automatically input on the basis of the information recorded in the database 120. The user corrects the automatically input information as necessary. Further, the user inputs information to other input fields.

In a case where predetermined information is input and the generation of the report is requested, the report is generated in a predetermined format on the basis of the input information. The report generation unit 114C automatically generates the report in a predetermined format, for the lesion or the like selected as the report creation target, on the basis of the information input on the detailed input screen 140. The generated report is provided to the user terminal 200.

MODIFICATION EXAMPLE

[Input of Information on Site]

(1) Configuration of Site Selection Box

In the embodiment described above, the configuration is adopted in which the schema diagram of the hollow organ as the examination target is displayed and the site is selected, but the method of selecting the site in the site selection box 71 is not limited thereto. In addition, for example, options written in text may be displayed in a list, and the user may select the option. For example, in the example of the embodiment described above, a configuration can be adopted in which three of "ascending colon", "transverse colon", and "descending colon" are written in text, and are displayed in the site selection box 71 in a list, and the user selects one. Further, for example, a configuration can be adopted in which the text notation and the schema diagram are combined and displayed. Moreover, the site being selected may be separately displayed as text. Accordingly, it is possible to clarify the site being selected.

Further, the method of dividing the sites as the options can be appropriately set according to the type of the hollow organ as the examination target, the purpose of the examination, and the like. For example, in the embodiment described above, the large intestine is divided into three sites, but can be divided into more detailed sites. For example, in addition to "ascending colon", "transverse colon", and "descending colon", "sigmoid colon" and "rectum" can be added as the options. Moreover, each of "ascending colon", "transverse colon", and "descending colon" may be classified in more detail, and a more detailed site can be selected.

(2) Emphasized Display

It is preferable that the emphasized display of the site selection box 71 is executed in a timely manner at a timing at which it is necessary to input the information on the site. For example, as described above, the information on the site is recorded in association with the diagnosis name, the findings, the treatment name, the number of hemostasis treatment tools, and the like. Therefore, it is preferable to select the site according to the input of these pieces of information. Note that, as described above, the acceptance of the selection of the site is stopped while the selection of the diagnosis name, the findings, the treatment name, and the number of hemostasis treatment tools is being accepted. Therefore, it is preferable that, before or after the selection thereof is accepted, the site selection box 71 is displayed in an emphasized manner to prompt the selection of the site. Note that, since a plurality of lesion parts are detected in the same site in some cases, it is more preferable to select the site in advance before the treatment. Therefore, for example, it is preferable that the site selection box 71 is displayed in an emphasized manner at a timing at which the treatment tool is detected from the image or at a timing at which the lesion part is detected from the image, to prompt the selection of the site.

Further, the site selection box 71 may be displayed in an emphasized manner at the timing of switching the site to prompt the selection of the site. In this case, for example, the site switching is detected from the image by using the AI or the trained model. As in the embodiment described above, in the examination for the large intestine, in a case where the site is selected by dividing the large intestine into the ascending colon, the transverse colon, and the descending colon, the site switching can be detected by detecting the hepatic flexure (right colon), the splenic flexure (left colon), and the like from the image. For example, switching from the ascending colon to the transverse colon or switching from the transverse colon to the ascending colon can be detected by detecting the hepatic flexure. Further, switching from the transverse colon to the descending colon or switching from the descending colon to the transverse colon can be detected by detecting the splenic flexure.

As described above, as the method of the emphasized display, in addition to the method of displaying the site selection box 71 in an enlarged manner, methods of changing a color from the normal display form, enclosing with a frame, blinking, and the like can be adopted. Further, a method of appropriately combining the methods can be adopted.

Further, instead of or in addition to the method of prompting the selection of the site via the emphasized display, processing of prompting the selection of the site may be performed using an audio guide or the like. Alternatively, the display of prompting the selection of the site on the screen (for example, message, icon, or the like) may be separately performed.

(3) Other Uses of Information on Site

In the embodiment described above, a case where the information on the selected site is recorded in association with the information on the treatment name has been described, but the use of the information on the site is not limited thereto. For example, a configuration can be adopted in which the information on the site being selected is recorded in association with the captured endoscopic image. Accordingly, it can be easily discriminated from which site the acquired endoscopic image is captured. Further, classification or the like of the endoscopic image can be performed for each site by using the associated information on the site.

(4) Selection Operation of Site

In the embodiment described above, the configuration is adopted in which the selection operation of the site is performed using the foot switch 53 or the audio input device 54, but the selection operation of the site is not limited thereto. In addition, a configuration can be adopted in which the selection operation is performed by a gaze input, a button operation, a touch operation on a touch panel, or the like. In addition, a configuration can be adopted in which the selection operation of the site is performed only using the foot switch 53 or only using the audio input device 54.

[Input of Information of Diagnosis Name]

(1) Selection Operation of Diagnosis Name

In the embodiment described above, the configuration is adopted in which the selection operation of the diagnosis name is performed only by the audio input device 54, but the selection operation of the diagnosis name is not limited thereto. In addition, for example, a configuration can be adopted in which the selection operation is performed by a foot switch, an audio input, a gaze input, a button operation, a touch operation on a touch panel, and the like. In addition, a configuration may be adopted in which the input can be performed by arbitrarily selecting the plurality of input devices. In addition, the user may be able to arbitrarily set the input devices that can be used.

(2) Confirmation Processing of Selection Operation

In the embodiment described above, the configuration is adopted in which the selection is confirmed immediately before a timing of moment at which the diagnosis name is selected, but a configuration may be adopted in which a selection acceptance period is set. In this case, the selection is confirmed after the selection acceptance period has elapsed. Therefore, during the selection acceptance period, re-selection is possible. That is, the correction of the selection becomes possible. In addition, in this case, during the selection acceptance period, the diagnosis name selection box 72 is continuously displayed. In addition, in the diagnosis name selection box 72 being displayed, the option being selected is displayed to be distinguishable from the other options.

(3) Display Timing of Diagnosis Name Selection Box

In the embodiment described above, the configuration is adopted in which the diagnosis name selection box 72 is displayed on the screen in accordance with the timing at which the discrimination result is output, but the timing of displaying the diagnosis name selection box 72 is not limited thereto. A configuration may be adopted in which the diagnosis name selection box 72 is displayed according to other detection results (recognition results). For example, a configuration may be adopted in which the diagnosis name selection box is displayed in a case where the treatment tool is detected from the endoscopic image. In this case, for example, first, the diagnosis name selection box 72 is displayed, the diagnosis name is selected, and then the treatment name selection box 75 is displayed. Alternatively, the treatment name selection box 75 is displayed first, the treatment name is selected, and then the diagnosis name selection box 72 is displayed. In addition, for example, a configuration may be adopted in which the diagnosis name selection box 72 is displayed in a case where the hemostasis treatment tool is detected from the endoscopic image. In this case, first, the diagnosis name selection box 72 is displayed, the diagnosis name is selected, and then the hemostasis selection box 76 is displayed. Alternatively, the hemostasis selection box 76 is displayed first, the number of hemostasis treatment tools is selected, and then the diagnosis name selection box 72 is displayed.

(4) Display of Option

The options displayed in the diagnosis name selection box 72 may be arbitrarily set by the user. In this case, it is preferable that the user can arbitrarily set and edit the number, the order, and the default option of diagnosis names to be displayed. Accordingly, it is possible to build a user-friendly environment for each user.

In addition, a selection history may be recorded, and the display order may be automatically corrected on the basis of the recorded selection history. For example, on the basis of the history, the display order may be corrected to the descending order of the selection frequency, or the default option may be corrected. Further, for example, the display order may be corrected to an order of newest selection on the basis of the history. In this case, the display is made in the order of the last selected option (previously selected option) displayed at the top, followed by the second-to-last selected option, the third-to-last selected option, and so on. Similarly, on the basis of the history, the last selected option may be corrected to be the default option.

[Input of Information on Findings]

(1) Selection Operation of Findings

In the embodiment described above, the configuration is adopted in which the selection operation of the findings is performed only by the audio input device 54, but the selection operation of the findings is not limited thereto. In addition, for example, a configuration can be adopted in which the selection operation is performed by a foot switch, an audio input, a gaze input, a button operation, a touch operation on a touch panel, and the like. In addition, a configuration may be adopted in which the input can be performed by arbitrarily selecting the plurality of input devices. In addition, the user may be able to arbitrarily set the input devices that can be used.

(2) Confirmation Processing of Selection Operation

In the embodiment described above, the configuration is adopted in which the selection is confirmed immediately before a timing of moment at which the option of the findings is selected, but a configuration may be adopted in which a selection acceptance period is set. In this case, the selection is confirmed after the selection acceptance period has elapsed. Therefore, during the selection acceptance period, re-selection is possible. That is, the correction of the selection becomes possible. In addition, in this case, during the selection acceptance period, the findings selection box is continuously displayed. In addition, in the findings selection box being displayed, the option being selected is displayed to be distinguishable from the other options.

(3) Display Timing of Findings Selection Box

In the embodiment described above, the configuration is adopted in which the findings selection boxes 73A to 73C are displayed in order on the screen after the selection of the diagnosis name, but the timing at which the findings selection boxes 73A to 73C are displayed is not limited thereto. A configuration may be adopted in which the findings selection boxes 73A to 73C are displayed according to other detection results (recognition results). For example, a configuration may be adopted in which the findings selection boxes 73A to 73C are displayed in a case where the treatment tool is detected from the endoscopic image. In this case, for example, first, the findings selection boxes 73A to 73C are displayed in order, the option is selected in each of the findings selection boxes 73A to 73C, and then the treatment name selection box 75 is displayed. Alternatively, the treatment name selection box 75 is displayed first, the treatment name is selected, and then the findings selection boxes 73A to 73C are displayed in order. In addition, for example, a configuration may be adopted in which the findings selection boxes 73A to 73C are displayed in a case where the hemostasis treatment tool is detected from the endoscopic image. In this case as well, first, the findings selection boxes 73A to 73C are displayed in order, the option is selected in each of the findings selection boxes 73A to 73C, and then the hemostasis selection box 76 is displayed. Alternatively, the hemostasis selection box 76 is displayed first, the number of hemostasis treatment tools is selected, and then the findings selection boxes 73A to 73C are displayed.

(4) Switching of Display

In the embodiment described above, the configuration is adopted in which, in a case where there are a plurality of findings selection boxes, the findings selection boxes are switched and displayed in order, but the display form in the case where there are a plurality of findings selection boxes is not limited thereto.

Figure 38:
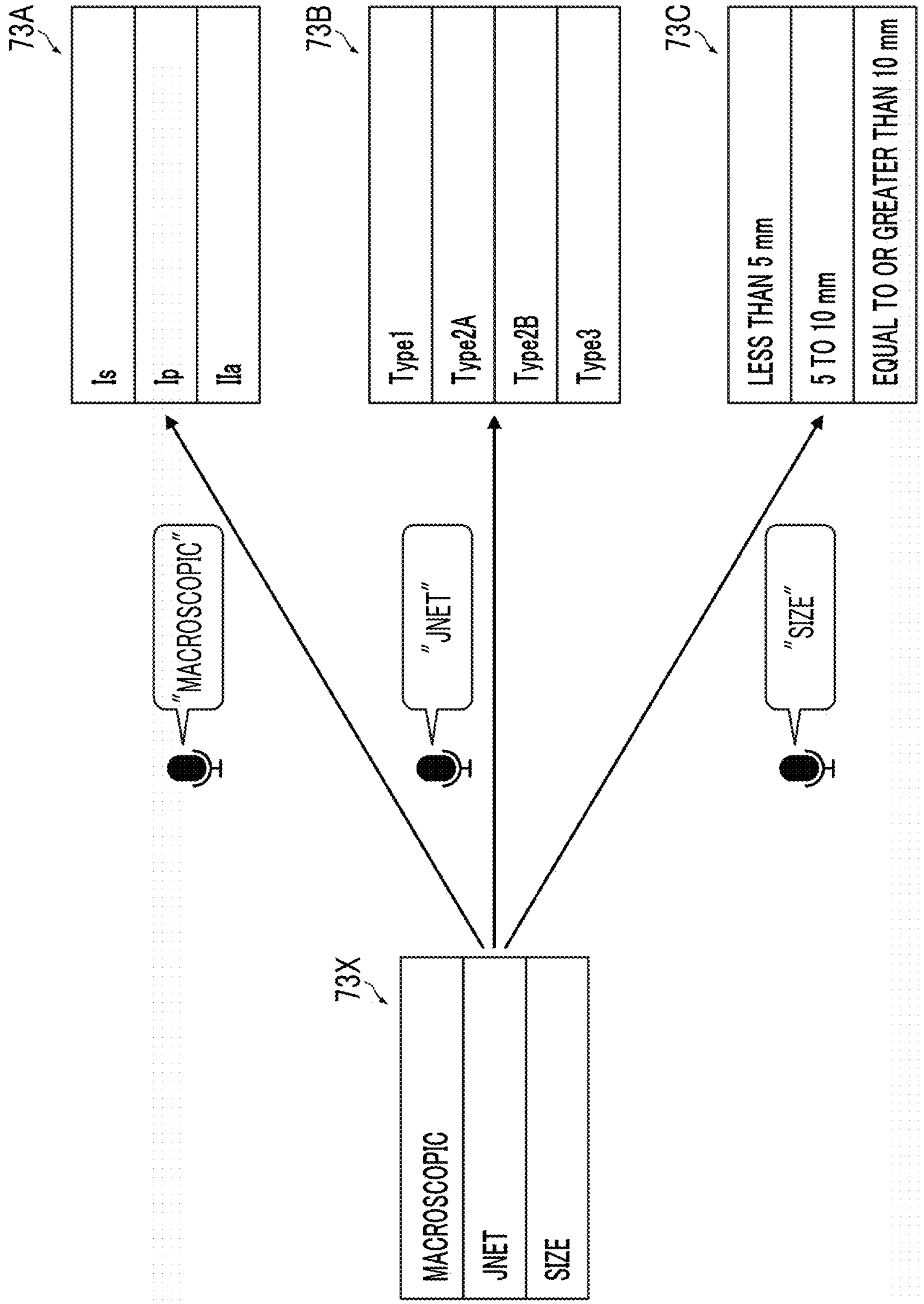
FIG. 38 is a diagram illustrating another example of a display method in a case where there are a plurality of findings selection boxes.

FIG. 38 is a diagram illustrating another example of a display method in a case where there are a plurality of findings selection boxes.

FIG. 38 illustrates an example of a case where a menu is used to display the findings selection boxes 73A to 73C where an input is desired. In the example illustrated in FIG. 38, first, a menu box 73X for the findings is displayed on the screen. In the menu box 73X, selectable findings selection boxes 73A to 73C are displayed in a list as the options. The user selects the findings selection boxes 73A to 73C where an input is desired, from among the options displayed in the menu box 73X. For example, in a case of inputting the findings for the macroscopic classification, “macroscopic” is selected from among the options. Accordingly, the display on the screen is switched from the menu box 73X to the findings selection box 73A for the macroscopic classification. In addition, for example, in a case of inputting the findings for the JNET classification, “JNET” is selected from among the options. Accordingly, the display on the screen is switched from the menu box 73X to the findings selection box 73B for the JNET classification. In addition, for example, in a case of inputting the findings for the size classification, “size” is selected from among the options. Accordingly, the display on the screen is switched from the menu box 73X to the findings selection box 73C for the size classification. In a case of performing the selection operation using the audio input device 54, the option displayed in a list in the menu box 73X is read out to select the findings selection boxes 73A to 73C where an input is desired.

In a case where the selection processing is performed in the displayed findings selection boxes 73A to 73C, the menu box 73X is displayed on the screen again. On the other hand, in a case where the selection processing is completed in all the findings selection boxes 73A to 73C, the menu box 73X is no longer displayed.

Note that the conditions for displaying the menu box 73X are the same as in the embodiment described above. That is, after the selection of the diagnosis name, the menu box 73X is displayed on the screen. In addition, for example, a configuration can be adopted in which the menu box 73X is displayed by inputting “menu” by audio.

A configuration can be adopted in which a menu is used to display the findings selection boxes 73A to 73C where an input is desired.

(5) Display of Option

The options displayed in the findings selection box may be arbitrarily set by the user. In this case, it is preferable that the user can arbitrarily set and edit the number and order of options to be displayed, the default option, and the like. Accordingly, it is possible to build a user-friendly environment for each user.

In addition, a selection history may be recorded, and the display order may be automatically corrected on the basis of the recorded selection history. For example, on the basis of the history, the display order may be corrected to the descending order of the selection frequency, or the default option may be corrected. Further, for example, the display order may be corrected to an order of newest selection on the basis of the history. In this case, the display is made in the order of the last selected option (previously selected option) displayed at the top, followed by the second-to-last selected option, the third-to-last selected option, and so on. Similarly, on the basis of the history, the last selected option may be corrected to be the default option.

(6) Settings of Findings Selection Box to be Displayed on Screen

In the embodiment described above, the configuration is adopted in which, as the findings selection boxes, the findings selection box 73A for inputting the findings for the macroscopic classification, the findings selection box 73B for inputting the findings for the JNET classification, and the findings selection box 73C for inputting the findings for the size classification are displayed in order, but the findings selection boxes to be displayed may be arbitrarily set by the user. For example, depending on the user's settings, only the findings selection box 73B for inputting the findings for the JNET classification may be displayed.

In addition, in the embodiment described above, the configuration is adopted in which, in a case of outputting the discrimination result, first, the selection box for the diagnosis name is displayed and then the selection box for the findings is displayed, but a configuration can be adopted in which only one of the selection box for the diagnosis name or the selection box for the findings is displayed. In addition, the settings may be arbitrarily set by the user. In this case, the set selection box is displayed on the screen according to the output of the discrimination result.

[Input of Information on Treatment Name]

(1) Selection Operation of Treatment Name

In the embodiment described above, the configuration is adopted in which the selection operation of the treatment name is performed using the foot switch 53 or the audio input device 54, but the selection operation of the treatment name is not limited thereto. In addition, a configuration can be adopted in which the selection operation is performed by a gaze input, a button operation, a touch operation on a touch panel, or the like. In addition, a configuration can be adopted in which the selection operation of the treatment name is performed only using the foot switch 53 or only using the audio input device 54. In addition, the user may be able to arbitrarily set the input devices that can be used.

(2) Configuration of Treatment Name Selection Box

The treatment names to be displayed as the selectable treatment names in the treatment name selection box 75 may be arbitrarily set by the user. That is, the user may arbitrarily set or edit the table. In this case, it is preferable that the user can arbitrarily set and edit the number, the order, and the default option of treatment names to be displayed. Accordingly, it is possible to build a user-friendly environment for each user.

Further, a selection history may be recorded, and the table may be automatically corrected on the basis of the recorded selection history. For example, on the basis of the history, the display order may be corrected to the descending order of the selection frequency, or the default option may be corrected. Further, for example, the display order may be corrected to an order of newest selection on the basis of the history. In this case, the display is made in the order of the last selected option (previously selected option) displayed at the top, followed by the second-to-last selected option, the third-to-last selected option, and so on. Similarly, on the basis of the history, the last selected option may be corrected to be the default option.

In addition, in the options to be displayed in the treatment name selection box 75, items such as "no treatment" and/or "post-selection" can be included in addition to the treatment name. Accordingly, for example, even in a case where the treatment is not performed, information thereof can be recorded. Further, it is possible to cope with a case where an input of the treatment name is performed after the examination, a case where the performed treatment is not included in the options, or the like.

Further, in the embodiment described above, the treatment name selection box 75 is displayed by associating the treatment tools with the treatment name selection boxes in a one-to-one manner, but the treatment name selection box 75 may be displayed by associating one treatment name selection box with a plurality of treatment tools. That is, in a case where a plurality of treatment tools are detected from the image, the treatment name selection box 75, in which the option of the treatment name corresponding to the combination of the plurality of treatment names is displayed, is displayed on the screen 70A.

(3) Display Timing of Treatment Name Selection Box

In the embodiment described above, the configuration is adopted in which the treatment name selection box 75 is displayed in a case where the treatment tool is detected, but the timing at which the treatment name selection box 75 is displayed is not limited thereto. In addition, for example, a configuration can be adopted in which the treatment name selection box 75 is displayed in a case where it is detected that the treatment tool has disappeared from the endoscopic image. In this case, a configuration may be adopted in which the treatment name selection box 75 is displayed immediately after detecting that the treatment tool has disappeared from the endoscopic image, and a configuration may be adopted in which the treatment name selection box 75 is displayed after a fixed time has elapsed after detecting that the treatment tool has disappeared from the endoscopic image. In addition, for example, a configuration may be adopted in which the treatment is detected from the image by using the A1 or the trained model, and the treatment name selection box 75 is displayed immediately after the detection or after a fixed time has elapsed after the detection. In addition, a configuration may be adopted in which the end of the treatment is detected from the image, and the treatment name selection box 75 is displayed immediately after the detection or after a fixed time has elapsed after the detection. By displaying the treatment name selection box 75 after treatment rather than during the treatment, it is possible to concentrate on the treatment during the treatment.

In addition, in a case where the treatment name selection box 75 is displayed after the treatment (including after the treatment tool disappears from the endoscopic image), it is preferable that the treatment name selection box 75 is continuously displayed on the screen for a fixed period. Accordingly, the correction of the selection becomes possible. In addition, the selection can be automatically confirmed after a display period has elapsed.

(4) Display of Treatment Name Selection Box

There are a plurality of types of treatment tools, but it is preferable that, only in a case where a specific treatment tool is detected, the treatment name selection box 75 corresponding to the detected specific treatment tool is displayed on the screen to accept the selection. For example, depending on the treatment tool, there may be only one executable treatment. Therefore, in this case, since there is no room for selection, the display of the treatment name selection box is not necessary.

Note that, for the treatment tool for which there is only one executable treatment, the treatment name may be automatically input in a case where the treatment tool is detected. In this case, instead of displaying the treatment name selection box 75, the treatment name corresponding to the detected treatment tool may be displayed on the screen 70A, and the display of the treatment name disappears after a fixed time has elapsed, thereby confirming the input. Alternatively, a configuration can be adopted in which the treatment name selection box 75 is displayed in combination with the items of "no treatment" and/or "post-selection" to prompt the user to perform the selection.

[Input of Information on Hemostasis]

(1) Selection Operation of Number of Hemostasis Treatment Tools

In the embodiment described above, the configuration is adopted in which the selection operation of the number of hemostasis treatment tools is performed using the foot switch 53 or the audio input device 54, but the selection operation of the number of hemostasis treatment tools is not limited thereto. In addition, for example, a configuration can be adopted in which the selection operation is performed by a foot switch, an audio input, a gaze input, a button operation, a touch operation on a touch panel, and the like. In addition, a configuration may be adopted in which the input can be performed by arbitrarily selecting the plurality of input devices. In addition, the user may be able to arbitrarily set the input devices that can be used.

(2) Input of Hemostatic Method

In the embodiment described above, the configuration is adopted in which, as the information on the hemostasis, in a case where the hemostasis treatment tool is detected from the endoscopic image, the selection box (hemostasis selection box) for selecting the number of hemostasis treatment tools is displayed, but the information to be input regarding the hemostasis is not limited thereto. In addition, for example, a configuration can be adopted in which the hemostatic method is input.

In a case of inputting the hemostatic method, for example, a hemostasis treatment is detected from the endoscopic image by the hemostasis detection unit 63E. Then, in a case where the hemostasis treatment is detected by the hemostasis detection unit 63E, a selection box for the hemostatic method (hemostatic method selection box) is displayed at a predetermined position on the screen.

Figure 39:
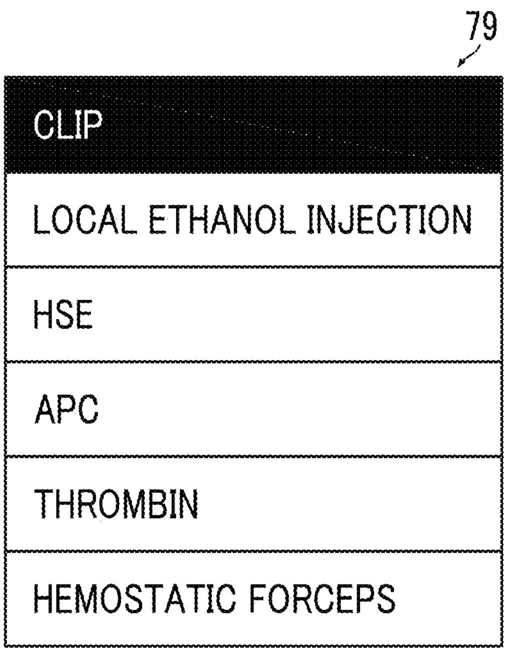
FIG. 39 is a diagram illustrating an example of a hemostatic method selection box.

FIG. 39 is a diagram illustrating an example of the hemostatic method selection box.

As illustrated in the figure, a hemostatic method selection box 79 is configured by a so-called list box, and options of the hemostatic method are displayed in a list. In the example illustrated in FIG. 39, an example of a case in which selectable hemostatic methods are displayed in a list in a vertical line is illustrated. In particular, FIG. 39 illustrates an example of a case where the options of the hemostatic method are "clip", "local ethanol injection", "HSE", "APC", "thrombin", and "hemostatic forceps". Here, "clip" is an option in a case where the hemostasis treatment is performed using a clip method. "Local ethanol injection" is an option in a case where the hemostasis treatment is performed using a pure ethanol local injection method. "HSE" is an option in a case where the hemostasis treatment is performed using a hypertonic saline epinephrine (HSE) method. "APC" is an option in a case where the hemostasis treatment is performed using an argon plasma coagulation (APC) method. "Thrombin" is an option in a case where the hemostasis treatment is performed using a thrombin dispersion method. "Hemostatic forceps" is an option in a case where the hemostasis treatment is performed using the hemostatic forceps. Note that the options of the hemostatic method are not limited thereto.

The options are displayed in a predetermined arrangement. In this case, it is preferable to display the diagnosis names in order of frequency of selection.

Note that, regarding the options of the hemostatic method, a specific option may be selected in advance. In this case, it is more preferable that the option with high frequency of selection is selected in advance.

The option of the hemostatic method displayed in the hemostatic method selection box 79 is another example of the options for the item corresponding to the hemostasis detection unit 63E that is a recognizer.

In this manner, a configuration can be adopted in which, as the option regarding the information on the hemostasis, the hemostatic method is displayed as the option.

Note that, in a case where the hemostatic method is the option as in the example, an input of more detailed information on a specific hemostatic method may be prompted. For example, a configuration can be adopted in which, in the hemostatic method selection box 79 with the above-described configuration, in a case where "clip" is selected, the hemostasis selection box 76 is further displayed on the screen, and the number of hemostasis treatment tools is selected.

(3) Display Timing of Hemostasis Selection Box and Hemostatic Method Selection Box In the embodiment described above, the configuration is adopted in which the hemostasis selection box 76 is displayed on the screen at a timing at which the hemostasis treatment tool is detected from the endoscopic image, but the timing at which the hemostasis selection box 76 is displayed is not limited thereto. For example, a configuration can be adopted in which the display starts after a fixed time has elapsed after the hemostasis treatment tool is detected. The same applies to a case where the hemostatic method selection box is displayed.

In addition, in the embodiment described above, the configuration is adopted in which the hemostasis selection box 76 is continuously displayed on the screen while the hemostasis treatment tool is being detected from the endoscopic image, but a configuration can be adopted in which the hemostasis selection box 76 is displayed only for a fixed period. In addition, the period can be arbitrarily set by the user. In addition, in a case where the display period of the hemostasis selection box 76 is limited to a fixed period, it is preferable to automatically confirm the selection after the fixed period has elapsed. That is, it is preferable to automatically confirm the selection in a case where the hemostasis selection box 76 disappears. The same applies to a case where the hemostatic method selection box is displayed.

(4) Display of Option

The options displayed in the hemostasis selection box and in the hemostatic method selection box may be arbitrarily set by the user. In this case, it is preferable that the user can arbitrarily set and edit the number and order of options to be displayed, the default option, and the like. Accordingly, it is possible to build a user-friendly environment for each user.

In addition, a selection history may be recorded, and the display order may be automatically corrected on the basis of the recorded selection history. For example, on the basis of the history, the display order may be corrected to the descending order of the selection frequency, or the default option may be corrected. Further, for example, the display order may be corrected to an order of newest selection on the basis of the history. In this case, the display is made in the order of the last selected option (previously selected option) displayed at the top, followed by the second-to-last selected option, the third-to-last selected option, and so on. Similarly, on the basis of the history, the last selected option may be corrected to be the default option.

[Display of Each Selection Box]

In the embodiment described above, the selection boxes for the diagnosis name and the findings are displayed on the screen in a case where the discrimination result is output, the selection box for the treatment name is displayed on the screen in a case where the treatment tool is detected from the endoscopic image, and the selection box for the hemostasis is displayed on the screen in a case where the hemostasis treatment tool is detected from the endoscopic image. The conditions for displaying each selection box are not limited thereto. The selection box can be displayed in appropriate combinations. For example, a configuration can be adopted in which the selection box for the findings is displayed on the screen at a timing at which the treatment tool is detected and a timing at which the hemostasis treatment tool is detected.

In addition, a configuration can be adopted in which the selection box for the site is displayed on the screen only for a specific period.

In addition, in a case where the selection box for the site is continuously displayed on the screen, it is preferable to perform the emphasized display as necessary and to prompt the selection of the site. For example, the emphasized display is performed at a timing at which the input of the treatment name is completed, a timing at which the input of the findings is completed, and a timing at which the input of the number of hemostasis treatment tools is completed, and the selection of the site may be prompted.

[Input Information Display Box]

In the embodiment described above, the configuration is adopted in which the input information display box 77 is displayed on the screen in accordance with the display of a predetermined selection box, but the timing of displaying the input information display box 77 is not limited thereto. A configuration can be adopted in which the input information display box is continuously displayed on the screen during the examination. In addition, a configuration can be adopted in which the input information display box is displayed for a fixed time after the selection operation in the selection box. Further, a configuration can be adopted in which the input information display box is displayed at a specific timing. For example, a configuration can be adopted in which the input information display box is displayed for a fixed time on the screen at a stage where the selection processing is completed in all selection boxes. In addition, for example, the input information display box can be displayed at a stage where all the items for the diagnosis name and the findings are selected. Specifically, a configuration can be adopted in which, regarding the diagnosis name and the findings, in a case where the selection boxes are displayed in order of the diagnosis name, the macroscopic classification, the JNET classification, and the size classification, the input information display box 77 is displayed at a stage where the size classification is selected. In this case, the selected information on the diagnosis name and the findings is displayed together.

In addition, a configuration may be adopted in which the input information display box 77 is displayed on the screen at any timing according to the user's instruction.

[Input Device]

In a case where a plurality of input devices can be used, a method of confirming the selection may be changed depending on the input device used. For example, in a case where the selection is accepted by displaying the selection box for a fixed period, a case is considered in which the use of the foot switch 53 and the audio input device 54 is possible. In this case, in a case where the audio input device 54 is used, the selection is confirmed by the audio input. On the other hand, in a case where the foot switch 53 is used, the selection is confirmed after a fixed period has elapsed. That is, the selection is confirmed in conjunction with the disappearance of the selection box from the screen. In a case where the audio input device 54 is used, the selection box disappears from the screen after a fixed period has elapsed after the selection by the audio input.

In addition, in a case where the selection is confirmed by the selection operation, a function of calling the selection box so that the selection operation can be performed again can be provided. For example, the selection box may be redisplayed on the screen by the audio input. In addition, a function of calling a desired selection box at any timing may be provided.

[Detailed Input Screen for Report Creation Support]

In the detailed input screen 140 for the report creation support, it is preferable that the automatically filled input fields are distinguishable from other input fields. For example, the automatically filled input fields is distinguishable from other input fields by being displayed in an emphasized manner. Accordingly, it is possible to clarify that the items are automatically filled, and to call attention to the user.

Figure 40:
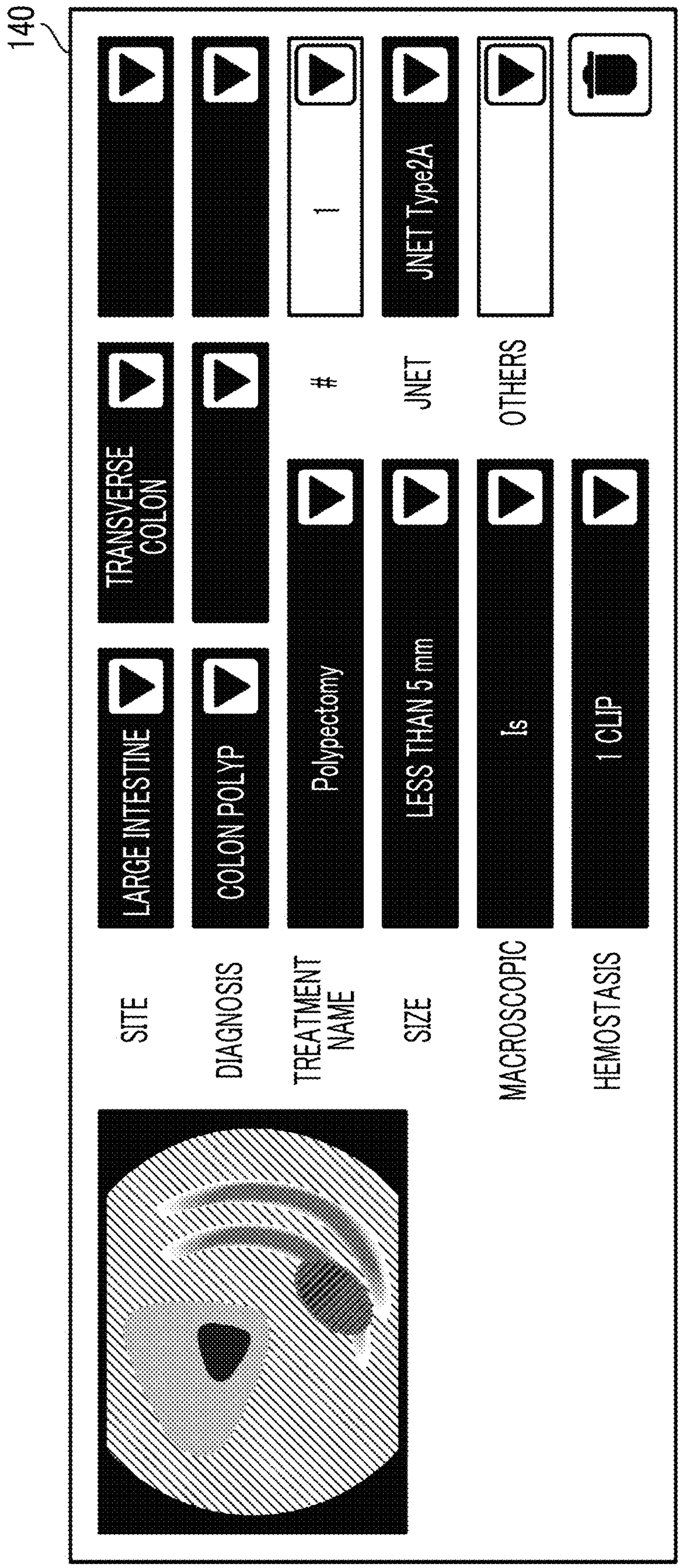
FIG. 40 is a diagram illustrating a modification example of a detailed input screen.

FIG. 40 is a diagram illustrating a modification example of the detailed input screen.

In the example illustrated in the figure, the input field for the site and the input field for the treatment name are displayed in a reversed manner so that the input fields are distinguishable from other input fields. More specifically, a background color and a character color are displayed in a reversed manner so that the input fields are distinguishable from other input fields. Note that FIG. 40 illustrates an example of a case where the input fields 140B1 to 140B3 for the information on the site, the input fields 140C1 to 140C3 for the information on the diagnosis result, the input field 140D for the information on the treatment name, the input field 140E for the information on the size of the lesion part, the input field 140F for the information on the macroscopic classification, the input field 140G for the information on the hemostatic method, and the input field 140I for the information on the JNET classification are automatically filled.

In addition, by making the automatically filled input fields blink, enclosing the automatically filled input fields with a frame, or attaching a caution symbol to the automatically filled input fields, it may be possible to make the automatically filled input fields distinguishable from other input fields.

[Automatic Input]

In the embodiment described above, the information on the site and the information on the treatment name for the lesion or the like as the report creation target are acquired from the database 120, and corresponding input fields are automatically filled, but the method of automatic input is not limited thereto. For example, during the examination, a method can be adopted which records information on the selected site and on the selected treatment name over time (a so-called time log) during the examination, and automatically inputs information on the site, the treatment name, the endoscopic image, and the like by checking with the imaging date and time of the endoscopic image (static image) acquired during the examination. Alternatively, a method can be adopted which records the information on the site and the information on the treatment name in association with the endoscopic image, and automatically inputs the information on the site, the treatment name, the endoscopic image, and the like. In addition, in a case where the endoscopic image is recorded as a video, a method can be adopted which automatically inputs information on the site and on the treatment name from the time information of the video and the information on the time log of the site and the treatment name.

[Hardware Configuration]

Further, the functions of the processor device 40 and of the endoscopic image processing device 60 in the endoscope system 10 are realized by various processors. Similarly, the functions of the endoscope information management device 110 in the endoscope information management system 100 can be realized by various processors.

The various processors include a CPU and/or a graphics processing unit (GPU) as a general-purpose processor executing a program and functioning as various processing units, a programmable logic device (PLD) as a processor of which the circuit configuration can be changed after manufacture, such as a field-programmable gate array (FPGA), and a dedicated electrical circuit as a processor having a circuit configuration designed exclusively for executing specific processing such as an application-specific integrated circuit (ASIC). The program is synonymous with software.

One processing unit may be configured by one processor among these various processors, or may be configured by two or more same or different kinds of processors. For example, one processing unit may be configured by a plurality of FPGAs, or by a combination of a CPU and an FPGA. Further, a plurality of processing units may be configured by one processor. As an example where a plurality of processing units are configured by one processor, first, there is a form where one processor is configured by a combination of one or more CPUs and software as typified by a computer used in a client, a server, or the like, and this processor functions as a plurality of processing units. Second, there is a form where a processor fulfilling the functions of the entire system including a plurality of processing units via one integrated circuit (IC) chip as typified by a system-on-chip (SoC) or the like is used. In this manner, various processing units are configured by using one or more of the above-described various processors as hardware structures.

Further, in the embodiment described above, the processor device 40 and the endoscopic image processing device 60 constituting the endoscope system 10 are separately configured, but the processor device 40 may have the function of the endoscopic image processing device 60. That is, the processor device 40 and the endoscopic image processing device 60 can be integrated. Similarly, the light source device 30 and the processor device 40 can be integrated.

[Examination Target]

In the embodiment described above, a case where the large intestine is examined is exemplified, but the application of the present invention is not limited thereto. The present invention can be similarly applied to a case where other hollow organs are examined. For example, the present invention can be similarly applied to a case where a stomach, a small intestine, or the like is examined.

[Treatment Tool]

In the embodiment described above, biopsy forceps and snares are exemplified as the treatment tool, but the treatment tool that can be used in the endoscope is not limited thereto. Treatment tools can be used as appropriate depending on the hollow organ as the examination target, the content of the treatment, and the like.

EXPLANATION OF REFERENCES

1: endoscopic image diagnosis support system
10: endoscope system
20: endoscope
21: insertion part
21A: distal end portion
21B: bendable portion
21C: soft portion
21*a*: observation window
21*b*: illumination window
21*c*: air/water supply nozzle
21*d*: forceps outlet
22: operation part
22A: angle knob
22B: air/water supply button
22C: suction button
22D: forceps insertion port
23: connecting part
23A: cord
23B: light guide connector
23C: video connector
30: light source device
40: processor device
41: endoscope control unit
42: light source control unit
43: image processing unit
44: input control unit
45: output control unit
50: input device
51: keyboard
52: mouse
53: foot switch
54: audio input device
54A: microphone
54B: audio recognition unit
60: endoscopic image processing device
61: endoscopic image acquisition unit
62: input information acquisition unit
63: image recognition processing unit
63A: lesion part detection unit
63B: discrimination unit
63C: specific region detection unit
63D: treatment tool detection unit
63E: hemostasis detection unit
64: display control unit
65: examination information output control unit
70: display device
70A: screen of display device
71: site selection box
72: diagnosis name selection box
73A: findings selection box
73B: findings selection box
73C: findings selection box
73X: menu box
74: treatment tool detection mark
75: treatment name selection box
76: hemostasis selection box
77: input information display box

78: audio input mark
79: hemostatic method selection box
80: treatment tool
81: hemostasis treatment tool
100: endoscope information management system
110: endoscope information management device
111: examination information acquisition unit
112: examination information recording control unit
113: information output control unit
114: report creation support unit
114A: report creation screen generation unit
114B: automatic input unit
114C: report generation unit
120: database
130: selection screen
131: captured image display region of selection screen
132: detection list display region of selection screen
132A: card displayed in detection list display region
133: merge processing region of selection screen
140: detailed input screen
140A: input field for endoscopic image (static image)
140B1: input field for information on site
140B2: input field for information on site
140B3: input field for information on site
140C1: input field for information on diagnosis result
140C2: input field for information on diagnosis result
140C3: input field for information on diagnosis result
140D: input field for information on treatment name
140E: input field for information on size of lesion
140F: input field for information on macroscopic classification
140G: input field for information on hemostatic method
140H: input field for information on specimen number
140I: input field for information on JNET classification
140J: input field for other information
200: user terminal
A1: main display region of screen during examination
A2: secondary display region of screen during examination
A3: discrimination result display region of screen during examination
Ar: forceps direction
F: frame surrounding lesion region in endoscopic image
I: endoscopic image
IP: information regarding patient
IS: static image
P: lesion part
Sc: schema diagram

What is claimed is:

1. An information processing apparatus comprising:
a first processor,
wherein the first processor is configured to:
acquire images captured by an endoscope in chronological order;
cause a first display unit to display the acquired images in chronological order in a first region set on a screen of the first display unit;
input the acquired images to a plurality of recognizers in chronological order;
detect a recognizer that has output a specific recognition result, from among the plurality of recognizers;
upon detection of the recognizer that has output the specific recognition result, cause the first display unit to display options for an item corresponding to the detected recognizer in a second region set in a different region on the screen of the first display unit from the first region, the second region being set in a vicinity of a position where a treatment tool appears within the acquired images displayed in the first region, the options for the item being registered in a table, the options for the item being arranged in the display according to information on display rank registered in the table; and
accept an input of selection for the displayed options from a plurality of input devices including at least one of an audio input device, a switch, or a gaze input device, for a period set for each recognizer, and
in a case where the first processor detects, while the input of the selection for the displayed options is being accepted, that another specific recognizer of the plurality of recognizers has output another specific recognition result, the first processor switches the displayed options to other options for another item corresponding to the another specific recognizer.

2. The information processing apparatus according to claim 1,
wherein the first processor is configured to set at least one input device that accepts the input of the selection for the options from the plurality of input devices according to the detected recognizer.

3. The information processing apparatus according to claim 1,
wherein the first processor is configured to, in a case where the first processor detects that the recognizer has output the specific recognition result, cause the first display unit to display the options for the item corresponding to the output recognition result.

4. The information processing apparatus according to claim 1,
wherein the first processor is configured to cause the first display unit to display the options while the detected recognizer is outputting the specific recognition result.

5. The information processing apparatus according to claim 1,
wherein the first processor is configured to, in a case where the first processor detects that the recognizer has output the specific recognition result, cause the first display unit to display the recognition result output from the detected recognizer.

6. The information processing apparatus according to claim 5,
wherein the first processor is configured to cause the first display unit to display the recognition result while the recognition result is being output from the detected recognizer.

7. The information processing apparatus according to claim 1,
wherein the first processor is configured to, in a case where the first processor detects that the recognizer has output the specific recognition result, cause the first display unit to display the options for a plurality of items in order.

8. The information processing apparatus according to claim 1,
wherein the first processor is configured to, in a case where the first processor detects that the recognizer has output the specific recognition result, cause the first display unit to display the options for an item designated from among a plurality of items.

9. The information processing apparatus according to claim 1,
wherein the first processor is configured to, in a case where the first processor detects that the recognizer has output the specific recognition result, cause the first display unit to display the options in a state where one option is selected in advance.

10. The information processing apparatus according to claim 1, wherein at least one of the recognizers is configured to accept the input of the selection for the options while the specific recognition result is being output.

11. The information processing apparatus according to claim 1, wherein at least one of the recognizers is configured to continuously accept the input of the selection for the options after the acceptance of the input of the selection for the options starts, except for a specific period.

12. The information processing apparatus according to claim 11, wherein the specific period is a period in which the input of the selection for the options for the item corresponding to a specific recognizer is being accepted.

13. The information processing apparatus according to claim 1, wherein the first processor is configured to cause the first display unit to display a figure or a symbol corresponding to the detected recognizer.

14. The information processing apparatus according to claim 1, wherein the first processor is configured to cause the first display unit to display information on the option selected for each item.

15. The information processing apparatus according to claim 14, wherein the first processor is configured to cause the first display unit to display the information on the option selected for each item while the input of the selection of the options is being accepted.

16. The information processing apparatus according to claim 1, wherein one of the plurality of recognizers is a first recognizer that is configured to detect a specific region of a hollow organ using image recognition, and the first processor is configured to cause the first display unit to display options for selecting a site of the hollow organ as the options for the item corresponding to the first recognizer.

17. The information processing apparatus according to claim 1, wherein one of the plurality of recognizers is a second recognizer that is configured to discriminate a lesion part using image recognition, and the first processor is configured to cause the first display unit to display options for findings as the options for the item corresponding to the second recognizer.

18. The information processing apparatus according to claim 17, wherein the options for the findings include at least one of options for a macroscopic item, options for an item regarding a JNET classification, or options for an item regarding a size.

19. The information processing apparatus according to claim 1, wherein one of the plurality of recognizers is a third recognizer that is configured to detect a treatment or a treatment tool using image recognition, and the first processor is configured to cause the first display unit to display options for a treatment name as the options for the item corresponding to the third recognizer.

20. The information processing apparatus according to claim 1, wherein one of the plurality of recognizers is a fourth recognizer that is configured to detect a hemostasis treatment or a hemostasis treatment tool using image recognition, and the first processor is configured to cause the first display unit to display options for a hemostatic method or the number of hemostasis treatment tools as the options for the item corresponding to the fourth recognizer.

21. The information processing apparatus according to claim 20, wherein the first processor is configured to, in a case where a specific hemostatic method is selected, cause the first display unit to further display the options for the number of hemostasis treatment tools.

22. The information processing apparatus according to claim 1, wherein the first processor is configured to refer to the table in which the options to be displayed are registered for each item.

23. The information processing apparatus according to claim 1, wherein, the first processor is configured to:

record a selection history of the options; and correct the information on display rank registered in the table, based on the selection history.

24. A report creation support device configured to support creation of a report, the report creation support device comprising:

a second processor, wherein the second processor is configured to:

cause a second display unit to display a report creation screen with a plurality of input fields;

acquire information on the options for each item input in the information processing apparatus according to claim 1;

automatically fill the corresponding input field with the acquired information on the options for the item; and accept correction of the information of the automatically filled input field.

25. The report creation support device according to claim 24, wherein the second processor is configured to display the automatically filled input field to be distinguishable from other input fields on the report creation screen.

26. An endoscope system comprising:

an endoscope;

the information processing apparatus according to claim 1; and an input device.

27. An information processing method comprising:

acquiring images captured by an endoscope in chronological order;

causing a first display unit to display the acquired images in chronological order in a first region set on a screen of the first display unit;

inputting the acquired images to a plurality of recognizers in chronological order;

detecting a recognizer that has output a specific recognition result, from among the plurality of recognizers;

upon detection of the recognizer that has output the specific recognition result, causing the first display unit to display options for an item corresponding to the detected recognizer in a second region set in a different region on the screen of the first display unit from the first region, the second region being set in a vicinity of a position where a treatment tool appears within the acquired images displayed in the first region, the options for the item being registered in a table, the options for the item being arranged in the display according to information on display rank registered in the table;

accepting an input of selection for the displayed options from a plurality of input devices including at least one of an audio input device, a switch, or a gaze input device, for a period set for each recognizer; and in a case where, while the input of the selection for the displayed options is being accepted, another specific recognizer of the plurality of recognizers is detected to have output another specific recognition result, switching the displayed options to other options for another item corresponding to the another specific recognizer.

* * * * *